(12) United States Patent
Montell et al.

(10) Patent No.: US 12,741,025 B2
(45) Date of Patent: Sep. 22, 2026

(54) GENETICALLY ENGINEERED PHAGOCYTES, AND RELATED COMPOSITIONS, VECTORS, METHODS AND SYSTEMS

(71) Applicant: The Regents of the University of California, Oakland, CA (US)

(72) Inventors: Denise Montell, Santa Barbara, CA (US); Abhinava K. Mishra, Santa Barbara, CA (US); Alba Y. Torres Espinosa, Santa Barbara, CA (US)

(73) Assignee: The Regents of the University of California, Oakland, CA (US)

(*) Notice: Subject to any disclaimer, the term of this patent is extended or adjusted under 35 U.S.C. 154(b) by 899 days.

(21) Appl. No.: 17/995,083

(22) PCT Filed: Apr. 23, 2021

(86) PCT No.: PCT/US2021/028972

§ 371 (c)(1),
(2) Date: Sep. 29, 2022

(87) PCT Pub. No.: WO2021/217087

PCT Pub. Date: Oct. 28, 2021

(65) Prior Publication Data

US 2024/0293545 A1 Sep. 5, 2024

Related U.S. Application Data

(60) Provisional application No. 63/126,379, filed on Dec. 16, 2020, provisional application No. 63/014,649, filed on Apr. 23, 2020.

(51) Int. Cl.
*A61K 40/30* (2025.01)
*A61K 40/17* (2025.01)
(Continued)

(52) U.S. Cl.
CPC .............. *A61K 40/30* (2025.01); *A61K 40/17* (2025.01); *A61K 40/22* (2025.01); *A61K 40/24* (2025.01);
(Continued)

(58) Field of Classification Search
CPC ........ A61K 40/30; A61K 40/17; A61K 40/22; A61K 40/24; A61K 40/31; A61K 40/416;
(Continued)

(56) References Cited

U.S. PATENT DOCUMENTS 6,468,798 B1 10/2002 Debs et al.
10,125,193 B2 11/2018 Cooper et al.
(Continued)

OTHER PUBLICATIONS

Gabig, Theodore G., et al. "Function of wild-type or mutant Rac2 and Rap1a GTPases in differentiated HL60 cell NADPH oxidase activation." (1995): 804-811. (Year: 1995).*
(Continued)

*Primary Examiner* — Tracy Vivlemore
*Assistant Examiner* — Thomas R. Amick
(74) *Attorney, Agent, or Firm* — Edward J. Baba; Bozicevic, Field & Francis LLP

(57) ABSTRACT

Genetically engineered activated phagocytic cells are described and related vectors, compositions, methods and systems which allow efficient cell targeting through enhanced phagocytosis of target cells and treatment of conditions in an individual.

9 Claims, 31 Drawing Sheets

Specification includes a Sequence Listing.

(51) Int. Cl.

| | |
|---|---|
| ***A61K 40/22*** | (2025.01) |
| ***A61K 40/24*** | (2025.01) |
| ***A61K 40/31*** | (2025.01) |
| ***A61K 40/41*** | (2025.01) |
| ***A61K 40/42*** | (2025.01) |
| ***C07K 14/705*** | (2006.01) |
| ***C12N 5/0786*** | (2010.01) |
| ***C12N 9/14*** | (2006.01) |

(52) U.S. Cl.

CPC ............ *A61K 40/31* (2025.01); *A61K 40/416* (2025.01); *A61K 40/4205* (2025.01); *A61K 40/4253* (2025.01); *C07K 14/7051* (2013.01); *C12N 5/0645* (2013.01); *C12N 9/14* (2013.01); *C12Y 306/05002* (2013.01); *A61K 2239/48* (2023.05); *C12N 2510/00* (2013.01); *C12N 2830/003* (2013.01)

(58) Field of Classification Search

CPC ............ A61K 40/4205; A61K 40/4253; A61K 2239/48; C07K 14/7051; C12N 5/0645; C12N 9/14; C12N 2510/00; C12N 2830/003; C12N 2501/73; C12N 5/0601; C12Y 306/05002

See application file for complete search history.

(56) References Cited

U.S. PATENT DOCUMENTS

| | | | |
|---|---|---|---|
| 2015/0185223 | A1 | 7/2015 | Mano et al. |
| 2020/0055917 | A1 | 2/2020 | Corey |
| 2020/0239592 | A1 | 7/2020 | Vale et al. |

OTHER PUBLICATIONS

Pulgar et al., RAC2 (ras-related C3 botulinum toxin substrate 2 (rho family, small GTP binding protein Rac2)) Atlas Genet Cytogenet Oncol Haematol. Aug. 1, 2008. https://atlasgeneticsoncology.org/gene/42021/rac2-(ras-related-c3-botulinum-toxin-substrate-2-(rho-family-small-gtp-binding-protein-rac2)) (Year: 2008).*

Ladd, Paula D., Jill Sergesketter Butler, and David G. Skalnik. "Identification of a genomic fragment that directs hematopoietic-specific expression of Rac2 and analysis of the DNA methylation profile of the gene locus." Gene 341 (2004): 323-333. (Year: 2004).*

Gu X, He D, Li C, Wang H, Yang G. Development of Inducible CD19-CAR T Cells with a Tet-On System for Controlled Activity and Enhanced Clinical Safety. Int J Mol Sci. Nov. 3, 2018;19(11):3455 (Year: 2018).*

Guo, Fukun, et al. "Rac GTPase isoforms Rac1 and Rac2 play a redundant and crucial role in T-cell development." Blood, The Journal of the American Society of Hematology 112.5 (2008): 1767-1775 (Year: 2008).*

Cernuda-Morollón et al., Rac activation by the T-cell receptor inhibits T cell migration. PLoS One. Aug. 25, 2010;5(8):e12393 (Year: 2010).*

Acuner et al. (2021) "Oncogenic mutations on Rac1 affect global intrinsic dynamics underlying GTP and PAK1 binding" Biophysical Journal, 120: 866-876, Mar. 2, 2021.

Buchler et al. (2003) "On schemes of combinatorial transcription logic." Proceedings of the National Academy of Sciences 100:9 5136-5141.

Cai et al. (2014) "Mechanical feedback through E-cadherin promotes direction sensing during collective cell migration." Cell 157:5 1146-1159.

Elliott et al., (2016) "The dynamics of apoptotic cell clearance." Developmental cell 38:2 147-160.

Gabig et al. (1995) "Function of wild-type or mutant Rac2 and Rap1a GTPases in differentiated HL60 cell NADPH oxidase activation", Blood, 85:3, pp. 804-811.

Geisbrecht et al. (2004) "A role for *Drosophila* IAP1-mediated caspase inhibition in Rac-dependent cell migration." Cell 118(1): 111-125.

Giannakopoulos et al. (2003) "Tangle and neuron numbers, but not amyloid load, predict cognitive status in Alzheimer's disease" Neurology 60;9 1495-1500.

Haataja et al. (1997) "Characterization of RAC3, a novel member of the Rho family" Journal of Biological Chemistry 272:33 20384-20388.

Hall (1998) "Rho GTPases and the actin cytoskeleton." Science 279(5350): 509-514.

Heyerdahl et al. (2011) "Treatment of HER2-expressing breast cancer and ovarian cancer cells with alpha particle-emitting 227Th-trastuzumab" International Journal of Radiation Oncology* Biology* Physics 79:2 563-570.

Hsu et al. (2019) "Dominant activating RAC2 mutation with lymphopenia, immunodeficiency, and cytoskeletal defects" Blood 133:18 1977-1988.

Jayasingam et al. (2020) "Evaluating the polarization of tumor-associated macrophages into M1 and M2 phenotypes in human cancer tissue: technicalities and challenges in routine clinical practice" Frontiers in oncology 9: 1512.

Jernström, S., et al. (2017). "Drug-screening and genomic analyses of HER2-positive breast cancer cell lines reveal predictors for treatment response." Breast Cancer: Targets and Therapy 9: 185.

Karlin et al., (1990) "Methods for assessing the statistical significance of molecular sequence features by using general scoring schemes" Proceedings of the National Academy of Sciences 87:6 2264-2268.

Karlin et al. (1993) "Applications and statistics for multiple high-scoring segments in molecular sequences" Proceedings of the National Academy of Sciences 90:12 5873-5877.

Kawazu et al., (2013) "Transforming mutations of RAC guanosine triphosphatases in human cancers" Proceedings of the National Academy of Sciences 110:8 3029-3034.

Klichinsky et al. (2020) "Human chimeric antigen receptor macrophages for cancer immunotherapy" Nature biotechnology 38:8 947-953.

Krauthammer et al. (2012) "Exome sequencing identifies recurrent somatic RAC1 mutations in melanoma" Nature genetics 44:9 1006-1014.

Kumar et al., (2013) "Molecular dynamic simulation reveals damaging impact of RAC1 F28L mutation in the switch I region." PloS one 8:10 e77453.

Kuo et al. (1996) "Water-soluble Aβ (N-40, N-42) oligomers in normal and Alzheimer disease brains" Journal of Biological Chemistry 27:8 4077-4081.

Lagresle-Peyrou et al. (2021) "A gain-of-function RAC2 mutation is associated with bone marrow hypoplasia and an autosomal dominant form of severe combined immunodeficiency" haematologica 106:2 404.

Lesné et al. (2006) "A specific amyloid-β protein assembly in the brain impairs memory" Nature 440:7082 352-357.

Lougaris et al. (2019) "A monoallelic activating mutation in RAC2 resulting in a combined immunodeficiency" Journal of Allergy and Clinical Immunology 143:4 1649-1653. e1643.

Mandrekar et al. (2009) "Microglia mediate the clearance of soluble Aβ through fluid phase macropinocytosis" Journal of Neuroscience 29:13 4252-4262.

Mantovani et al. (2017) "Tumour-associated macrophages as treatment targets in oncology" Nature reviews Clinical oncology 14:7 399.

Massol et al. (1998) "Fc receptor-mediated phagocytosis requires CDC42 and Rac1." The EMBO journal 17:21 6219-6229.

Matlung et al. (2018). "Neutrophils kill antibody-opsonized cancer cells by trogoptosis" Cell Reports 23:13 3946-3959. e3946.

Meehan et al. (2015) "Polarization of the epithelial layer and apical localization of integrins are required for engulfment of apoptotic cells in the *Drosophila ovary*" Disease models & mechanisms 8:12 1603-1614.

(56) References Cited

OTHER PUBLICATIONS

Menard (1993) "Role of phosphate-magnesium-binding regions in the high GTPase activity of rac1 protein" Biochemistry 32:48 13357-13361.
Milone et al. (2009) "Chimeric receptors containing CD137 signal transduction domains mediate enhanced survival of T cells and increased antileukemic efficacy in vivo" Molecular therapy 17:8 1453-1464.
Mishra et al. (2019) "Coordination of protrusion dynamics within and between collectively migrating border cells by myosin II" Molecular biology of the cell 30:19 2490-2502.
Montell et al. (1992) "slow border cells, a locus required for a developmentally regulated cell migration during oogenesis, encodes *Drosophila* CEBP" Cell 71:1 51-62.
Montell et al. (2012) "Group choreography: mechanisms orchestrating the collective movement of border cells." Nature reviews Molecular cell biology 13:10 631-645.
Morrissey et al., (2019) "CD47 suppresses phagocytosis by repositioning SIRPA and preventing integrin activation" bioRxiv: 752311.
Morrissey et al. (2018) "Chimeric antigen receptors that trigger phagocytosis" Elife 7: e36688.
Murphy et al. (1996) "Cell type-specific roles for Cdc42, Rac, and RhoL in *Drosophila oogenesis*." The Journal of cell biology 133:3 617-630.
Myers et al. (1988) "Optimal alignments in linear space." Bioinformatics 4:1 11-17.
Needleman et al. (1970) "A general method applicable to the search for similarities in the amino acid sequence of two proteins" Journal of molecular biology 48:3 443-453.
Olivera-Perez et al. (2017) "Omega-3 fatty acids increase the unfolded protein response and improve amyloid-β phagocytosis by macrophages of patients with mild cognitive impairment" The FASEB Journal 31:10 4359-4369.
Onuma et al. (2014) "Rapidly rendering cells phagocytic through a cell surface display technique and concurrent Rac activation" Science signaling 7:334 rs4-rs4.
Pantarelli et al. (2018) "Rac-GTP ases and Rac-GEF s in neutrophil adhesion, migration and recruitment" European journal of clinical investigation 48: e12939.
Panza et al. (2019) "Amyloid-β immunotherapy for alzheimer disease: Is it now a long shot?" Annals of neurology 85(3): 303-315.
Pearson (1988) "Improved tools for biological sequence comparison" Proceedings of the National Academy of Sciences 85(8): 2444-2448.
Peterson et al. (2003) "Stage-specific regulation of caspase activity in *Drosophila oogenesis*" Developmental biology 260:1 113-123.
Prasad et al. (2007) "Cellular and molecular mechanisms of border cell migration analyzed using time-lapse live-cell imaging" Developmental cell 12:6 997-1005.
Ray et al. (2017) "Glial draper rescues Aβ toxicity in a *Drosophila* model of Alzheimer's disease" Journal of Neuroscience 37:49 11881-11893.
Ridley et al. (1992) "The small GTP-binding protein rac regulates growth factor-induced membrane ruffling" Cell 70:3: 401-410.
Ridley (2015) "Rho GTPase signalling in cell migration." Current opinion in cell biology 36: 103-112.
Rorth et al. (1998) "Systematic gain-of-function genetics in *Drosophila*." Development 125:6 1049-1057.
Roth et al. (2018) "Reprogramming human T cell function and specificity with non-viral genome targeting" Nature 559:7714 405-409.
Sambrook et al. (1989) Molecular cloning: a laboratory manual 2nd ed., Cold spring harbor laboratory press.
Serizier et al. (2017) "Scrambled eggs: Apoptotic cell clearance by non-professional phagocytes in the *Drosophila ovary*" Frontiers in immunology 8: 1642.
Silva-Rocha et al. (2008) "Mining logic gates in prokaryotic transcriptional regulation networks" FEBS letters 582:8 1237-1244.
Smith et al. (1981) "Comparison of biosequences." Advances in applied mathematics 2:4 482-489.
Songs et al. (2014) "Effects of LPLI on microglial phagocytosis in LPS-induced neuro inflammation model" Journal of Innovative Optical Health Sciences, 7:3, 10 pages.
Struhl et al. (1993) "Organizing activity of wingless protein in *Drosophila*" Cell 72:4 527-540.
Timmons et al. (2016) "Phagocytosis genes nonautonomously promote developmental cell death in the *Drosophila ovary*" Proceedings of the National Academy of Sciences 113:9 E1246-E1255.
Van Tendeloo et al. (2000) "High-level transgene expression in primary human T lymphocytes and adult bone marrow CD34+ cells via electroporation-mediated gene delivery" Gene therapy 7:16 1431-1437.
Wang et al. (2010) "Light-mediated activation reveals a key role for Rac in collective guidance of cell movement in vivo" Nature cell biology 12;6 591-597.
Weiskopf (2017) "Cancer immunotherapy targeting the CD47/SIRPα axis" European journal of cancer 76: 100-109.
Wikipedia, F. c. (Apr. 20, 2021). "Fold change, https://en.wikipedia.org/wiki/Fold_change.".
Wikipedia, R. (Dec. 31, 2020). "RAC1 https://en.wikipedia.org/wiki/RAC1 ".
Xu et al. (1997) "Guanine nucleotide binding properties of Rac2 mutant proteins and analysis of the responsiveness to guanine nucleotide dissociation stimulator" Biochemistry 36:3 626-632.
Zarani et al. (1991) "The eggshell of *Drosophlla melanogaster*" Roux's archives of developmental biology 200:2 95-103.

* cited by examiner

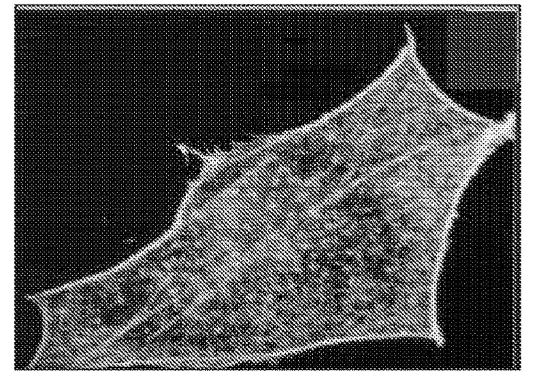
FIG. 1B
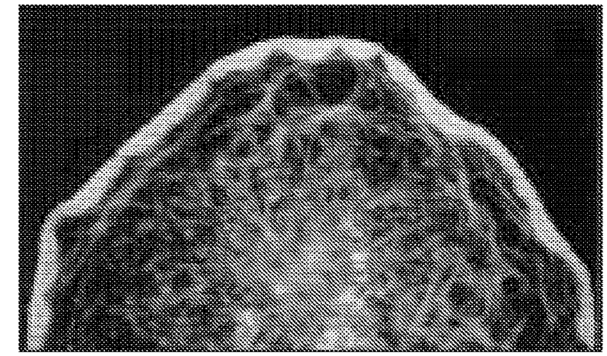
FIG. 1C
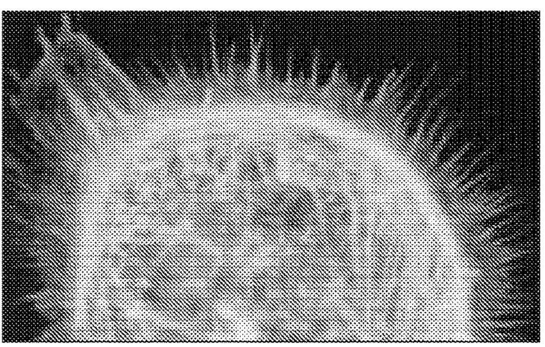
FIG. 1D
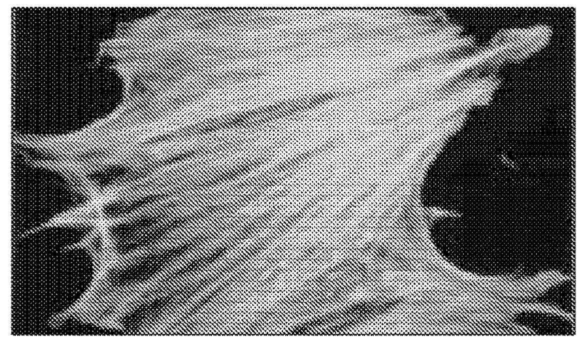
FIG. 1E

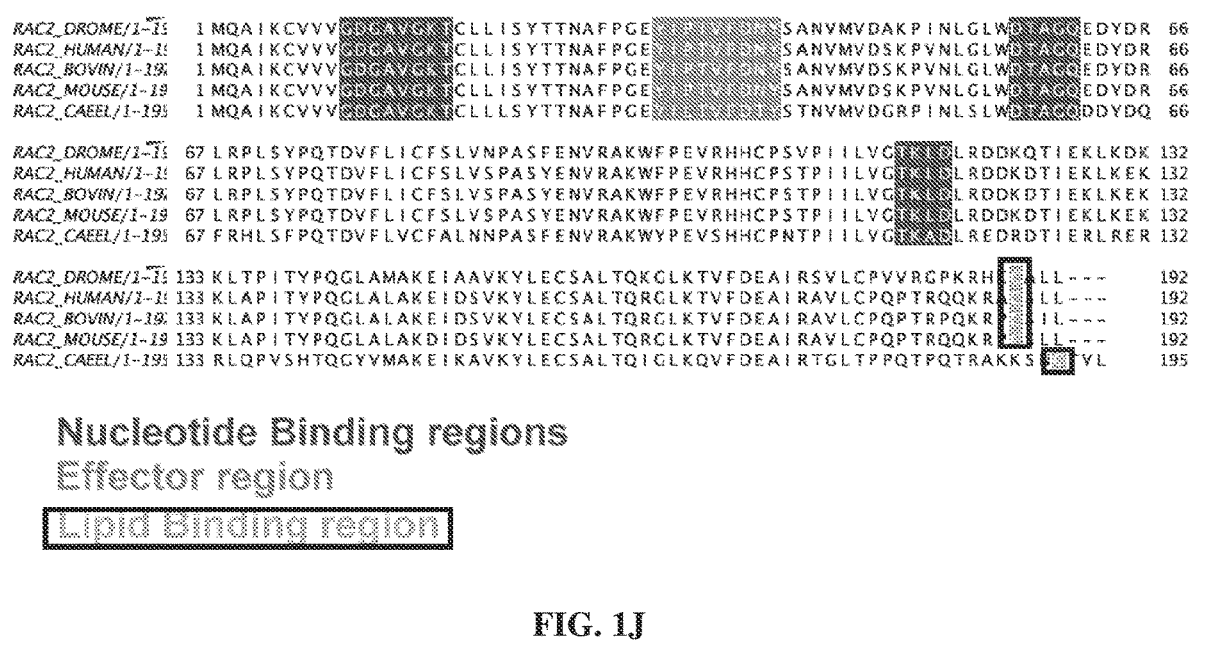

```
RAC2_DROME/1-1   1 MQAIKCVVV[illegible]CLLISYTTNAFPGE[illegible]SANVMVDAKPINLGLW[illegible]EDYDR  66
RAC2_HUMAN/1-1   1 MQAIKCVVV[illegible]CLLISYTTNAFPGE[illegible]SANVMVDSKPVNLGLW[illegible]EDYDR  66
RAC2_BOVIN/1-19  1 MQAIKCVVV[illegible]CLLISYTTNAFPGE[illegible]SANVMVDSKPVNLGLW[illegible]EDYDR  66
RAC2_MOUSE/1-19  1 MQAIKCVVV[illegible]CLLISYTTNAFPGE[illegible]SANVMVDSKPVNLGLW[illegible]EDYDR  66
RAC2_CAEEL/1-19  1 MQAIKCVVV[illegible]CLLLSYTTNAFPGE[illegible]STNVMVDGRPINLSLW[illegible]DDYDQ  66

RAC2_DROME/1-1  67 LRPLSYPQTDVFLICFSLVNPASFENVRAKWFPEVRHHCPSVPIILVG[illegible]LRDDKQTIEKLKDK 132
RAC2_HUMAN/1-1  67 LRPLSYPQTDVFLICFSLVSPASYENVRAKWFPEVRHHCPSTPIILVG[illegible]LRDDKDTIEKLKEK 132
RAC2_BOVIN/1-19 67 LRPLSYPQTDVFLICFSLVSPASYENVRAKWFPEVRHHCPSTPIILVG[illegible]LRDDKDTIEKLKEK 132
RAC2_MOUSE/1-19 67 LRPLSYPQTDVFLICFSLVSPASYENVRAKWFPEVRHHCPSTPIILVG[illegible]LRDDKDTIEKLKEK 132
RAC2_CAEEL/1-19 67 FRHLSFPQTDVFLVCFALNNPASFENVRAKWYPEVSHHCPNTPIILVG[illegible]LREDRDTIERLRER 132

RAC2_DROME/1-1  133 KLTPITYPQGLAMAKEIAAVKYLECSALTQKGLKTVFDEAIRSVLCPVVRGPKRH[illegible]LL---  192
RAC2_HUMAN/1-1  133 KLAPITYPQGLALAKEIDSVKYLECSALTQRGLKTVFDEAIRAVLCPQPTRQQKR[illegible]LL---  192
RAC2_BOVIN/1-19 133 KLAPITYPQGLALAKEIDSVKYLECSALTQRGLKTVFDEAIRAVLCPQPTRPQKR[illegible]IL---  192
RAC2_MOUSE/1-19 133 KLAPITYPQGLALAKDIDSVKYLECSALTQRGLKTVFDEAIRAVLCPQPTRQQKR[illegible]LL---  192
RAC2_CAEEL/1-19 133 RLQPVSHTQGYVMAKEIKAVKYLECSALTQIGLKQVFDEAIRTGLTPPQTPQTRAKKS[illegible]YL  195
```

Nucleotide Binding regions

Effector region

Lipid Binding region

FIG. 1J

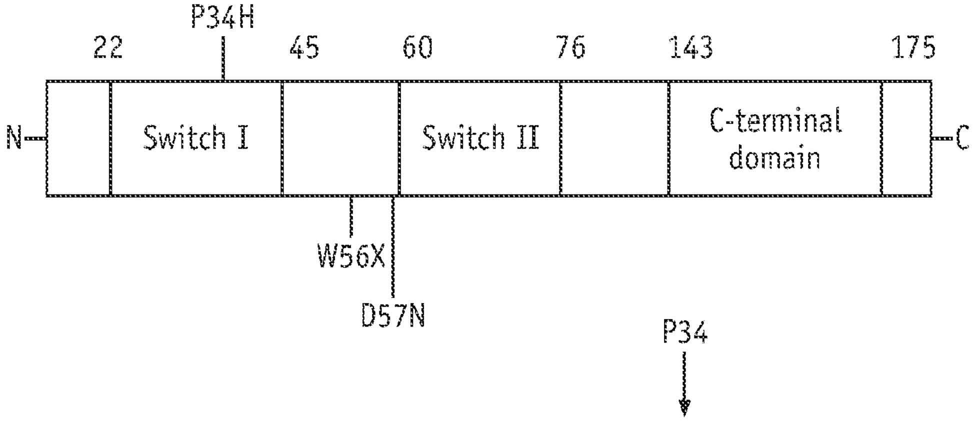

```
Mouse MQAIKCVVVGDGAVGKTCLLISYTTNAFPGEYIPTVFDNYSANVM\
Rat MQAIKCVVVGDGAVGKTCLLISYTTNAFPGEYIPTVFDNYSANVM\
Human MQAIKCVVVGDGAVGKTCLLISYTTNAFPGEYIPTVFDNYSANVM\
Cow MQAIKCVVVGDGAVGKTCLLISYTTNAFPGEYIPTVFDNYSANVM\
Zebrafish MQAIKCVVVGDGAVGKTCLLISYTTNAFPGEYIPTVFDNYSANVM\
Chimpanzee MQAIKCVVVGDGAVGKTCLLISYTTNAFPGEYIPTVFDNYSANVM\
```

*FIG. 1K*

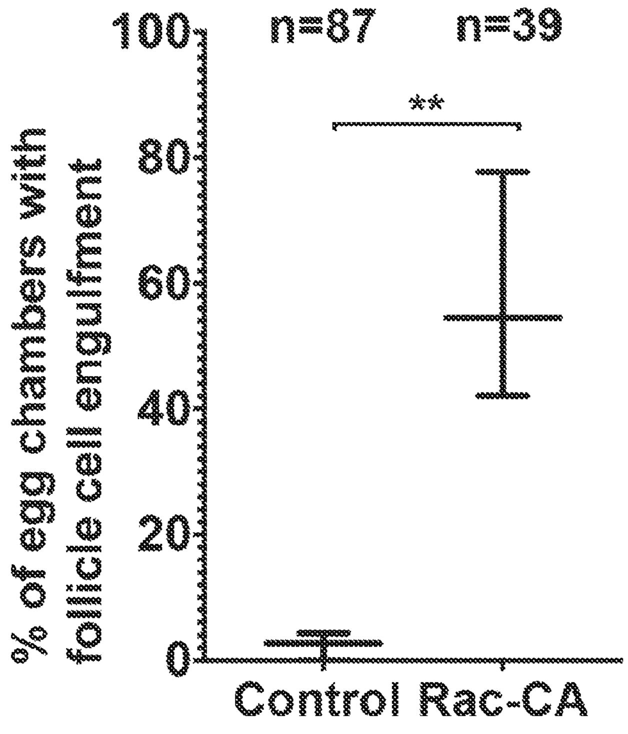
FIG. 2R
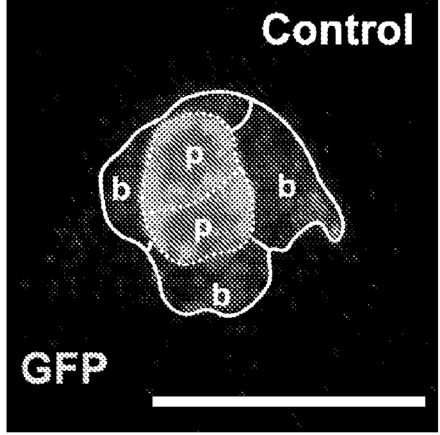
FIG. 2S
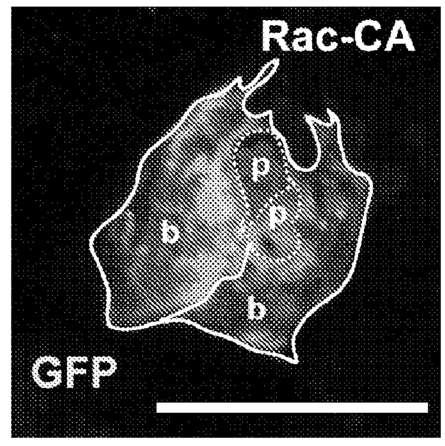
FIG. 2T

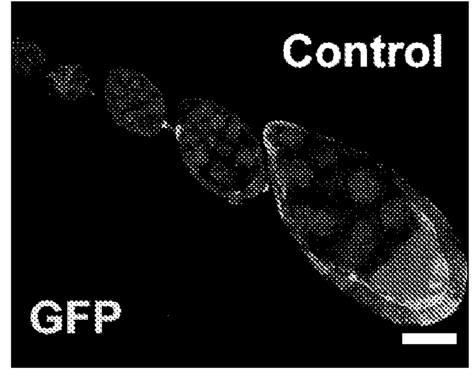
FIG. 3A
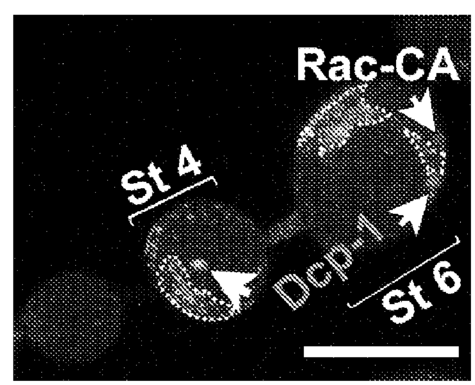
FIG. 3B
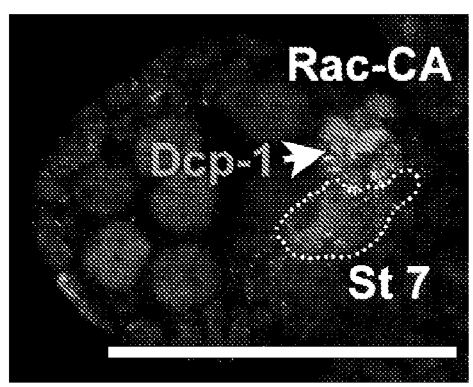
FIG. 3C
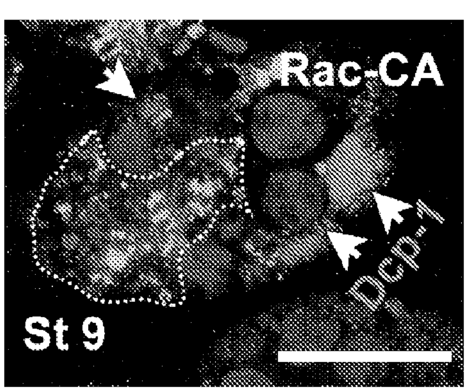
FIG. 3D

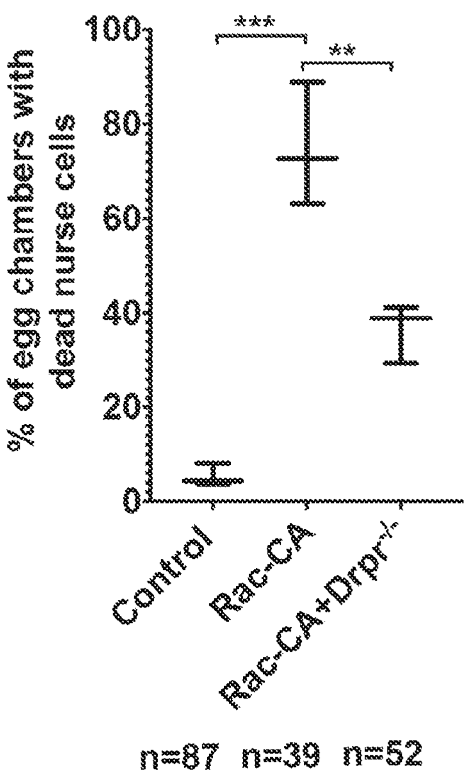
FIG. 4G
Normalized nurse cell E-Cad intensity
1.0
0.8
0.6
0.4
0.2
0.0
**
****
Control
Rac-CA
Rac-CA+Drpr-/-
FIG. 4H
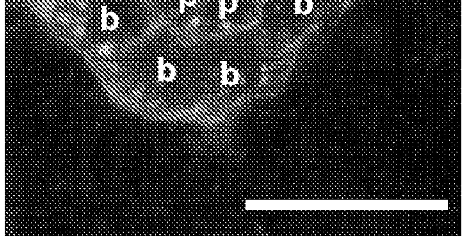
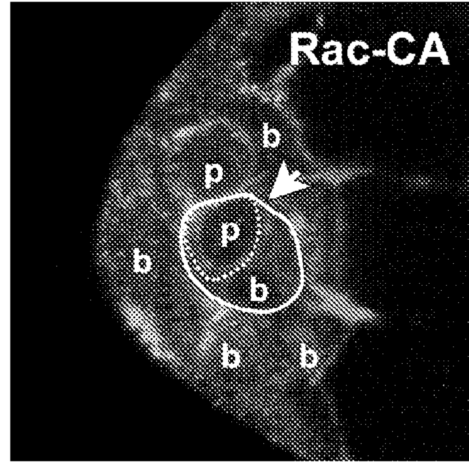
FIG. 4I
FIG. 4J

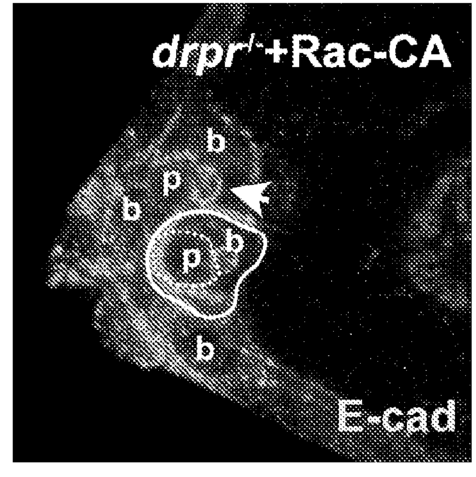
FIG. 4K
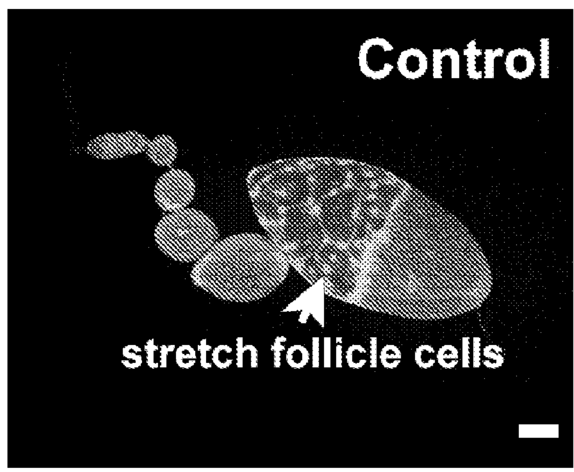
FIG. 4L
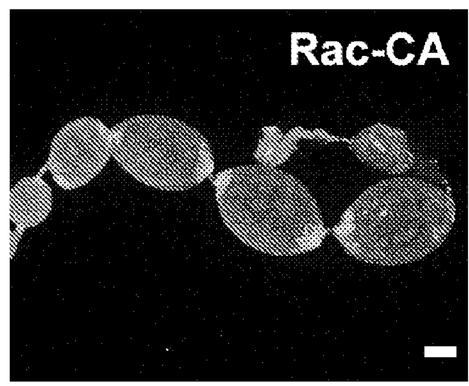
FIG. 4M
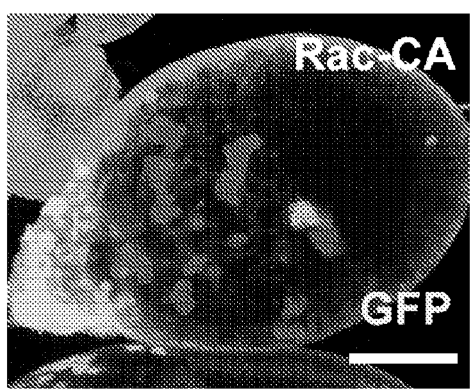
FIG. 4N

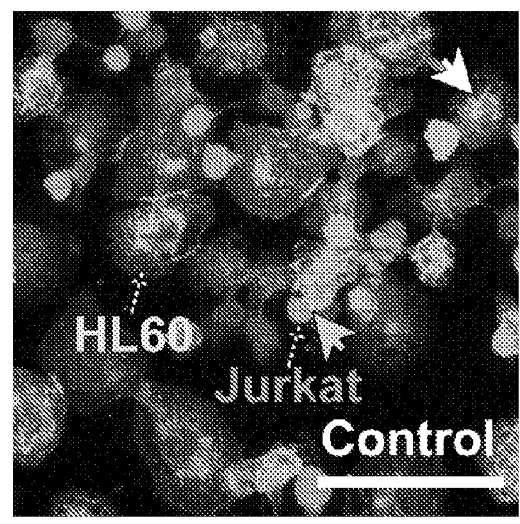
FIG. 5A
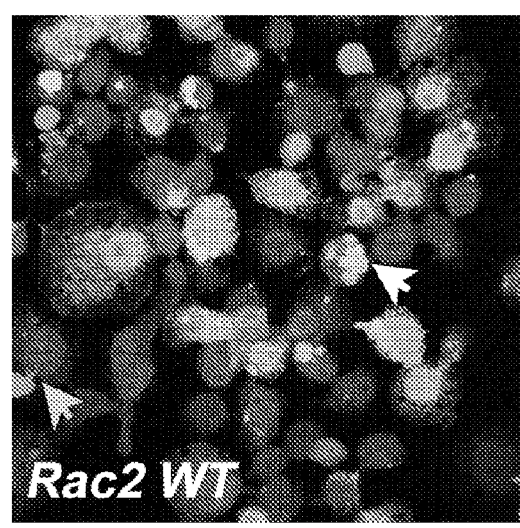
FIG. 5B
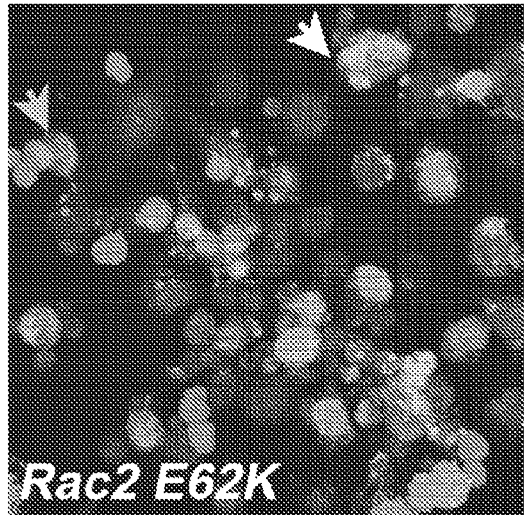
FIG. 5C

SEQUENCE LISTING

<160> NUMBER OF SEQ ID NOS: 15

<210> SEQ ID NO 1
<211> LENGTH: 192
<212> TYPE: PRT
<213> ORGANISM: Homo sapiens

<400> SEQUENCE: 1

```
Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Ser
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Tyr Glu Asn Val Arg Ala Lys
                85                  90                  95

Trp Phe Pro Glu Val Arg His His Cys Pro Ser Thr Pro Ile Ile Leu
            100                 105                 110

Val Gly Thr Lys Leu Asp Leu Arg Asp Asp Lys Asp Thr Ile Glu Lys
        115                 120                 125

Leu Lys Glu Lys Lys Leu Ala Pro Ile Thr Tyr Pro Gln Gly Leu Ala
    130                 135                 140

Leu Ala Lys Glu Ile Asp Ser Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Gln Pro Thr Arg Gln Gln Lys Arg Ala Cys Ser Leu Leu
            180                 185                 190
```

<210> SEQ ID NO 2
<211> LENGTH: 192
<212> TYPE: PRT
<213> ORGANISM: Homo sapiens

<400> SEQUENCE: 2

```
Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
            100                 105                 110

Val Gly Thr Lys Leu Asp Leu Arg Asp Asp Lys Asp Thr Ile Glu Lys
        115                 120                 125

Leu Lys Glu Lys Lys Leu Thr Pro Ile Thr Tyr Pro Gln Gly Leu Ala
```

```
    130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu
            180                 185                 190


<210> SEQ ID NO 3
<211> LENGTH: 192
<212> TYPE: PRT
<213> ORGANISM: Homo sapiens

<400> SEQUENCE: 3

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro His Thr Pro Ile Leu Leu
            100                 105                 110

Val Gly Thr Lys Leu Asp Leu Arg Asp Asp Lys Asp Thr Ile Glu Arg
        115                 120                 125

Leu Arg Asp Lys Lys Leu Ala Pro Ile Thr Tyr Pro Gln Gly Leu Ala
    130                 135                 140

Met Ala Arg Glu Ile Gly Ser Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Pro Gly Lys Lys Cys Thr Val Phe
            180                 185                 190


<210> SEQ ID NO 4
<211> LENGTH: 191
<212> TYPE: PRT
<213> ORGANISM: Homo sapiens

<400> SEQUENCE: 4

Met Gln Thr Ile Lys Cys Val Val Val Gly Asp Gly Ala Val Gly Lys
1               5                   10                  15

Thr Cys Leu Leu Ile Ser Tyr Thr Thr Asn Lys Phe Pro Ser Glu Tyr
            20                  25                  30

Val Pro Thr Val Phe Asp Asn Tyr Ala Val Thr Val Met Ile Gly Gly
        35                  40                  45

Glu Pro Tyr Thr Leu Gly Leu Phe Asp Thr Ala Gly Gln Glu Asp Tyr
    50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
```

```
                85                  90                  95

Trp Val Pro Glu Ile Thr His His Cys Pro Lys Thr Pro Phe Leu Leu
            100                 105                 110

Val Gly Thr Gln Ile Asp Leu Arg Asp Asp Pro Ser Thr Ile Glu Lys
        115                 120                 125

Leu Ala Lys Asn Lys Gln Lys Pro Ile Thr Pro Glu Thr Ala Glu Lys
    130                 135                 140

Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
            180                 185                 190


<210> SEQ ID NO 5
<211> LENGTH: 192
<212> TYPE: PRT
<213> ORGANISM: Drosophila melanogaster

<400> SEQUENCE: 5

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Ala
        35                  40                  45

Lys Pro Ile Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Asn Pro Ala Ser Phe Glu Asn Val Arg Ala Lys
                85                  90                  95

Trp Tyr Pro Glu Val Arg His His Cys Pro Ser Thr Pro Ile Ile Leu
            100                 105                 110

Val Gly Thr Lys Leu Asp Leu Arg Asp Asp Lys Asn Thr Ile Glu Lys
        115                 120                 125

Leu Arg Asp Lys Lys Leu Ala Pro Ile Thr Tyr Pro Gln Gly Leu Ala
    130                 135                 140

Met Ala Lys Glu Ile Gly Ala Val Lys Tyr Leu Glu Cys Ser Ala Leu
145                 150                 155                 160

Thr Gln Lys Gly Leu Lys Thr Val Phe Asp Glu Ala Ile Arg Ser Val
                165                 170                 175

Leu Cys Pro Val Leu Gln Pro Lys Ser Lys Arg Lys Cys Ala Leu Leu
            180                 185                 190


<210> SEQ ID NO 6
<211> LENGTH: 192
<212> TYPE: PRT
<213> ORGANISM: Bos taurus

<400> SEQUENCE: 6

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
```

```
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
            100                 105                 110

Val Gly Thr Lys Leu Asp Leu Arg Asp Asp Lys Asp Thr Ile Glu Lys
        115                 120                 125

Leu Lys Glu Lys Lys Leu Thr Pro Ile Thr Tyr Pro Gln Gly Leu Ala
    130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu
            180                 185                 190


<210> SEQ ID NO 7
<211> LENGTH: 211
<212> TYPE: PRT
<213> ORGANISM: Mus musculus

<400> SEQUENCE: 7

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Val Gly Asp Thr Cys
65                  70                  75                  80

Gly Lys Asp Arg Pro Ser Arg Gly Lys Asp Lys Pro Ile Ala Asp Val
                85                  90                  95

Phe Leu Ile Cys Phe Ser Leu Val Ser Pro Ala Ser Phe Glu Asn Val
            100                 105                 110

Arg Ala Lys Trp Tyr Pro Glu Val Arg His His Cys Pro Asn Thr Pro
        115                 120                 125

Ile Ile Leu Val Gly Thr Lys Leu Asp Leu Arg Asp Asp Lys Asp Thr
    130                 135                 140

Ile Glu Lys Leu Lys Glu Lys Lys Leu Thr Pro Ile Thr Tyr Pro Gln
145                 150                 155                 160

Gly Leu Ala Met Ala Lys Glu Ile Gly Ala Val Lys Tyr Leu Glu Cys
                165                 170                 175

Ser Ala Leu Thr Gln Arg Gly Leu Lys Thr Val Phe Asp Glu Ala Ile
            180                 185                 190

Arg Ala Val Leu Cys Pro Pro Pro Val Lys Lys Arg Lys Arg Lys Cys
        195                 200                 205

Leu Leu Leu
    210
```

<210> SEQ ID NO 8
<211> LENGTH: 191
<212> TYPE: PRT
<213> ORGANISM: Caenorhabditis elegans

<400> SEQUENCE: 8

```
Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
        35                  40                  45

Arg Pro Ile Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Val
65                  70                  75                  80

Cys Phe Ala Leu Asn Asn Pro Ala Ser Phe Glu Asn Val Arg Ala Lys
                85                  90                  95

Trp Tyr Pro Glu Val Ser His His Cys Pro Asn Thr Pro Ile Ile Leu
            100                 105                 110

Val Gly Thr Lys Ala Asp Leu Arg Glu Asp Arg Asp Thr Val Glu Arg
        115                 120                 125

Leu Arg Glu Arg Arg Leu Gln Pro Val Ser Gln Thr Gln Gly Tyr Val
    130                 135                 140

Met Ala Lys Glu Ile Lys Ala Val Lys Tyr Leu Glu Cys Ser Ala Leu
145                 150                 155                 160

Thr Gln Arg Gly Leu Lys Gln Val Phe Asp Glu Ala Ile Arg Ala Val
                165                 170                 175

Leu Thr Pro Pro Gln Arg Ala Lys Lys Ser Lys Cys Thr Val Leu
            180                 185                 190
```

<210> SEQ ID NO 9
<211> LENGTH: 192
<212> TYPE: PRT
<213> ORGANISM: Drosophila melanogaster

<400> SEQUENCE: 9

```
Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Ala
        35                  40                  45

Lys Pro Ile Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Asn Pro Ala Ser Phe Glu Asn Val Arg Ala Lys
                85                  90                  95

Trp Phe Pro Glu Val Arg His His Cys Pro Ser Val Pro Ile Ile Leu
            100                 105                 110

Val Gly Thr Lys Leu Asp Leu Arg Asp Asp Lys Gln Thr Ile Glu Lys
        115                 120                 125

Leu Lys Asp Lys Lys Leu Thr Pro Ile Thr Tyr Pro Gln Gly Leu Ala
    130                 135                 140
```

```
Met Ala Lys Glu Ile Ala Ala Val Lys Tyr Leu Glu Cys Ser Ala Leu
145                 150                 155                 160

Thr Gln Lys Gly Leu Lys Thr Val Phe Asp Glu Ala Ile Arg Ser Val
                165                 170                 175

Leu Cys Pro Val Val Arg Gly Pro Lys Arg His Lys Cys Ala Leu Leu
            180                 185                 190


<210> SEQ ID NO 10
<211> LENGTH: 192
<212> TYPE: PRT
<213> ORGANISM: Bos taurus

<400> SEQUENCE: 10

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Ser
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Tyr Glu Asn Val Arg Ala Lys
                85                  90                  95

Trp Phe Pro Glu Val Arg His His Cys Pro Ser Thr Pro Ile Ile Leu
            100                 105                 110

Val Gly Thr Lys Leu Asp Leu Arg Asp Asp Lys Asp Thr Ile Glu Lys
        115                 120                 125

Leu Lys Glu Lys Lys Leu Ala Pro Ile Thr Tyr Pro Gln Gly Leu Ala
    130                 135                 140

Leu Ala Lys Glu Ile Asp Ser Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Gln Pro Thr Arg Pro Gln Lys Arg Pro Cys Ser Ile Leu
            180                 185                 190


<210> SEQ ID NO 11
<211> LENGTH: 192
<212> TYPE: PRT
<213> ORGANISM: Mus musculus

<400> SEQUENCE: 11

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Ser
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Tyr Glu Asn Val Arg Ala Lys
                85                  90                  95
```

```
Trp Phe Pro Glu Val Arg His His Cys Pro Ser Thr Pro Ile Ile Leu
            100                 105                 110

Val Gly Thr Lys Leu Asp Leu Arg Asp Asp Lys Asp Thr Ile Glu Lys
        115                 120                 125

Leu Lys Glu Lys Lys Leu Ala Pro Ile Thr Tyr Pro Gln Gly Leu Ala
    130                 135                 140

Leu Ala Lys Asp Ile Asp Ser Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Gln Pro Thr Arg Gln Gln Lys Arg Pro Cys Ser Leu Leu
            180                 185                 190
```

<210> SEQ ID NO 12
<211> LENGTH: 195
<212> TYPE: PRT
<213> ORGANISM: Caenorhabditis elegans

<400> SEQUENCE: 12

```
Met Gln Ala Ile Lys Cys Val Val Val Gly Asp Gly Ala Val Gly Lys
1               5                   10                  15

Thr Cys Leu Leu Leu Ser Tyr Thr Thr Asn Ala Phe Pro Gly Glu Tyr
            20                  25                  30

Ile Leu Thr Val Phe Asp Thr Tyr Ser Thr Asn Val Met Val Asp Gly
        35                  40                  45

Arg Pro Ile Asn Leu Ser Leu Trp Asp Thr Ala Gly Gln Asp Asp Tyr
    50                  55                  60

Asp Gln Phe Arg His Leu Ser Phe Pro Gln Thr Asp Val Phe Leu Val
65                  70                  75                  80

Cys Phe Ala Leu Asn Asn Pro Ala Ser Phe Glu Asn Val Arg Ala Lys
                85                  90                  95

Trp Tyr Pro Glu Val Ser His His Cys Pro Asn Thr Pro Ile Ile Leu
            100                 105                 110

Val Gly Thr Lys Ala Asp Leu Arg Glu Asp Arg Asp Thr Ile Glu Arg
        115                 120                 125

Leu Arg Glu Arg Arg Leu Gln Pro Val Ser His Thr Gln Gly Tyr Val
    130                 135                 140

Met Ala Lys Glu Ile Lys Ala Val Lys Tyr Leu Glu Cys Ser Ala Leu
145                 150                 155                 160

Thr Gln Ile Gly Leu Lys Gln Val Phe Asp Glu Ala Ile Arg Thr Gly
                165                 170                 175

Leu Thr Pro Pro Gln Thr Pro Gln Thr Arg Ala Lys Lys Ser Asn Cys
            180                 185                 190

Thr Val Leu
        195
```

<210> SEQ ID NO 13
<211> LENGTH: 192
<212> TYPE: PRT
<213> ORGANISM: Rattus norvegicus

<400> SEQUENCE: 13

```
Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30
```

```
Ile Pro Thr Val Phe Asp Asn Tyr Ser Ala Asn Val Met Val Asp Ser
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Tyr Glu Asn Val Arg Ala Lys
                85                  90                  95

Trp Phe Pro Glu Val Arg His His Cys Pro Ser Thr Pro Ile Ile Leu
            100                 105                 110

Val Gly Thr Lys Leu Asp Leu Arg Asp Asp Lys Asp Thr Ile Glu Lys
        115                 120                 125

Leu Lys Glu Lys Lys Leu Ala Pro Ile Thr Tyr Pro Gln Gly Leu Ala
    130                 135                 140

Leu Ala Lys Asp Ile Asp Ser Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Gln Pro Thr Arg Gln Gln Lys Arg Pro Cys Ser Leu Leu
            180                 185                 190


<210> SEQ ID NO 14
<211> LENGTH: 192
<212> TYPE: PRT
<213> ORGANISM: Danio rerio

<400> SEQUENCE: 14

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Ser
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Ser Thr Pro Ile Ile Leu
            100                 105                 110

Val Gly Thr Lys Leu Asp Leu Arg Asp Glu Lys Glu Thr Ile Glu Lys
        115                 120                 125

Leu Lys Glu Lys Lys Leu Ala Pro Ile Thr Tyr Pro Gln Gly Leu Ala
    130                 135                 140

Leu Ala Lys Glu Ile Asp Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Gln Pro Thr Lys Val Lys Lys Lys Gly Cys Val Met Leu
            180                 185                 190


<210> SEQ ID NO 15
<211> LENGTH: 192
<212> TYPE: PRT
<213> ORGANISM: Pan troglodytes
```

-continued

```
<400> SEQUENCE: 15

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Ser
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Tyr Glu Asn Val Arg Ala Lys
                85                  90                  95

Trp Phe Pro Glu Val Arg His His Cys Pro Ser Thr Pro Ile Ile Leu
            100                 105                 110

Val Gly Thr Lys Leu Asp Leu Arg Asp Asp Lys Asp Thr Ile Glu Lys
        115                 120                 125

Leu Lys Glu Lys Lys Leu Ala Pro Ile Thr Tyr Pro Gln Gly Leu Ala
    130                 135                 140

Leu Ala Lys Glu Ile Asp Ser Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Gln Pro Thr Arg Gln Gln Lys Arg Thr Cys Ser Leu Leu
            180                 185                 190
```

GENETICALLY ENGINEERED PHAGOCYTES, AND RELATED COMPOSITIONS, VECTORS, METHODS AND SYSTEMS

CROSS-REFERENCE TO RELATED APPLICATIONS

This application is a 371 of PCT/US2021/028972 filed Apr. 23, 2021, which claims priority to U.S. Provisional Application Nos. 63/126,379 filed Dec. 16, 2020, 2020; and 63/014,649, filed Apr. 23, 2020, which are incorporated herein by reference.

STATEMENT OF GOVERNMENT GRANT

This invention was made with government support under Grant No. GM046425 awarded by the National Institutes of Health. The government has certain rights in the invention.

INCORPORATION BY REFERENCE OF SEQUENCE LISTING PROVIDED AS A TEXT FILE

A Sequence Listing is provided herewith in a text file, "UCSB-548_SEQ_LIST.txt", created on Mar. 24, 2023 and having a size of 26,207 bytes. The contents of the text file are incorporated herein by reference in its entirety.

FIELD

The present disclosure generally relates to cell targeting in particular through phagocytosis and/or trogocytosis. More specifically, the present disclosure relates to genetically engineered phagocytes and related compositions, vectors, methods and systems.

BACKGROUND

Various methods and systems have been developed to target cells in a manner that results in death of the targeted cell.

Although progress has been made in connection with cell targeting, in particular, when associated with treatments of an individual, including chimeric antigen receptors (CARs) that reprogram T cells to kill cancer, challenges still remain for developing methods that result in efficient cell targeting in particular when associated to treatment of a disease.

SUMMARY

Provided herein are activated phagocyte and in particular engineered activated phagocytes and related vectors, compositions, methods and systems which in several embodiments allow efficient cell targeting through enhanced phagocytosis of target cells, which enables phagocytosis of live target cells.

In particular, provided herein are phagocytes including a naturally occurring or engineered active Rac gene, and/or expressing a naturally occurring or engineered Rac gene at activating Rac expression levels herein also indicated as an activated phagocyte. Activated phagocytes in the sense of the disclosure express Rac proteins in a configuration and/or at expression levels resulting in enhanced Rac properties. Enhanced Rac properties in the sense of the disclosure have been shown to enhance phagocytosis of the activated phagocyte to the extent of enabling engulfment and/or trogocytosis on living cells, as will be understood by a skilled person upon reading of the present disclosure.

According to a first aspect, a genetically engineered activated phagocyte is described. The genetically engineered activated phagocyte comprises an activated Rac gene encoding an activated Rac protein, the activated Rac gene is under the control of a first phagocyte promoter and a first additional phagocyte regulatory region. In the genetically engineered activated phagocyte, the activated Rac gene, the first phagocyte promoter and the first additional phagocyte regulatory regions are in a configuration allowing expression of the activated Rae gene in the activated phagocytic cell. In the genetically engineered activated phagocyte, at least one of the activated Rac gene, first phagocyte promoter and first additional phagocyte regulatory regions are heterologous with respect to the phagocyte.

In a genetically engineered activated phagocyte, herein described, the first phagocyte promoter controlling the Rac gene can be a constitutive or conditional promoter homologous or heterologous with respect to the phagocyte. In preferred embodiments, the genetically engineered activated phagocyte further comprises a chimeric antigen receptor (CAR) gene that is under the control of the first phagocyte promoter or a second phagocyte promoter and under the control of the first additional regulatory regions or second additional phagocyte regulatory regions in a configuration allowing for expression of the CAR in the activated phagocytic cell. The second phagocyte promoter and second additional phagocyte regulatory regions possibly controlling CAR expression can be the same or different from the first phagocyte promoter and first additional phagocyte regulatory regions controlling the activated Rac gene.

According to a second aspect, a genetically engineered activated phagocyte is described. The genetically engineered activated phagocyte comprises a Rac gene encoding a Rac protein, the Rac gene is under the control of a third phagocyte promoter and third additional phagocyte regulatory regions. In the genetically engineered activated phagocyte, the Rac gene, the third phagocyte promoter and the third additional phagocyte regulatory regions are in a configuration allowing for an expression of the Rac gene in the activated phagocytic cell at an elevated activating expression level compared to a wild-type or native phagocyte comprising the Rac gene.

In the genetically engineered activated phagocyte, at least one of the activated Rac gene, third phagocyte promoter and third additional phagocyte regulatory regions controlling the Rae gene, are heterologous with respect to the phagocyte.

In a genetically engineered activated phagocyte herein described, the third phagocyte promoter controlling the activated Rac gene can be a constitutive or conditional promoter and is typically heterologous with respect to the phagocyte. In preferred embodiments, the genetically engineered activated phagocyte further comprises a chimeric antigen receptor (CAR) under control of the third phagocyte promoter or a fourth phagocyte promoter and under control of the third regulatory region or fourth additional phagocyte regulatory regions in a configuration allowing expression of the CAR gene in the activated phagocytic cell. The fourth phagocyte promoter and fourth additional phagocyte regulatory regions controlling the CAR gene expression can be the same or different from the third phagocyte promoter and third additional phagocyte regulatory regions controlling the Rac gene.

According to a third aspect, a genetically engineered activated phagocyte is described. The genetically engineered activated phagocyte comprises a Rac genetic circuit, in which molecular components are connected one to another in accordance with a circuit design by activating, inhibiting, binding, or converting reactions to form a fully connected network of interacting components, wherein in the Rac genetic circuit expression of an activated Rac gene or an increased level of expression of a Rac gene occurs when the Rac genetic circuit operates according to the circuit design in response to a trigger molecular component within the activated phagocyte.

According to a fourth aspect a genetically engineered activated phagocyte is described. The genetically engineered activated phagocyte is a naturally occurring active phagocyte expressing a naturally occurring active Rac gene tinder control of a first promoter and first additional regulatory regions, and further comprising a chimeric antigen receptor (CAR) under the control of a second phagocyte promoter and under the control of second additional phagocyte regulatory regions. In the genetically engineered activated phagocyte, the chimeric antigen receptor, the second phagocyte promoter and the second additional phagocyte regulatory regions are in a configuration allowing for expression of the CAR in combination with expression of a naturally occurring active Rac gene in the genetically engineered activated phagocyte.

According to a fifth aspect, a Rac expression vector is described. The active Rae expression vector comprising an activated Rac gene encoding for an activated Rac protein, the gene under control of a first phagocyte promoter and of first additional phagocyte regulatory regions in a configuration allowing expression of the activated Rac gene in a phagocyte. Preferably, the vector further comprises a chimeric antigen receptor (CAR) gene under control of the first phagocyte promoter or a second phagocyte promoter and of the first additional regulatory regions or second additional phagocyte regulatory regions in a configuration allowing expression of the CAR in the activated phagocytic cell. In addition or in the alternative, the Rac expression vector can include a Rac gene under control of a third phagocyte promoter and of third additional phagocyte regulatory regions in a configuration allowing an expression of the activated Rac gene in the activated phagocytic cell at an elevated activating expression level. The third phagocyte promoter and controlling the Rac gene resulting in the elevate expression of the Rac gene can be the sane or different from the first phagocyte promoter and the second phagocyte promoter. The third additional phagocyte regulatory regions can be the same or different from the first additional phagocyte regulatory regions controlling the Rac gene and the second additional regulatory regions controlling expression of the CAR gene.

According to a sixth aspect, a method and system are described to provide a genetically engineered activated phagocytic cell herein described. The method comprises introducing into a phagocytic cell an activated Rac gene herein described, under control of a first phagocyte promoter and of additional first phagocyte regulatory regions in a configuration allowing expression of the activated Rac gene in the phagocyte.

In addition, or in the alternative the method can comprise introducing into the phagocytic cell a Rac gene, a third phagocyte promoter and a third additional phagocyte regulatory region in a configuration allowing an expression of the activated Rac gene in the activated phagocytic cell at an activated expression level.

In addition, or in the alternative the method can comprise introducing into the phagocytic cell molecular components a Rac genetic circuit herein described in a configuration allowing expression of an activated Rac gene or an increased level of expression of a Rac gene occurs when the Rac genetic circuit operates according to the circuit design in response to a trigger molecular component within the phagocytic cell.

In addition, or in the alternative when the phagocyte is a naturally occurring active phagocyte herein described, the method can further comprise introducing into a phagocytic cell a chimeric antigen receptor (CAR) under control of a second phagocyte promoter and optionally under control of second additional phagocyte regulatory regions.

The system comprises a combination of a phagocyte, a naturally occurring active phagocyte herein described, a Rac expression vector herein described and a CAR expression vector comprising a chimeric antigen receptor (CAR) under control of a second phagocyte promoter and optionally under control of a second additional phagocyte regulatory regions in a configuration allowing expression of the CAR in the phagocytic cell and/or in the activated phagocytic cell.

According to a seventh aspect, a Rac active composition is described, the Rac active composition comprises a naturally occurring active phagocyte herein described, the genetically engineered activated phagocyte herein described, the Rae, expression vectors herein described and/or the CAR expression vector herein described, together with an acceptable carrier in an effective amount for use to obtain engulfment and/or trogocytosis of a target cell.

In some embodiments the composition is a pharmaceutical composition and the naturally occurring active phagocyte herein described, the genetically engineered activated phagocyte herein described, the Rac expression vectors herein described and/or the CAR expression vector herein described are comprised in the pharmaceutical composition in an effective amount for use in a method to treat an individual by engulfment and/or trogocytosis of a target cell.

According to an eighth aspect, a method of treating an individual is described by engulfment and/or trogocytosis of a target cell. The method comprises administering to the individual a therapeutically effective amount of a Rac active pharmaceutical composition herein described.

According to a ninth aspect, a method of treating a tumor in an individual is described, the method comprising administering to the individual a therapeutically effective amount of a pharmaceutical composition comprising an activated phagocyte in the sense of the disclosure which, in some embodiments, can be a genetically engineered activated phagocyte herein described.

According to a tenth aspect, a method of treating Alzheimer's Disease in an individual is described, the method comprising administering to the individual a therapeutically effective amount of a pharmaceutical composition comprising an activated phagocyte in the sense of the disclosure which, in some embodiments, can be a genetically engineered activated phagocyte herein described and/or one or more Rac2 activated vectors (e.g. viral or RNA-protein particles and RNA-lipid particles) configured to directly target macrophages of the individual and to provide upon transfection and expression of the Rac gene in the vector, macrophages of the individual which are activated in the sense of the present disclosure. In particular, in embodiments herein described administration of one or more activated phagocytes and/or one or more Rac expression vector herein described is performed to trigger phagocytosis of amyloid-beta in the individual. Accordingly, methods and systems of treating Alzheimer's Disease in an individual herein described are expected to result in reduction and possibly a clearance of amyloid-beta plaque of the individual as will be understood by a skilled person.

Activated phagocytes, vectors, compositions and related methods and systems herein described can be used in various applications alone and/or in combination with additional agents to kill and/or eliminate live cells in vitro, in vivo and/or ex vivo. In particular, killing and/or elimination of live cells can be perforated for therapeutic purposes or other purposes identifiable by a skilled person.

The phagocytes, vectors, compositions and related methods and systems herein described have shown in some embodiments that expression of an activating mutation in the human Rac2 gene in a macrophage can activate the macrophage to consume and/or kill cancerous white blood cells.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue.

In particular, the activated phagocytes, vectors, compositions and related methods and systems herein described in several embodiments, can provide not only a target-specific therapeutic effect directed against target cells that specifically bind the antigen binding domain of the CAR, but also vastly improve anti-tumor therapeutic efficacy in reducing tumor cells and amelioration of various physiological symptoms associated with the cancerous condition.

The activated phagocytes, vectors, compositions and related methods and systems herein described in several embodiments are can be effective against antibiotic resistant and phagocytosis-resistant bacterial infections, as well as enhancing vaccine effectiveness against viral infections, such as COVID 19 and additional viruses identifiable by a skilled person.

The phagocytes, vectors, compositions and related methods and systems herein described can be used in connection with various applications wherein engulfment and/or trogocytosis of a target cell are desired. For example, the phagocytes, vectors, compositions and related methods and systems herein described can be used in drug research and/or to develop diagnostic and therapeutic approaches and/or tools to counteract diseases such as tumors and Alzheimer's disease. Additional exemplary applications include uses of the activated phagocytes, vectors, compositions and related methods and systems herein described in several fields including basic biology research, applied biology, bio-engineering, etiology, medical research, medical diagnostics, therapeutics, and in additional fields identifiable by a skilled person upon reading of the present disclosure.

The details of one or more embodiments of the disclosure are set forth in the accompanying Appendices and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein.

Figure 1A:
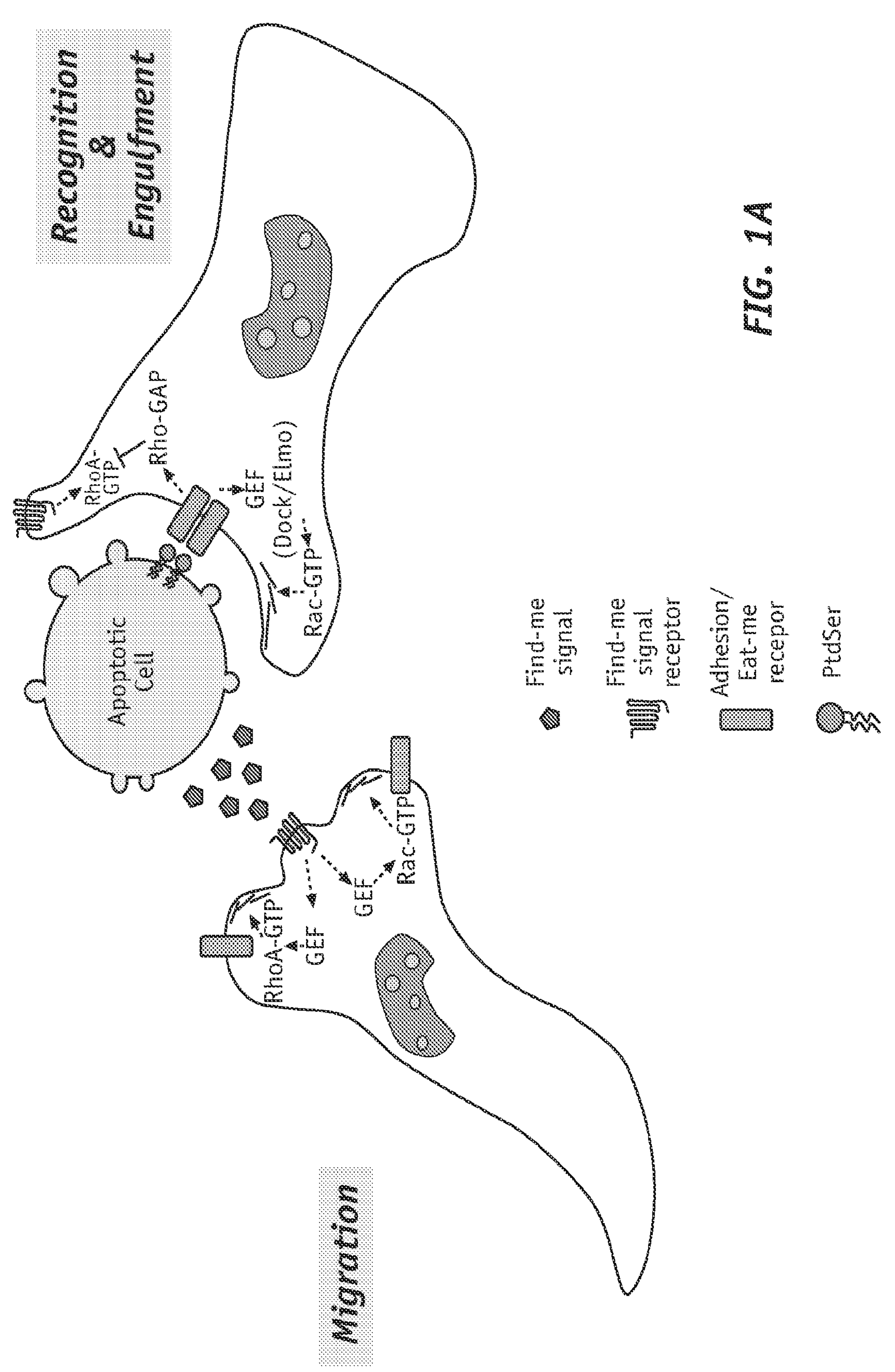
FIGS. 1A to 1E show a schematic illustration (FIG. 1A) from Elliott and Ravichandran, 2016, (Elliott and Ravichandran 2016) and images showing morphology after abnormal GTPase over-activation, in particular, Serum-starved cell cluster with 6-10 3T3 Fibroblast (FIG. 1B) Rac Branched actin polymerization Lamellipodia formation (FIG. 1C) Cdc42Linear actin polymerization Filopodia formation (FIG. 1D), Rho Actomyosin contractility Stress fiber formation (FIG. 1E), from Hall, 1998 (Hall 1998).
Figure 1F:
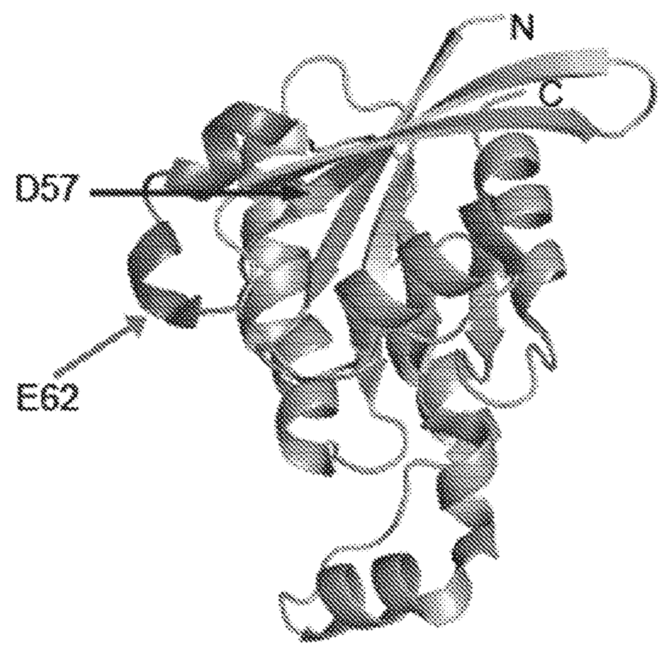
FIGS. 1F to 1K show conserved sequences and structure among Rac1, Rac2 and Rac3 proteins and among different individuals.

In particular, in FIG. 1F, show the tertiary structure of the RAC1 (3TH5) in a three-dimensional representation from (Hsu et al. 2019), showing key residues D57 and E62.

Figure 1G:
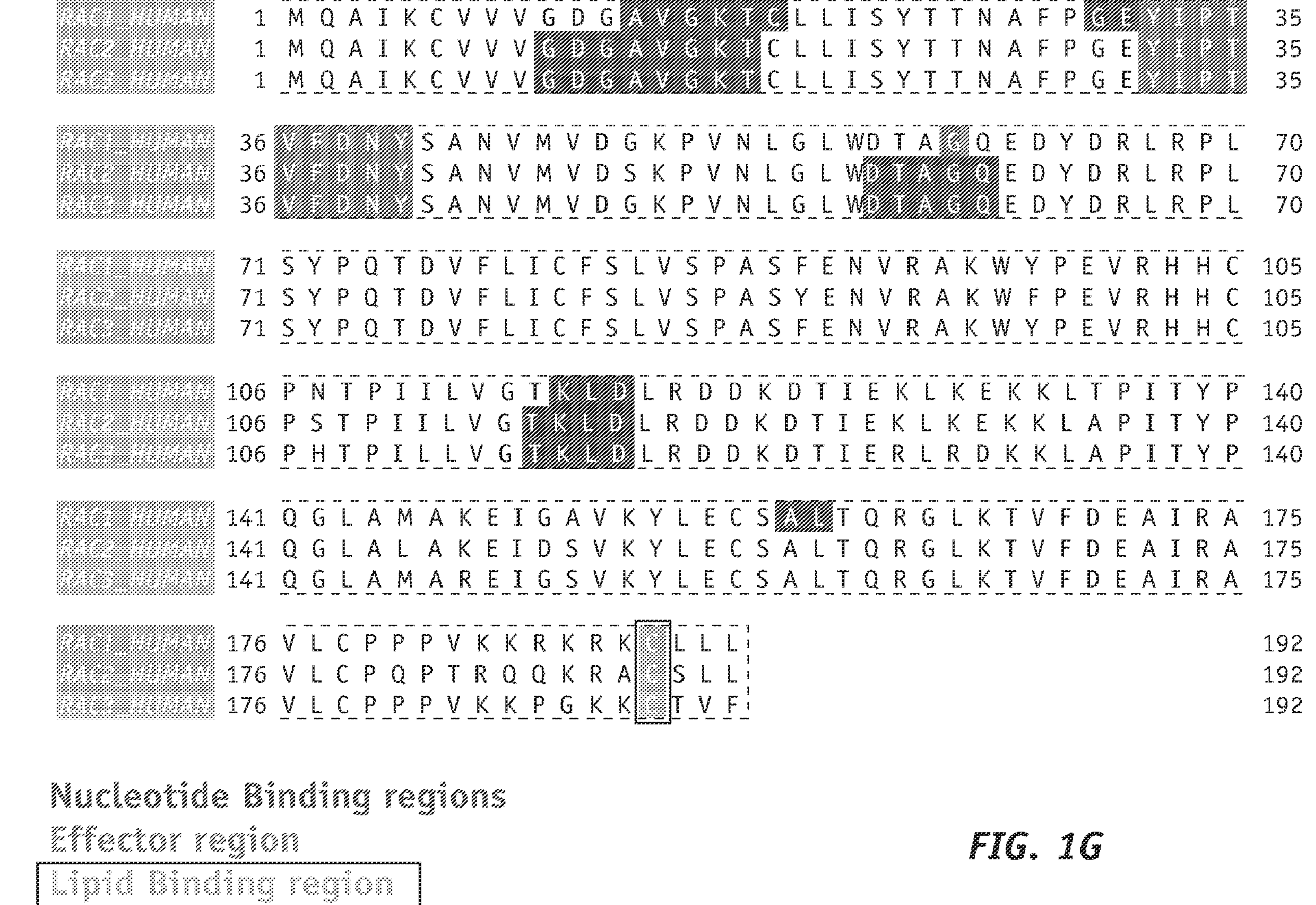

FIG. 1G shows a sequence alignment between sequences of Rac1, Rac2 and Rac3 proteins in humans prepared using Jalview software, further showing the nucleotide binding region (black highlight), Effector region (gray highlight) and Lipid binding region (light gray highlight boxed).

Figure 1H:
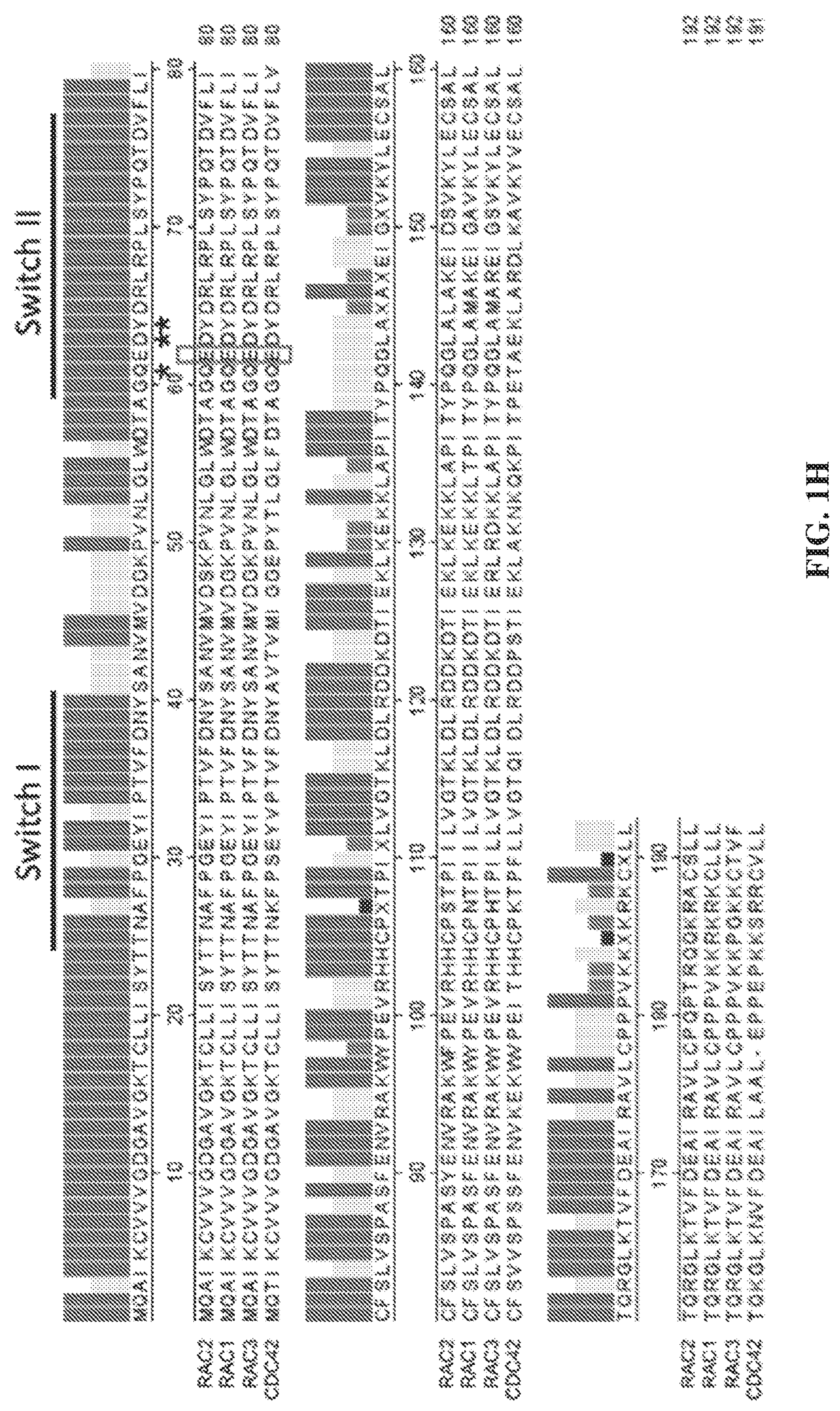
Figure 11:
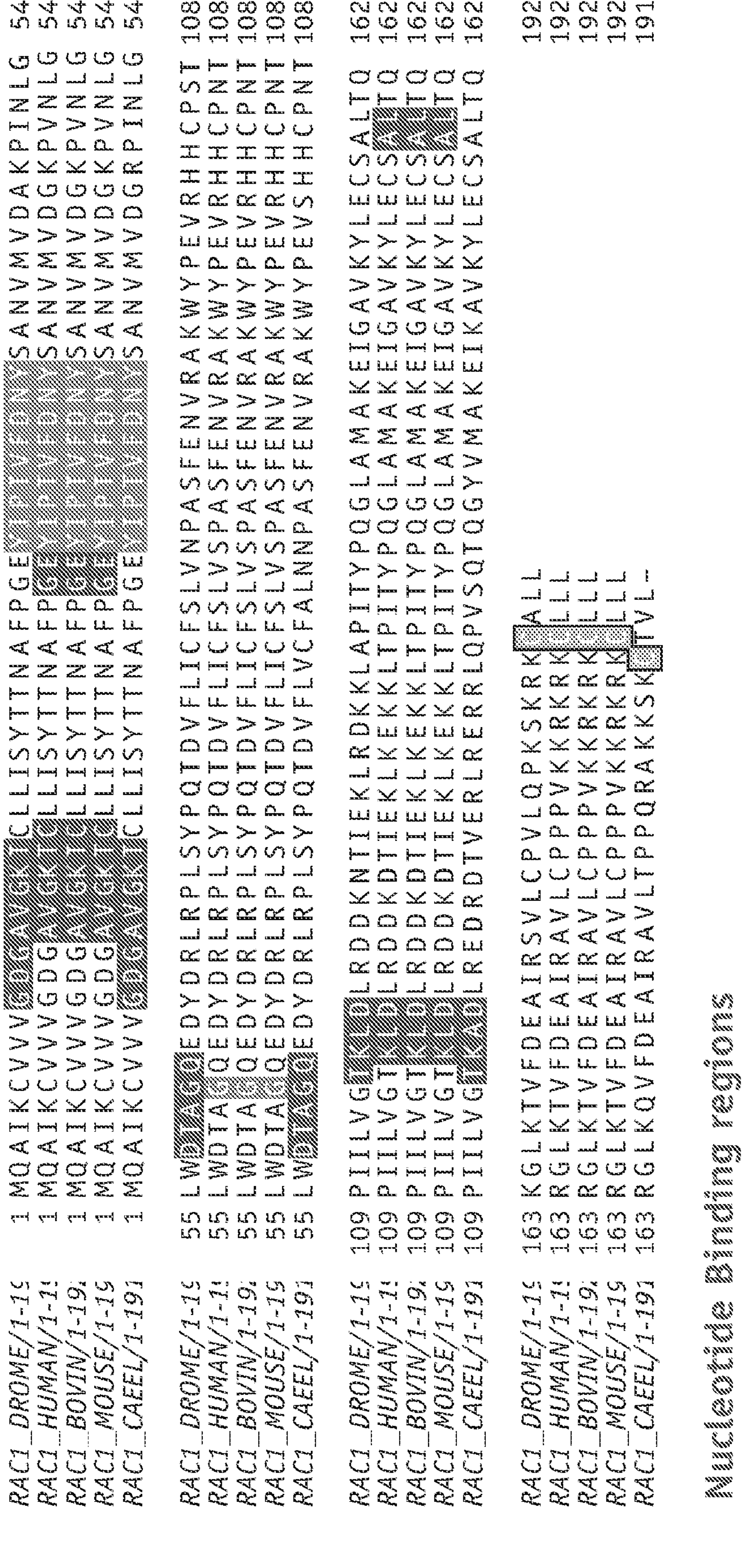

FIG. 1H shows an exemplary sequence alignment for Rac1, Rac2, Rac3 and CDC42 protein human RHO family GTPases further showing Conserved Switch I, Switch II regions and open box, E62; *Q61, D63, and Y64 are highlighted. Protein sequences (RAC2 NP_002863.1, RAC1 NP_008839.2, RAC3 NP_005043.1, CDC42 NP_001782.1) are from the National Center for Biotechnology Information (NCBI) (Hsu et al. 2019).

FIG. 1I shows an exemplary sequence alignment prepared using Jalview software between Rac1 proteins of exemplary individuals (drosophila, human, bovine, mouse and *Caenorhabditis elegans*) further showing the nucleotide binding region (black highlight), Effector region (gray highlight) and Lipid binding region (light gray highlight boxed).

FIG. 1J shows an exemplary sequence alignment between Rac2 proteins of exemplary individuals (drosophila, human, bovine, mouse and *Caenorhabditis elegans*) further showing the nucleotide binding region (black highlight), Effector region (gray highlight) and Lipid binding region (light gray highlight boxed).

FIG. 1K shows a schematic representation of Rac2 from (Lougaris et al. 2019) showing Switch I, Switch II and C terminal regions and location of a P34H replacement (upper panel) as well as a sequence alignment in various individuals of the Switch I region showing location of the P34H and resulting sequence.

Figure 1L:
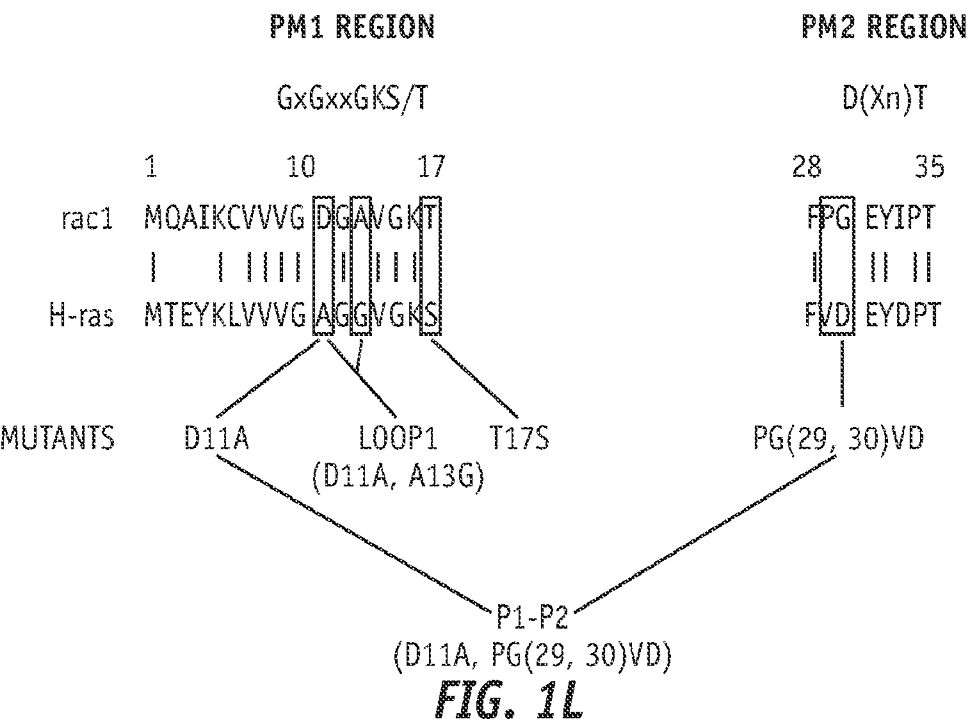

FIG. 1L shows a sequence alignment of Rac1 and H-ras in the phosphate magnesium binding (PM) regions. Identical amino acids are linked by vertical lines. Mutated amino acids are boxed. X indicates any amino acids, from (Menard and Snyderman, 1993).

Figure 1M:
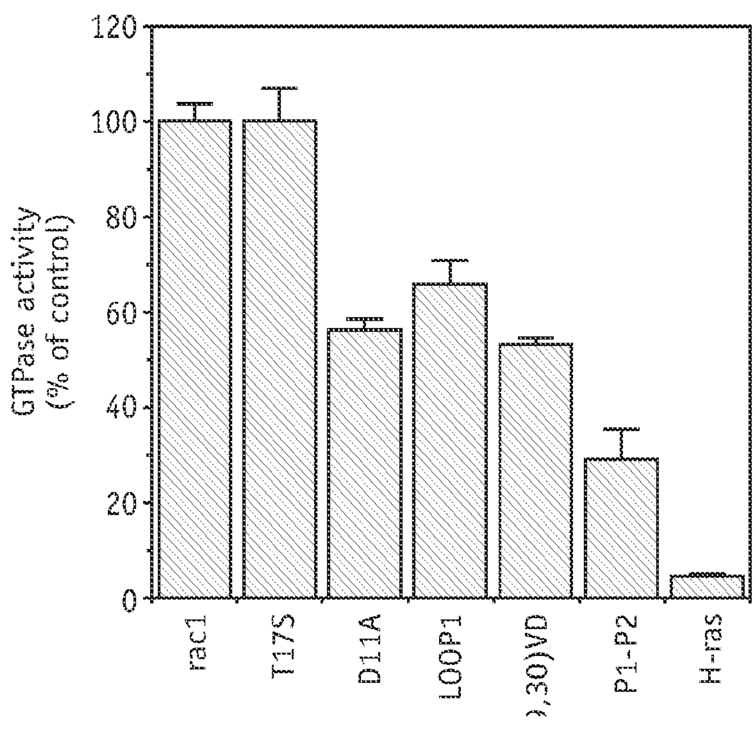

FIG. 1M shows a chart showing GTPase activity of Rac1, H-ras and related mutants from the sequence alignment of FIG. 1L from (Menard and Snydernan, 1993).

Figure 2A:
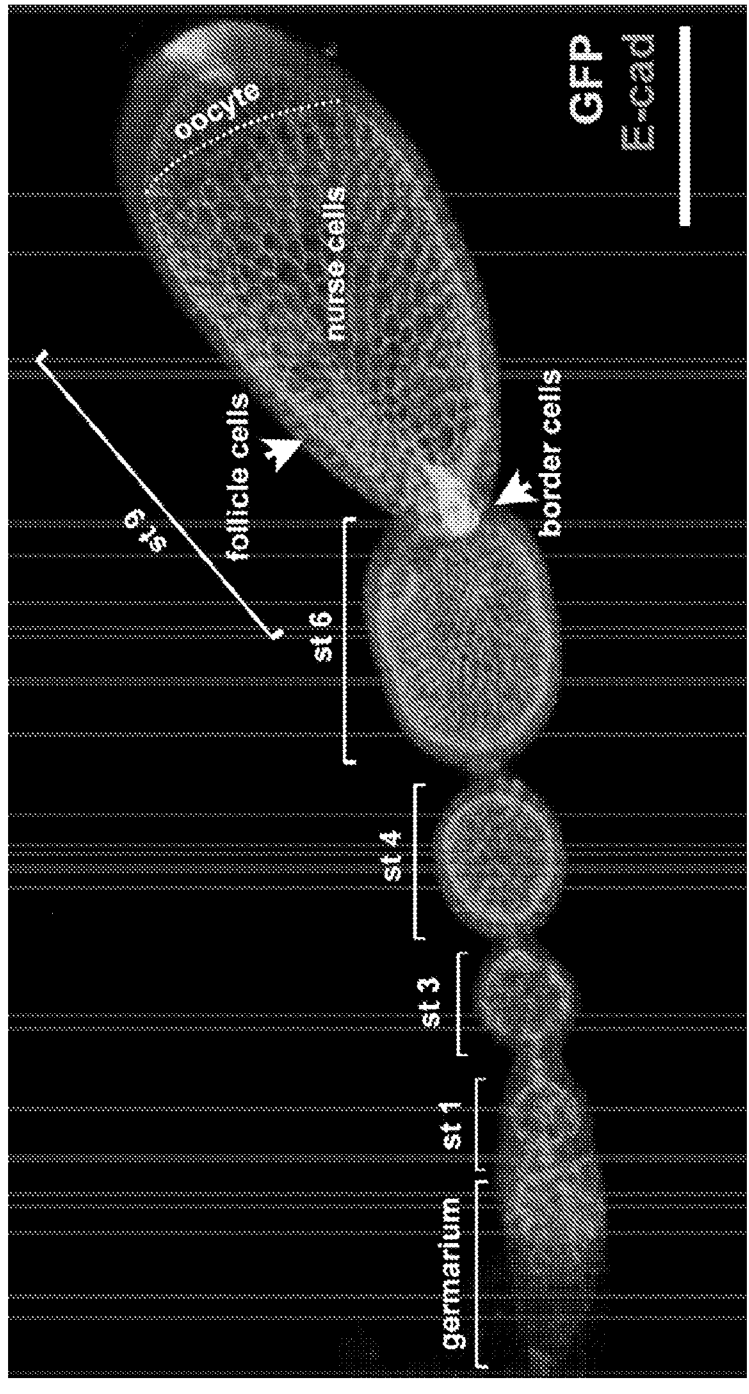

FIGS. 2A-2T show images illustrating an exemplary expression of constitutively active Rac (Rac-CA) in a subset of follicle cells causing wholesale tissue destruction and engulfment of other follicle cells. Border cells (b) and polar cells (p) are marked. Refer to supplementary movies 3 and 4 for a plane-by-plane section for in-depth visualization. All images oriented anterior on left, posterior on right. Scale bars are 50 μm, except in FIGS. 2D, 2F, 2G, 2P-2Q, 2S-2T (20 μm).

In particular, FIG. 2A shows an image of a drosophila ovariole containing developing egg chambers is shown. Border cells (arrow) and posterior follicle cells expressing PLCd1-PH-GFP driven by a slbo enhancer in stage 9 egg chamber are labeled. Follicle cells (arrow) express E-cad (grey) and Hoechst labels the nuclei. Nurse cell nuclei (arrow) are bigger than somatic follicle cells.

Figure 2B:
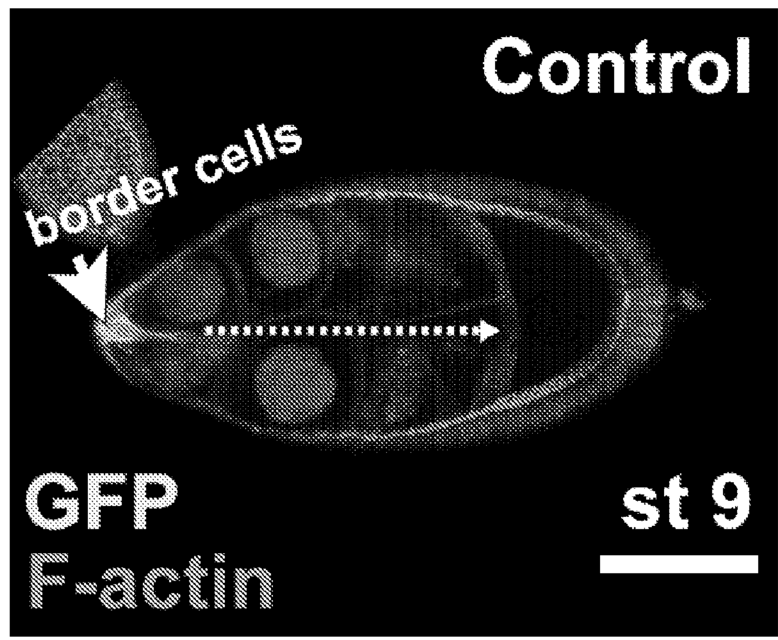
Figure 2C:
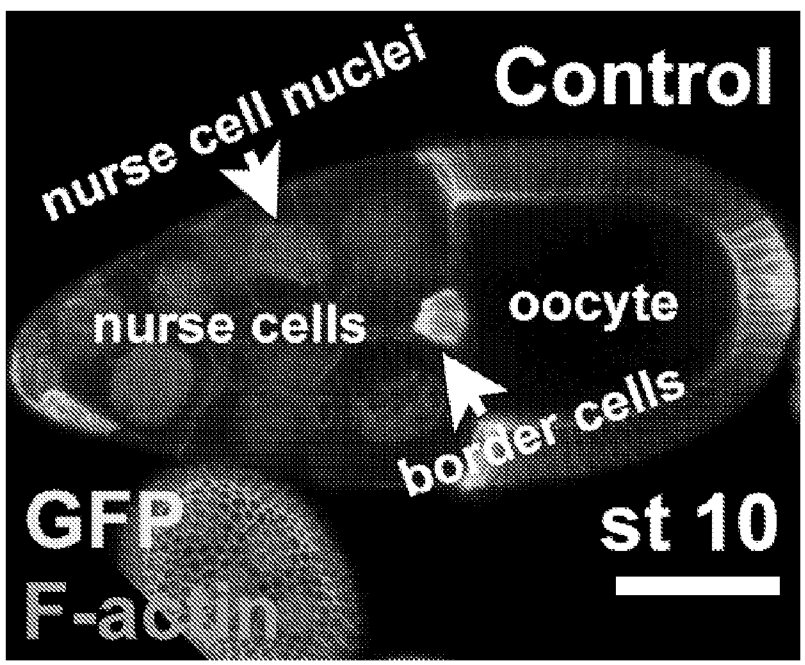
Figure 2D:
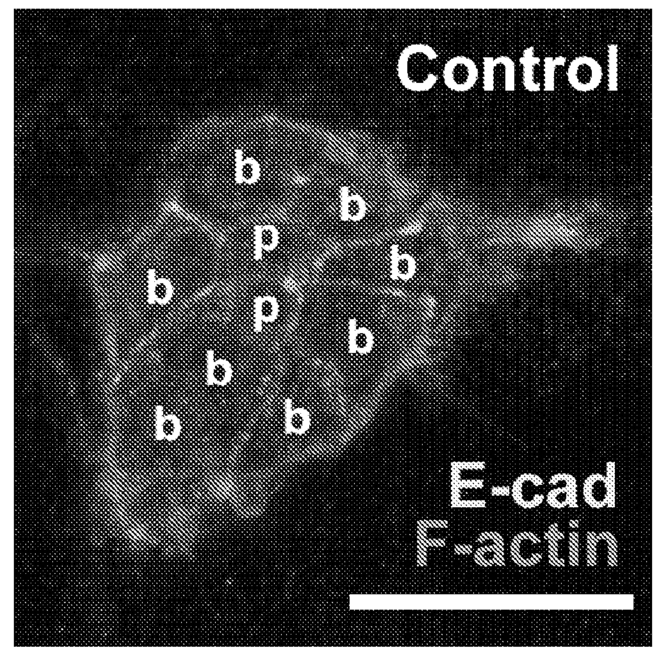
Figure 2E:
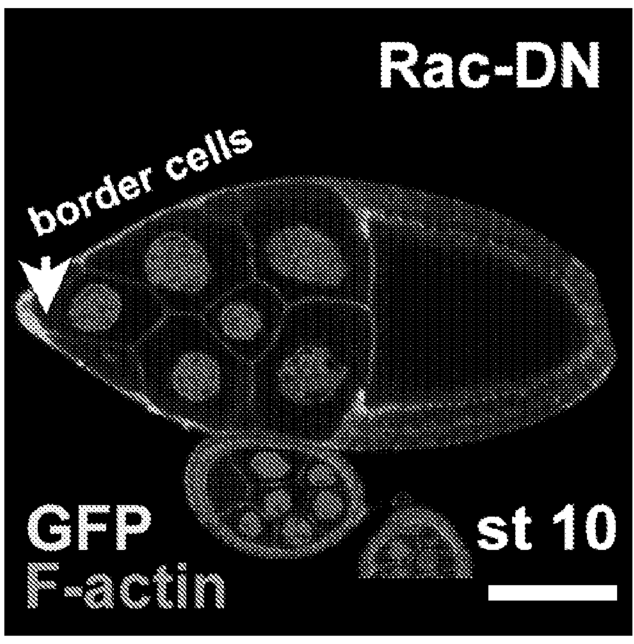
Figure 2F:
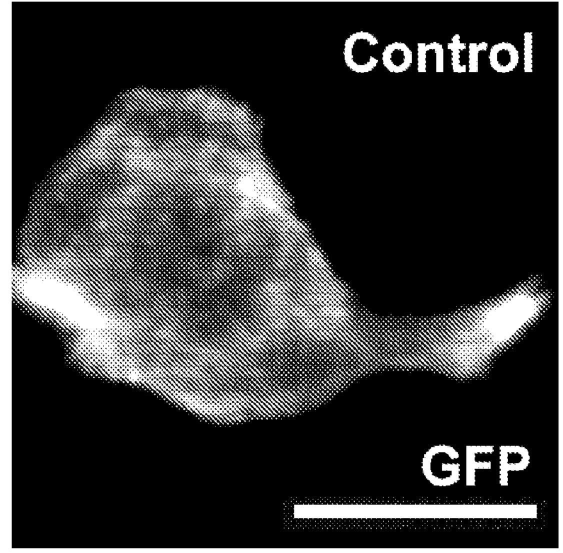
Figure 2G:
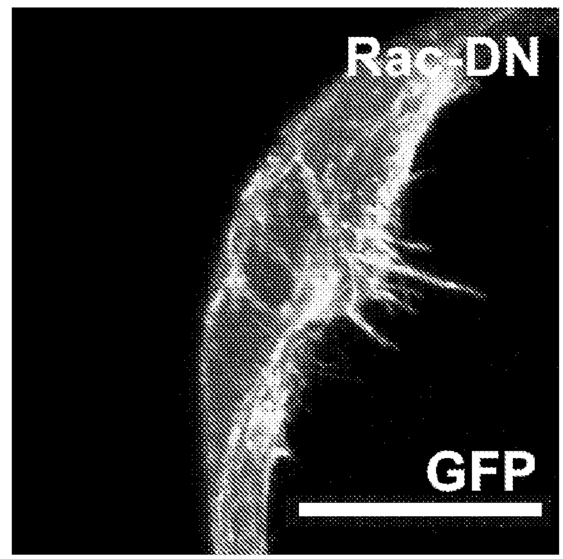
Figure 2H:
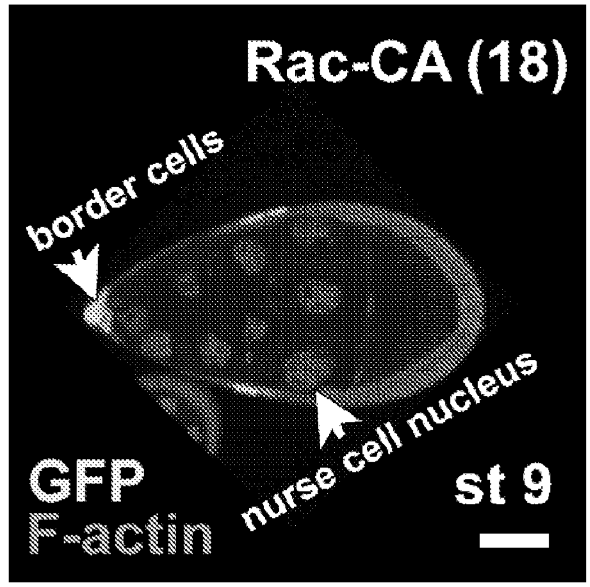
Figure 2I:
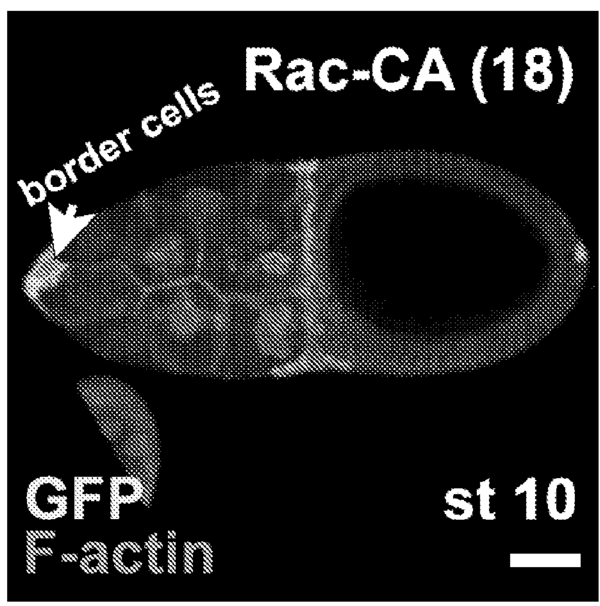

FIG. 2I an image of an exemplary stage 9 egg chamber expressing PLCd1-PH-GFP driven by a slbo enhancer (green) showing initiation of border cell migration (arrow). The migration path is indicated by dashed arrow.

FIG. 2C an image of an exemplary stage 10 egg chamber at the completion of border cell migration (arrow). Oocyte and nurse cells are marked. GFP (white), F-actin (grey, labeled by phalloidin) are labeled.

FIG. 2D an image of an exemplary high magnification image of a border cell cluster. The border cell cluster carries 6-10 border cells (b) surrounding a pair of non-motile polar cells (p). E-cad (white) is enriched at the border cell-border cell, border cell-polar cell and polar cell-polar cell contacts. F-actin (grey, labeled by phalloidin) constitute a supracellular cortical actin network.

FIG. 2E an image of an exemplary stage 10 egg chamber expressing PLCd1-PH-GFP and UAS-Rac1N17 (Rac-DN) driven by a slbo enhancer (white) showing failure of border cell migration (arrow).

FIG. 2F a high magnification image of an exemplary slbo-Gal4-LAS-Lifeact-GFP; UAS-lacZ border cell cluster has an actin rich protrusion whereas FIG. 2G shows a slbo-Gal4-LAS-Lifeact-GFP; UAS-Rac1N17 cluster devoid of protrusions. GFP (grey) is labeled by anti-GFP antibody.

FIG. 2H shows an image of an exemplary stage 9 egg chamber of a slbo-Gal4-UAS-Lifeact-GFP, UAS-Rac-V12 (Rac-CA) fly reared at 18° C. Border cell cluster is indicated (arrow).

FIG. 2I shows an image of an exemplary stage 10 egg chamber of a slbo-Gal4-UAS-Lifeact-GFP, UAS-RacV12 fly reared at 18° C. shows failure of border cell migration (arrow).

Figure 2J:
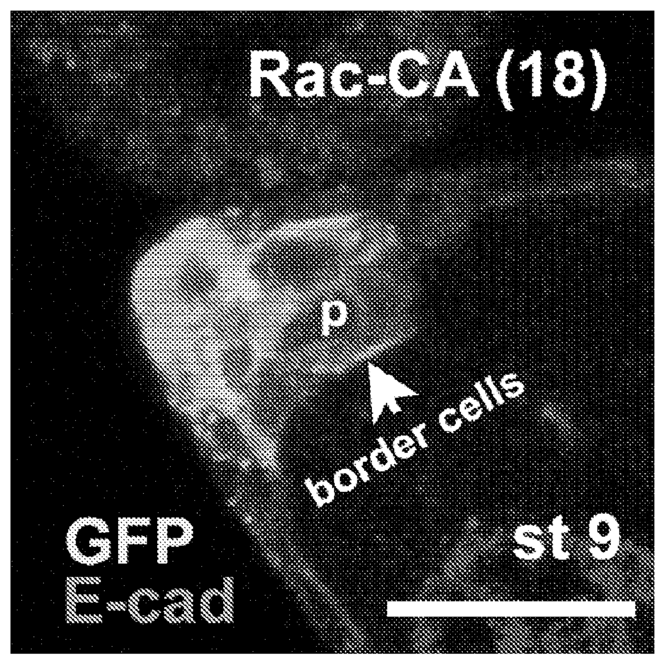

FIG. 2J shows a high magnification image of an exemplary stage 9 egg chamber from slbo-Gal4-UAS-Lifeact-GFP, UAS-RacV12 fly reared at 18° C. displays a non Rac1V12 expressing polar cell inside of a border cell (arrow). GFP (white), F-actin (grey, labeled by phalloidin) and Hoechst are labeled.

Figure 2K:
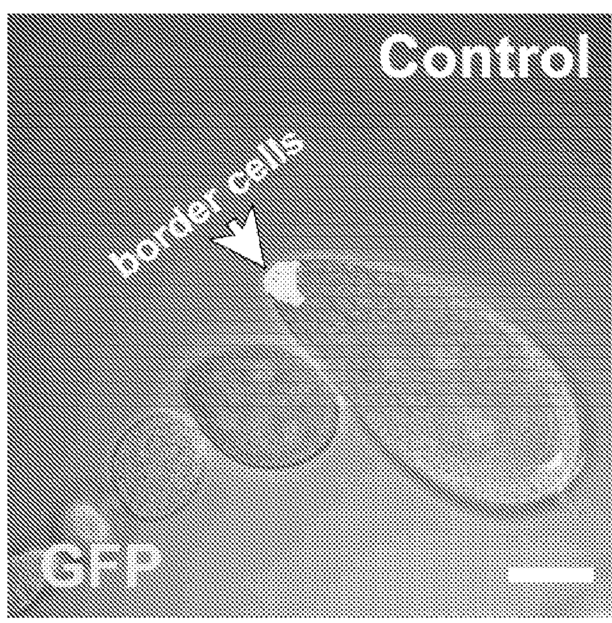
Figure 2L:
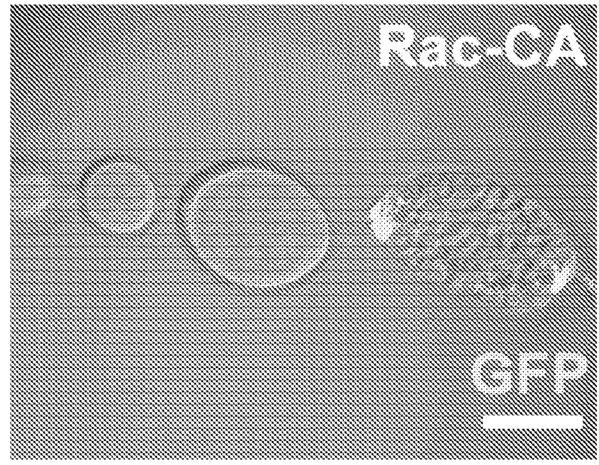

FIG. 2K shows an image of an exemplary a Lifeact-GFP and lacZ driven by a slbo enhancer (green) in control stage 9 egg chamber and FIG. 2L shows a degenerating Rac-CA expressing egg chamber.

Figure 2M:
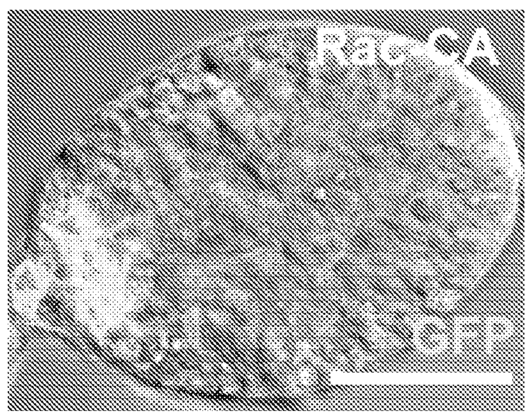

FIG. 2M shows a high magnification image of an exemplary Rac-CA expressing egg chamber (slbo-LifeactGFP, white) showing tissue destruction.

Figure 2N:
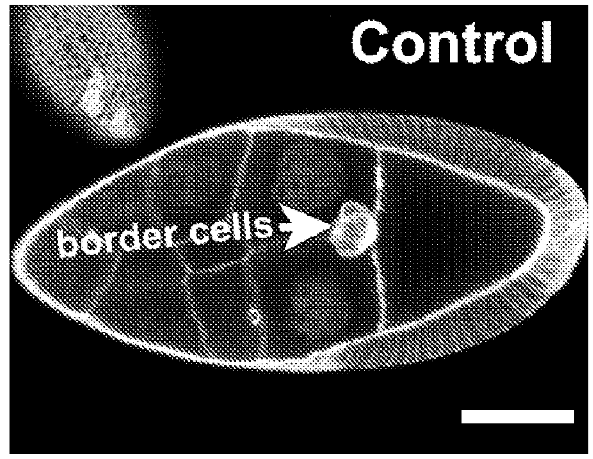

FIG. 2N shows an image of an exemplary control stage 9 egg chamber expressing PLCd1-PH-GFP and lacZ driven by a slbo enhancer.

Figure 2O:
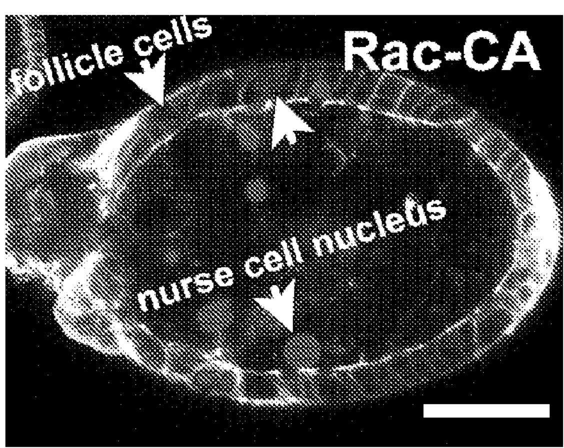

FIG. 2O shows an image of an exemplary Rac-CA showing dead nurse cells engulfed by follicle cells (arrows).

Figure 2P:
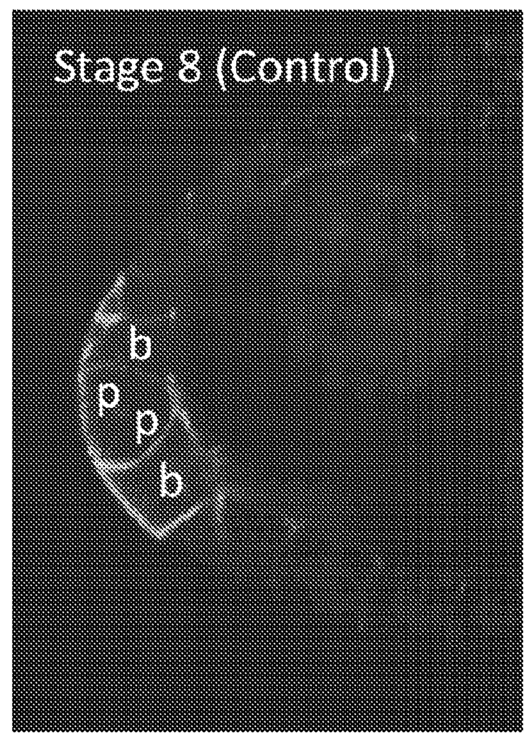

FIG. 2P shows a high magnification of the anterior end of an exemplary control stage 8 slbo-Gal4-UAS-lacZ egg chamber.

Figure 2Q:
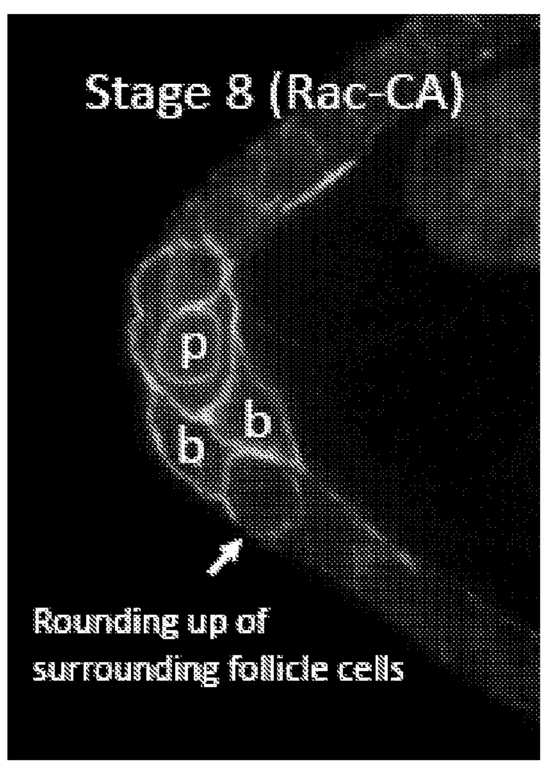

FIG. 2Q shows a high magnification image of the anterior end of a stage 8 slbo-Gal4-UAS-Rac1V12 egg chamber. Anterior follicle cells take bites of either polar cells (p) or nearby follicle cells (white arrows) that do not express Rac-CA.

FIG. 2R shows a chart reporting an exemplary detected quantification of percentage of egg chambers with follicle cell engulfment. Statistics represents unpaired t-test and ** is p<0.01.

FIGS. 2S and 2T show images of exemplary Flpout clones expressing either control lacZ (FIG. 2S) or Rac-CA (FIG. 2T) in a subset of border and polar cells are labeled by GFP (grey). In control clones, border cells (solid lines) and polar cells (dashed lines) are demarcated. Clonal border cells (solid lines) for Rac-CA (FIG. 2T) engulf the non-clonal polar cells (dashed lines) displaying a 'cell-in-cell' phenotype.

Figure 3E:
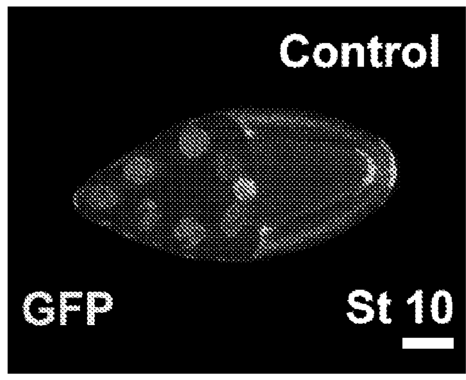
Figure 3F:
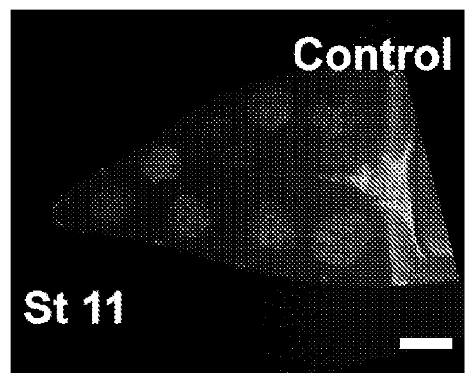
Figure 3G:
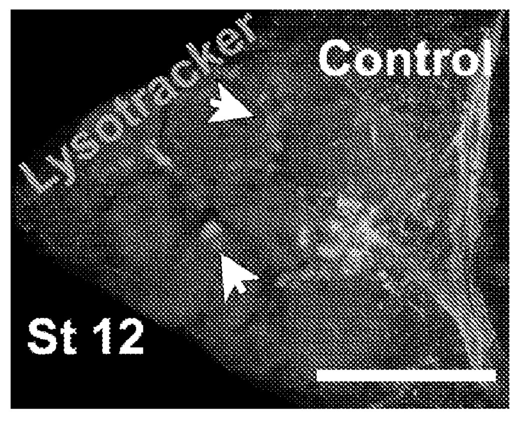
Figure 3H:
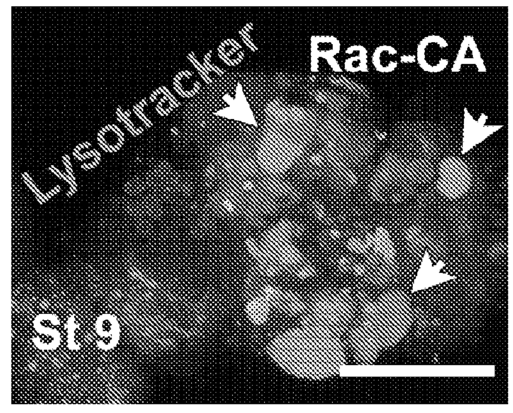
Figure 3I:
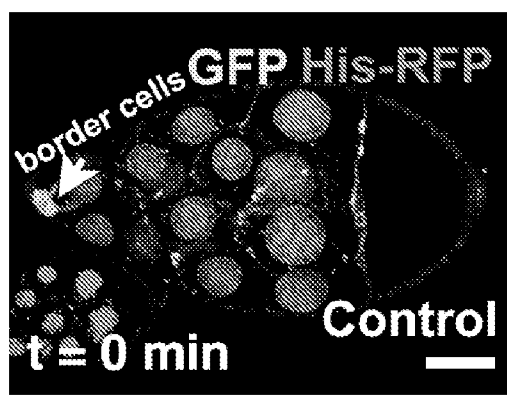
Figure 3J:
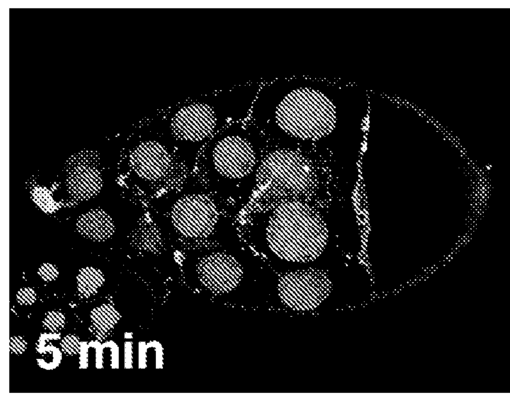
Figure 3K:
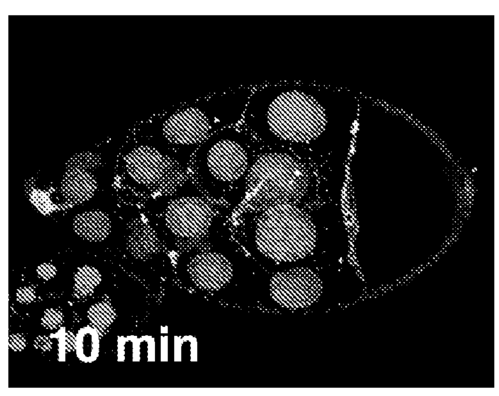
Figure 3L:
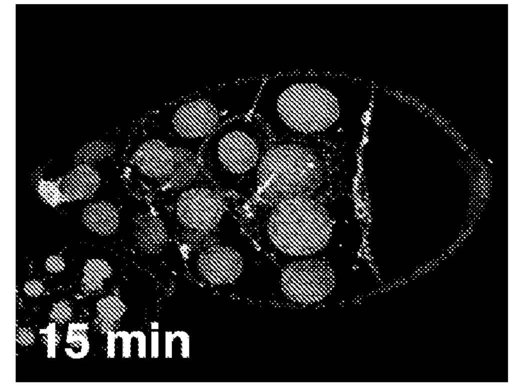
Figure 3M:
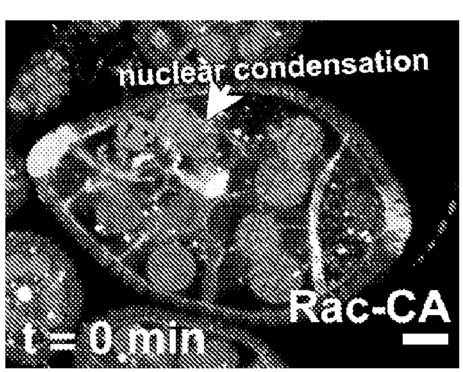
Figure 3N:
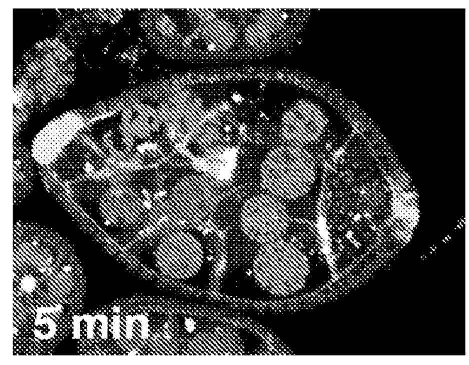
Figure 3O:
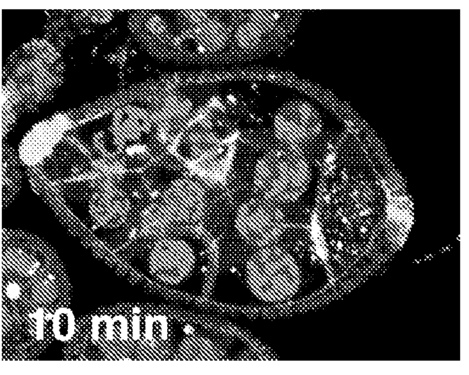
Figure 3P:
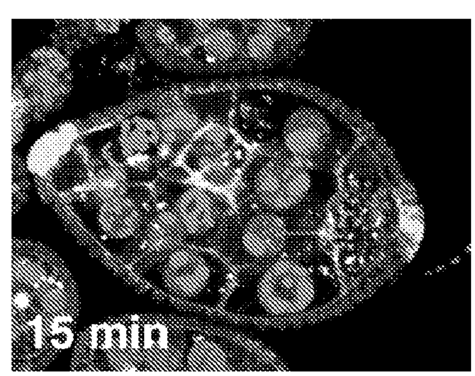

FIGS. 3A-3P shows images illustrating an exemplary constitutively active Rac in a subset of follicle cells initiating caspase mediated follicle cell death and lysosome dependent germline nurse cell death. Scale bars are 50 μm.

In particular, FIGS. 3A-3D show images of exemplary Flpout clones expressing either control lacZ (FIG. 3A) or Rac-CA (FIGS. 3B, 3C, 3D) in a subset of follicle cells are labeled by GFP antibody (white), Dcp-1 (grey, *Drosophila* death caspase). Control egg chambers (FIG. 3A) display no Dcp-1 staining whereas Rac-CA expressing egg chambers show non-autonomous accumulation of Dcp-1 in early stage egg chambers (arrows) (FIG. 3B). FIG. 3C shows a high magnification image of stage 7 egg chamber expressing Rac-CA displaying non-autonomous Dcp-1 activation in nearby follicle cells (arrows). FIG. 3D shows a Stage 9 egg chamber expressing Rac-CA clonally display a long range Dcp-1 activation in follicle cells (arrows) not in the immediate vicinity of clonal follicle cells suggesting that the long range Dcp-1 activation in follicle cells may cause wholesale tissue destruction. GFP labeled clones are marked by dashed lines in FIGS. 3B, 3C, 3D. Germline nurse cells do not display any Dcp-1 either in control or Rac-CA expressing clones.

FIGS. 3E-3H show images showing exemplary Lifeact-GFP and lacZ driven by a slbo enhancer (white) in control stage 10, 11, 12 egg chambers (FIGS. 3E, 3F, 3G) and Rac-CA expressing egg chamber (FIG. 3H) are shown. Lysotracker is marked by arrows. Lysotracker begin to enrich in the acidic compartments of stretch follicle cells surrounding germline nurse cells in stage 12 in control egg chambers leading to nurse cell permeabilization and lysosome mediated death during later stages of egg chamber development (Timmons et al, 2016). Rac-CA expressing egg chamber (FIG. 3H) display premature Lysotracker enrichment in nurse cell nuclei (arrows) suggesting early onset of nurse cell permeabilization in these egg chambers. The smaller follicle cell nuclei do not have any Lysotracker enrichment.

FIGS. 3I-3P show images showing exemplary stills from time-lapse images of egg chambers driven by a slbo enhancer (in border cells) in control lacZ (FIGS. 3I, 3J, 3K, 3L) and Rac-CA (FIGS. 3M, 3N, 3O, 3P). ubi-HisRFP (grey) labels all nuclei. All nurse cell nuclei begin to condense synchronously within minutes after the expression of Rac-CA (FIGS. 3M, 3N, 3O, 3P) as opposed to control.

Figure 4A:
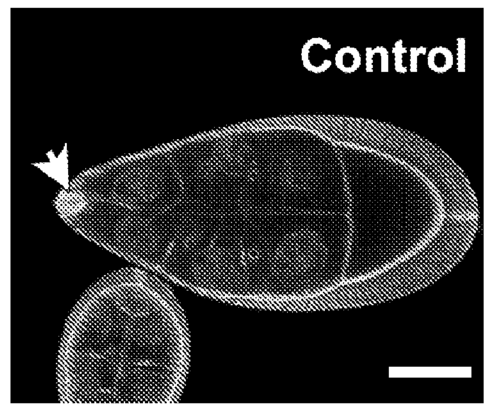

FIGS. 4A to 4N show images and charts illustrating how a loss-of-function of *Drosophila* engulfment receptor Draper rescue the germline nurse cell death, but not the follicle cell engulfment, caused by Rac-CA.

Figure 4B:
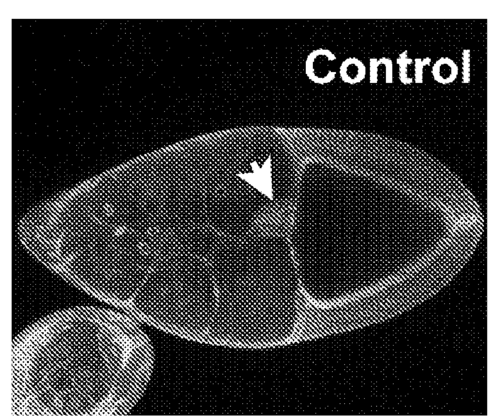

In particular FIGS. 4A and 4B is an image showing exemplary stage 9 egg 9 FIG. 4A) and stage 10 egg (FIG. 4B) chambers expressing lacZ driven by a slbo enhancer.

Figure 4C:
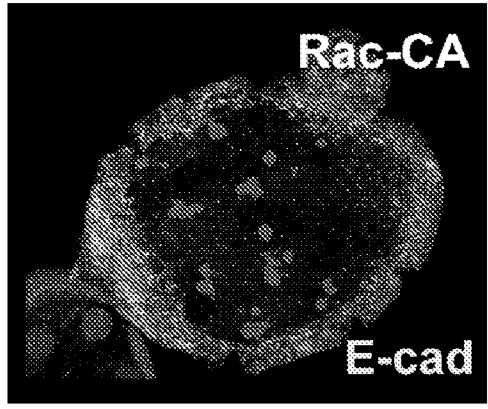

FIG. 4C is an image showing an exemplary expression of Rac-CA causes entire egg chamber degeneration.

Figure 4D:
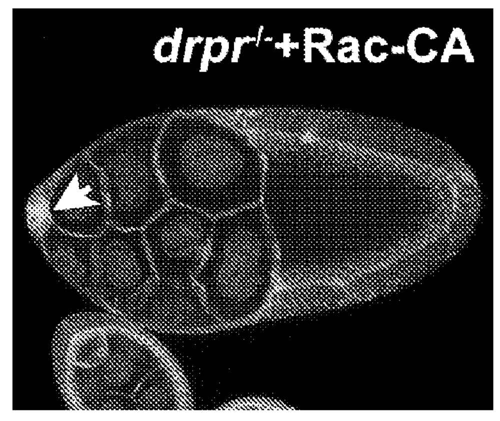

FIG. 4D is an image showing an exemplary expression of Rac-CA in draper homozygous background rescuing the germline nurse cell death. Border follicle cells do not protrude and initiate migration (arrow).

Figure 4E:
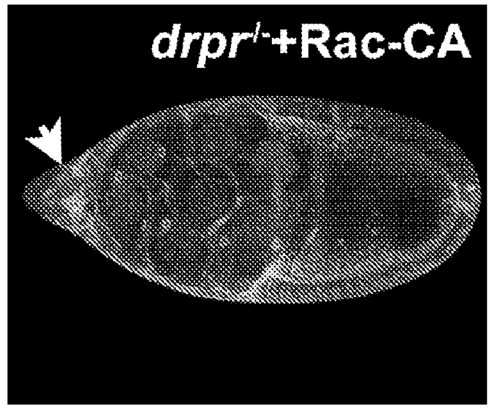

FIG. 4E is an image showing exemplary anterior follicle cells including border cells which start engulfing the surrounding follicle cells (arrow).

Figure 4F:
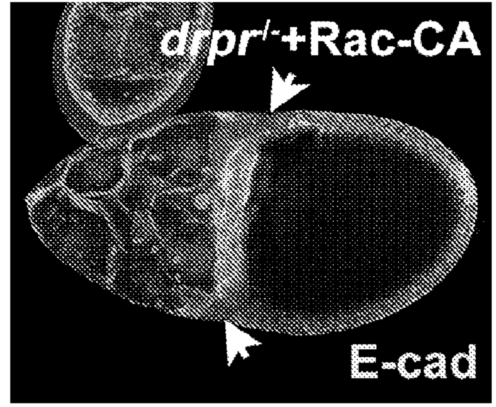

FIG. 4F is an image showing an exemplary centripetal cell migration which is unaffected (arrows) however these cells display an abnormal multilayered morphology. Egg chambers are labeled for E-Cad (grey).

FIG. 4G shows a chart illustrating results of experiments in which the box plots represent percentage of egg chambers with dead nurse cells detected for indicated genotypes. 'n' represents number of egg chambers observed.

FIG. 4H shows a chart illustrating results of experiments in which quantification of loss of E-Cad from nurse cell-nurse cell interface was detected in indicated genotypes. All data were analyzed by 1-way ANOVA with Tukey Kramer post hoc analysis. **=p<0000, *=p<0.001, **=p<0.01.

FIG. 4I is an image showing an exemplary high magnification image representing border cell cluster expressing lacZ driven by a slbo enhancer showing individual border cells 'b' and polar cells 'p'.

FIG. 4J is an image showing exemplary Rac-CA expressing cluster bites pieces from a non Rac-CA expressing polar cells (arrow).

FIG. 4K is an image showing an exemplary expression of Rac-CA in draper homozygous background displaying a similar bite or complete engulfment (arrow) of non-Rac-CA expressing polar cells suggesting that the follicle cell engulfment does not require draper. Border cells (b, solid lines) and polar cells (p, dashed lines) are marked and labeled for E-Cad (grey).

FIG. 4L is an image showing exemplary egg chambers expressing UAS-GFP and UAS-lacZ under the control of stretch cell specific PG150-Gal4; tub-GAL80ts.

FIG. 4M is an image showing exemplary expression of Rac-CA in stretch cells cause them to prematurely kill the germline nurse cells.

FIG. 4N is an image showing an exemplary high magnification image of a Rac-CA expressing egg chamber shows all the condensed nurse cell nuclei suggesting the process of killing of nurse cells by stretch cells is synchronous. Egg chambers are labeled for GFP (grey). Scale bars in A-F and I-N are 50 and 20 μm, respectively.

FIGS. 5A to 5E show images and charts illustrating the expression of a constitutively active Rac2 [E62K] in differentiated HL60 macrophages enhances engulfment and killing of leukemic Jurkat T-cells.

In particular, FIG. 5A is an image showing exemplary differentiated HL60 macrophages expressing Lck-GFP which are co-cultured with Cell Tracker Red labeled Jurkat T-cells show little engulfment (white arrow) or stable HL60-Jurkat contacts (gray arrow).

FIG. 5B is an image showing an exemplary expression of wild type Rac2 in differentiated HL60 macrophages which enhance Jurkat T-cell engulfment.

FIG. 5C is an image showing an exemplary expression of a constitutively active Rac2 [E62K] in differentiated HL60 macrophages which further increases Jurkat T-cell engulfment and killing. Stable HL60-Jurkat contacts are also significantly increased.

Figure 5D:
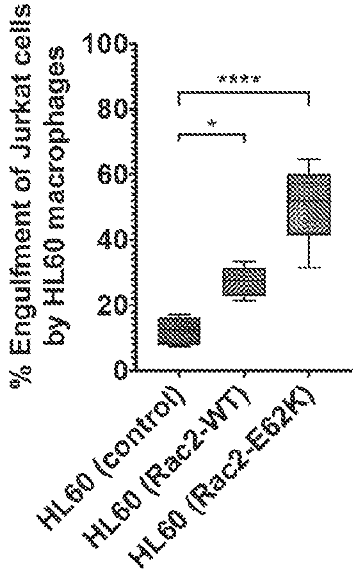

FIG. 5D shows a chart illustrating results of experiments in which box plots represent detected percentage of engulfment of Jurkat T-eel/s by differentiated HL60 macrophages.

Figure 5E:
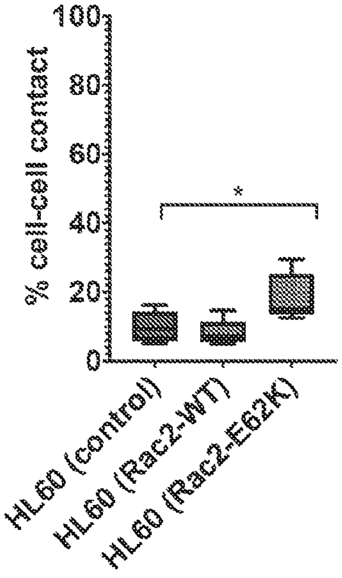
Figure 6A:
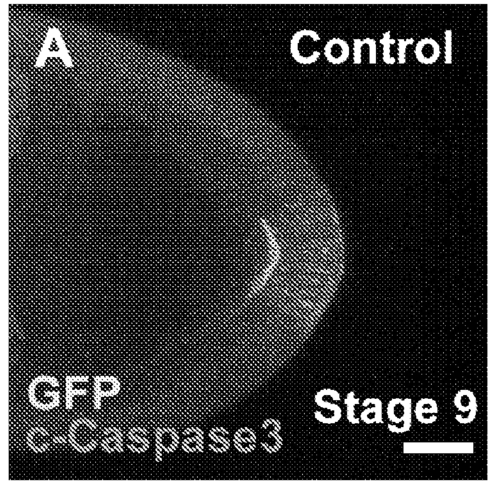
Figure 6B:
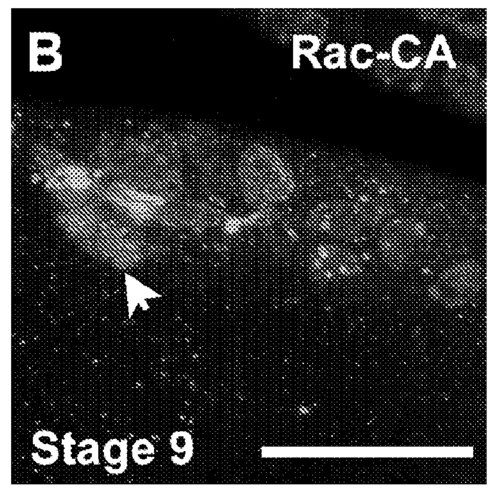
Figure 6C:
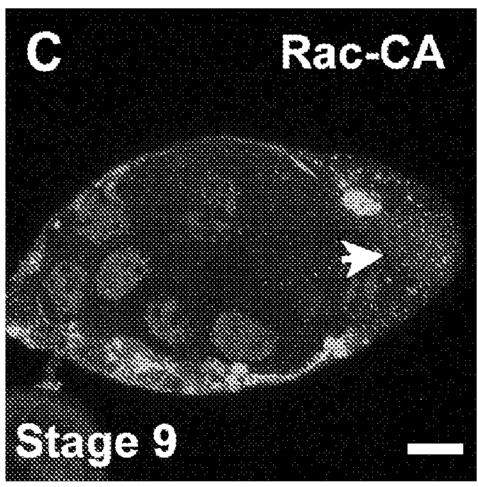
Figure 6D:
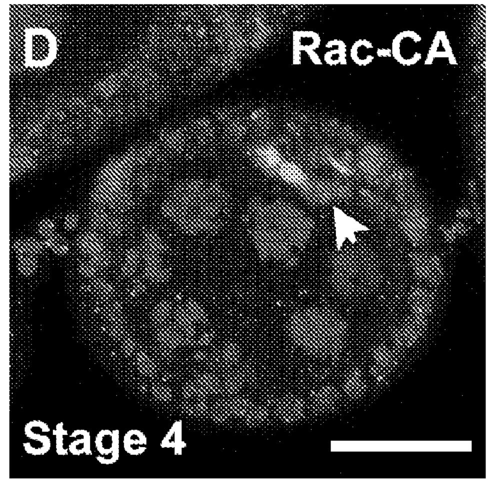

FIG. 5E shows a chart illustrating results of experiments in which quantification of percentage of stable HL60-Jurkat contacts was detected in indicated genotypes. Data were analyzed by 1-way ANOVA with Tukey Kramer posthoc analysis. ****=p<0.0001,*=p<0.05. Scale bar 50 μm.

FIGS. 6A to 6D Constitutively active Rac in a subset of follicle cells initiate caspase mediated follicle cell death. (FIG. 6A) Flpout clones expressing either control lacZ (FIG. 6A) or Rac-CA (FIGS. 6B, 6C, 6D) in a subset of follicle cells are labeled by GFP antibody (white), and cleaved Caspase-3 (white arrows). Control egg chambers (FIG. 6A) display no c-Caspase3 staining whereas Rac-CA expressing egg chambers show non-autonomous accumulation of c-Caspase3 (white arrows) next to the GFP+ (white) clones. Scale bars 20 μm.

Figures 7A, 7B, 7C:
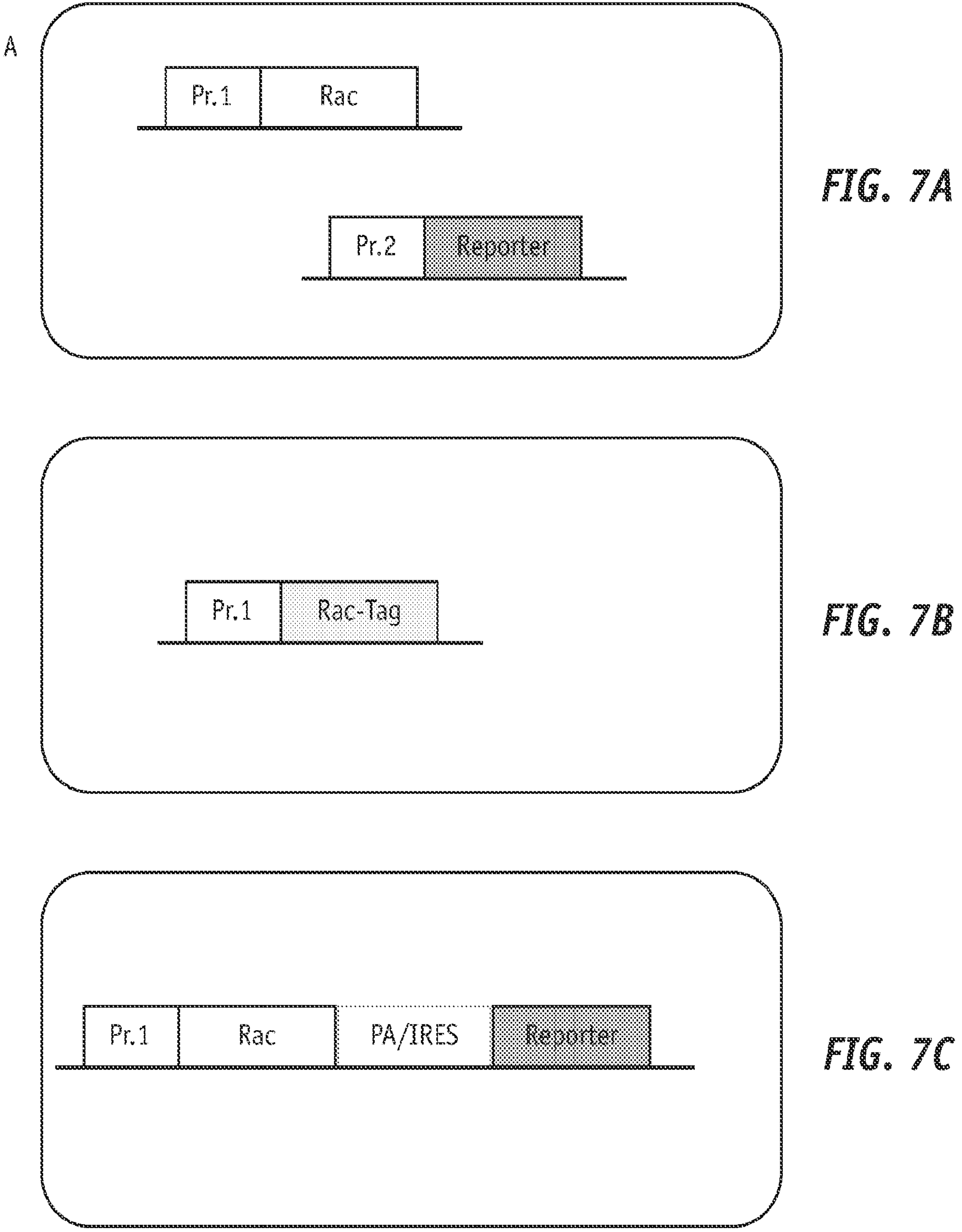

FIGS. 7A to 7C show schematic representation of exemplary activated phagocytes according to the instant disclosure Every rectangle represents a genetically engineered activated phagocyte with different or combinate vectors. Different colors and shades of gray represent a specific vector element.

FIGS. 8A to 8D show schematic representation of exemplary activated phagocytes according to the instant disclosure Every rectangle represents a genetically engineered activated phagocyte with different or combinate vectors. Different colors and shades of gray represent a specific vector element.

Figure 9A:
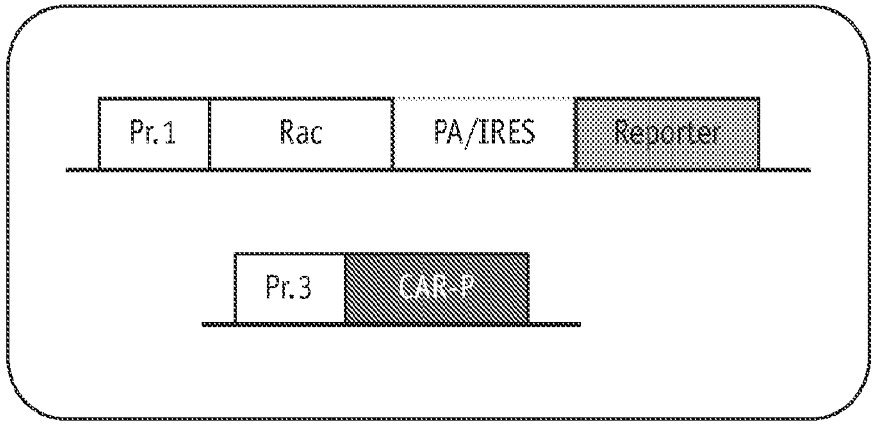
Figure 9B:
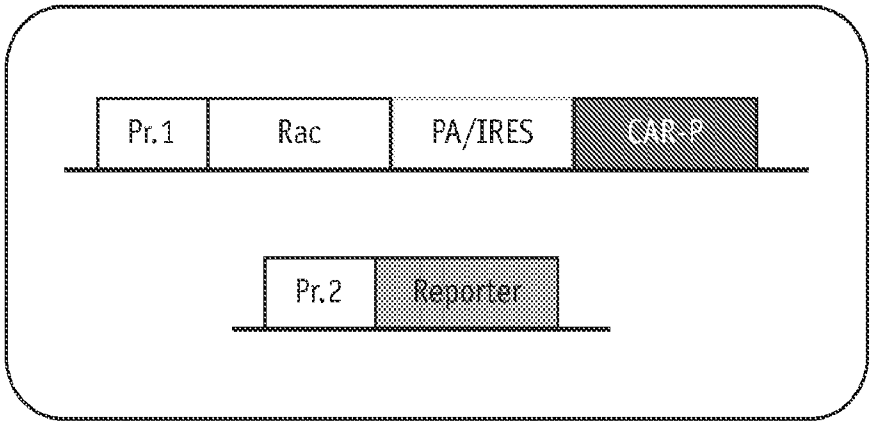

FIGS. 9A to 9B show schematic representation of exemplary activated phagocytes according to the instant disclosure Every rectangle represents a genetically engineered activated phagocyte with different or combinate vectors. Different colors and shades of gray represent a specific vector element.

DETAILED DESCRIPTION

Provided herein are activated phagocytes and in particular genetically engineered phagocytes, vectors, compositions and related methods and systems, which can provide and/or allow for engulfment and/or trogocytosis of a target cell by activating Rac gene in individuals.

It was unexpectedly discovered by the inventors of the present invention that by modifying Rac concentration, activity, and/or function in a phagocytic cell that the phagocytic cell can exhibit an increase in phagocytosis and/or trogocytosis. In some embodiments, a phagocytic cell is modified to have an increased concentration of a Rac protein or portion thereof in the cell and/or to have a different type (e.g., sequence and/or structure) of Rac protein or portion thereof in the cell, which can thereby modify Rac concentration, activity, and/or function in the phagocytic cell.

The terms "phagocytic cell" or "phagocyte" or plural forms thereof as used herein indicate a cell that is capable of phagocytosis, which is the process by which a cell uses its plasma membrane to engulf a large particle (≥0.5 μm), giving rise to an internal compartment called the phagosome. Phagocytosis is one type of endocytosis as will be understood by a skilled person. Phagocytes of an individual typically use their plasma membrane to engulf and remove cellular debris, foreign substances, microbes, and cells to protect the body of an individual. Phagocytes in the sense of the disclosure can typically also perform trogocytosis a process whereby lymphocytes (B, T and NK cells) conjugated to antigen-presenting cells extract surface molecules from these cells and express them on their own surface.

The terms "engineered" or "recombinant" in reference to a phagocyte, gene, nucleic acid and/or protein as used herein, refer to a phagocyte, gene, nucleic acid and/or protein that has been altered through human intervention. Accordingly, the term "naturally occurring" as used herein in reference to a phagocyte, gene, nucleic acid and/or protein as used herein, refer to a phagocyte, gene, nucleic acid and/or protein existing in nature and without any human intervention. Exemplary human interventions comprise transfection with a heterologous polynucleotide, molecular cloning resulting in a deletion, insertion, modification and/or rearrangement with respect to a naturally occurring sequence such as a naturally occurring sequence in a phagocyte, gene, nucleic acid and/or protein herein described.

The term "individual" or "subject" or "patient" as used herein includes multicellular organisms such as a single animal and in particular higher animals and in particular invertebrates or vertebrates such as manuals and more particularly human beings.

Exemplary phagocytic cells herein described include macrophages, monocytes, neutrophils, dendritic cells and precursors thereof as a person skilled in the art would understand, though singled celled organisms such as Dictyostelium amoebae are also phagocytes.

The term "macrophage" as used herein indicates a type of white blood cell of the immune system that is capable of phagocytosis. Macrophages are derived from blood monocytes that migrate into tissue. One of macrophages' main functions is to phagocytose microbes and clear cellular debris. Macrophages also play an important role in both the initiation and resolution of inflammation. Macrophages can also display different responses, ranging from pro-inflammatory to anti-inflammatory, depending on the type of stimuli they receive from the surrounding microenvironment. M1 and M2 are two major macrophage phenotypes that have been proposed to correlate with extreme macrophage responses. Macrophages in the sense of the disclosure comprise cells typically diffusely scattered in the connective tissue and in liver (Kupffer cells), spleen and lymph nodes (sinus histiocytes), lungs (alveolar macrophages), and central nervous system (microglia) as will be understood by a skilled person.

The term "monocyte" as used herein indicate a type of leukocyte or white blood cell capable of phagocytosis which are the largest type of leukocyte and can differentiate into macrophages and myeloid lineage dendritic cells. As a part of the vertebrate innate immune system monocytes also influence the process of adaptive immunity. There are at least three subclasses of monocytes in human blood based on their phenotypic receptors including $CD14^{++}$ $CD16^{-}$ monocyte, $CD14^{+}CD16^{++}$ T monocyte and $CD14^{++}$ $CD16^{+}$ monocytes, as will be understood by a person skilled in the art. Monocytes serve as precursors for various tissue macrophage and dendritic cell populations and contribute to both protective and pathological immune responses.

The term "dendritic cells" as used herein indicates specialized antigen-presenting cells capable of phagocytosis that have long outgrowths called dendrites that help to engulf microbes and other invaders. Dendritic cells are present in the tissues that are in contact with the external environment, mainly the skin, the inner lining of the nose, the lungs, the stomach, and the intestines. Once activated, they mature and migrate to the lymphoid tissues where they interact with T cells and B cells to initiate and orchestrate the adaptive immune response. Mature dendritic cells activate T helper cells and cytotoxic T cells. (Sompayrac 2019). The activated helper T cells interact with macrophages and B cells to activate them in turn. In addition, dendritic cells can influence the type of immune response produced; when they travel to the lymphoid areas where T cells are held, they can activate T cells, which then differentiate into cytotoxic T cells or helper T cells.

The term "neutrophils" as used herein indicates phagocytes that form the most abundant type of granulocytes and the most abundant type of white blood cells in most mammals as known to a person skilled in the art. Neutrophils are formed from stem cells in the bone marrow and differentiated into subpopulations of neutrophil-killers and neutrophil-cagers.

The wording "precursors" when used in connection with macrophages, monocytes, dendritic cells, and/or neutrophils (herein also precursor cells) as used herein indicates parent cells in a cellular lineage resulting into phagocytic cells herein described. Exemplary precursor cells include bone marrow, stem cells and other precursor cells identifiable by a person skilled in the art.

Phagocytes of various embodiments in accordance with the present disclosure are naturally occurring or engineered activated phagocytes capable of expressing an activated Rae protein and/or a Rac protein at activating expression level.

The term "activated" as used herein with reference to a Rac protein refers to a Rae protein having a sequence resulting in and/or that provides an enhanced Rac property.

The term "activated" as used herein with reference to a Rac gene indicates a Rac gene encoding an activated Rac protein in the sense of the disclosure, and therefore is a Rac protein configured to provide enhanced Rac properties.

The term "activated" "or "activating" as used herein with reference to an expression level of a Rac protein indicates an expression level that is increased relative to a baseline expression level, and the increased expression level results in enhanced Rac properties.

As used herein, the terms "increase," "increasing," "improve" and "improving" (and grammatical variations thereof) describes unless the context indicates otherwise a detectable elevation of a reference value. An increase can comprise an elevation of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more such as compared to another measurable property or quantity (e.g., a control value).

Rac properties in the sense of the disclosure are properties characterizing the biological activity of a Rac protein comprising GTP binding, GTP hydrolysis and/or association with downstream effectors which mediate Rac effects on various biological events such as structural changes to the actin, cytoskeletal reorganization, cell growth, cell movement, translocation of glucose transforming vesicles, glucose uptake, antimicrobial cytotoxicity, the activation of protein kinases and additional events identifiable by a skilled person. Exemplary downstream effectors comprise the serine/threonine-protein kinase Akt also known as protein kinase B as well as ser/thr protein kinase, $p65^{PAK}$ also known as PAK1 and additional downstream effectors identifiable by a skilled person.

Enhanced Rac properties in the sense of the disclosure are increased Rac properties determined with respect to Rac properties of a non-activated Rac protein having SEQ ID NO: 1

```
MQAIKCVVVGDGAVGKTCLLISYTTNAFPGEYIPTVFDNYSANVMVDSK

PVNLGLWDTAGQEDYDRLRPLSYPQTDVFLICFSLVSPASYENVRAKWF
```

-continued

PEVRHHCPSTPIILVGTKLDLRDDKDTIEKLKEKKLAPITYPQGLALAK

EIDSVKYLECSALTQRGLKTVFDEAIRAVLCPQPTRQQKRACSLL

Accordingly, presence of enhanced properties of an activated Rac protein in a phagocyte can be determined by detecting binding to GTP of a Rac protein from the phagocyte to provide a phagocyte Rac protein GTP binding rate, and detecting binding to GTP of a non-activated Rac protein of SEQ ID NO: 1 to provide a non-activated Rac protein GTP binding rate, and comparing the two Rac protein GTP binding rates to determine if there is an increase in the phagocyte Rac protein GTP binding rate compared to the non-activated Rac protein GTP binding rate.

In embodiments herein described detecting binding to GTP can be performed with a test such as Guanine nucleotide exchange factor (GFP)-mediated guanine nucleotide exchange as determined by GDP exchange assays (see Example 5 and Example 6), GTP hydrolysis assays in presence of GAP and/or with other assays identifiable by a skilled person.

Accordingly, enhanced Rac properties can be detected by comparing the phagocyte Rac protein GTP binding rate with the non-activated Rac protein GTP binding rate, wherein enhanced properties are detected when the phagocyte Rac protein GTP binding rate, or equivalent parameter (such as the amount of Rac-GTP complex formed) is higher than the non-activated Rac protein GTP binding rate (see Example 5 and Example 6).

In particular, in some embodiments enhanced Rac properties are detected when the phagocyte Rac protein GTP binding rate is higher than the non-activated Rac protein GTP binding rate of the non-activated Rac protein of SEQ ID NO: 1.

In some of those embodiments, the phagocyte Rac protein GTP binding rate can be about 1.5 fold to 2 fold higher, or even higher than the non-activated Rac protein GTP binding rate of the non-activated Rac protein of SEQ ID NO: 1, possibly about 2 fold higher, 3 fold higher, 4 fold higher, 5 fold higher, 6 fold higher, 7 fold higher, 8 fold higher, 9 fold higher, than the non-activated Rac protein of SEQ ID NO: 1.

The term "about," as used herein when referring to a measurable value such as an amount or concentration and the like, is meant to encompass variations of ±10%, ±5%, ±1%, ±0.5%, or even ±0.1% of the specified value as well as the specified value unclear the context clearly indicates otherwise. For example, "about X" where X is the measurable value, is meant to include X as well as variations of ±10%, ±5%, ±1%, ±0.5%, or even ±0.1% of X. A range provided herein for a measurable value may include any other range and/or individual value therein.

The wording "fold change" as used herein indicates a measure describing how much a quantity changes between an original and a subsequent measurement. In particular, fold change is defined as the ratio between two quantities. For example, for quantities A and B, the fold change of B with respect to A is B/A. In other words, a change from 30 to 60 is defined as a fold-change of 2 (source Wikipedia page (20 Apr. 2021)).

In some embodiments, the phagocyte Rac protein GTP binding rate can be more than 10 fold higher than the non-activated Rac protein GTP binding rate of the non-activated Rae protein of SEQ ID NO: 1, possibly about 20 fold higher, 30 fold higher, 40 fold higher, 50 fold higher, 60 fold higher, 70 fold higher, 80 fold higher, 90 fold higher and up to 100 fold higher than the non-activated Rac protein of SEQ ID NO: 1.

In addition or in alternative, presence of enhanced properties of activated Rac proteins in a phagocyte can be detected by quantitatively detecting GTP hydrolysis by a Rac protein from the phagocyte to provide a phagocyte Rac protein GTP hydrolysis rate, and quantitatively detecting hydrolysis of GTP by a non-activated Rac protein of SEQ ID NO 1 to provide a non-activated Rac protein GTP hydrolysis rate.

Enhanced properties can then be detected by comparing the phagocyte Rac protein GTP hydrolysis rate with the non-activated Rac protein GTP hydrolysis rate, wherein enhanced properties are detected when the phagocyte Rac protein GTP hydrolysis rate is lower than the non-activated Rac protein GTP hydrolysis rate.

In particular, in some embodiments enhanced Rac properties are detected when the phagocyte Rac protein GTE hydrolysis rate is 50% or less compared a non-activated Rae protein GTP hydrolysis rate.

In addition or in alternative, presence of enhanced properties of activated Rac proteins in a phagocyte can be detected by quantitatively detecting a product of a reaction between a phagocyte Rac protein with a Rac downstream effector to provide a detected downstream product level from the phagocyte Rac protein, and quantitatively detecting a product of the same reaction between a non-activated Rac protein with the same downstream effector to provide a detected downstream product level provided from the non-activated Rac protein.

Enhanced properties can then be detected by comparing the detected downstream product level from phagocyte Rac protein with the detected downstream product level of the non-activated Rac protein wherein enhanced properties are detected when the detected downstream product level from the phagocyte Rac protein is higher than detected downstream product from the non-activated Rac product level.

In some embodiments enhanced Rac properties can be detected when the detected downstream product level from the phagocyte Rac protein is about 1.5-2 fold higher or even higher than detected product level from the non-activated Rac protein, of the non-activated Rac protein of SEQ ID NO: 1, possibly about 2 fold higher, 3 fold higher, 4 fold higher, 5 fold higher, 6 fold higher, 7 fold higher, 8 fold higher, 9 fold higher, than the non-activated Rae protein of SEQ ID NO: I.

In some embodiments, the detected downstream product level of the phagocyte Rae protein can be more than 10 fold higher than the detected downstream product level the non-activated Rac protein of SEQ ID NO: 1, possibly about 20 fold higher, 30 fold higher, 40 fold higher, 50 fold higher, 60 fold higher, 70 fold higher, 80 fold higher, 90 fold higher and up to 100 fold higher than the non-activated Rac protein of SEQ ID NO: 1.

Specific downstream effector and corresponding product levels can be identified by a skilled person upon reading of the present disclosure. Exemplary downstream effectors comprise Akt which is phosphorylated by Rac to provide a downstream product such as phosphorylated pAKT, ser/thr protein kinase, $p65^{PAK}$ also known as PAK1 which when activated by Rac provides as downstream product actin polymerization and F actin content, cytosolic NADPH oxidase $p67^{phox}$ and $gp91^{phox}$ which when activated by Rac provide reactive oxygen species (ROS) as downstream product.

In particular, in some embodiments, the downstream effector is AKT, the product is pAKT, and enhanced properties are detected when phosphorylation of AKT by the phagocyte Rac protein provides a level of pAKT from about 1.5 fold to about 2 fold or higher with respect to the non-activated Rac protein. In particular, levels of pAKT from about 1.5-fold to about 2-fold or higher with respect to the Rac protein of SEQ ID NO: 1, will indicate enhanced downstream signaling by activated Rac expression levels, as will be understood by a skilled person.

In some embodiments, the downstream effector is PAK, the reaction product is actin polymerization/F-actin content, and enhanced properties are detected when activation of PAK 1 by the phagocyte Rac protein provides an increase in F-actin content from about 1.5 fold to about 2 fold or higher with respect to the non-activated Rac protein of SEQ ID NO: 1. In particular, an increase in F-actin content from about 1.5 fold to about 2 fold or a higher with respect to the F-actin content of Rac Protein of SEQ ID NO: 1, can be an indicator of increased active Rac dependent signaling as will be understood by a skilled person.

In some embodiments, the downstream effector is one or both of an increase in Reactive oxygen species (ROS) production over time from about 1.5 increase to about 2-fold increase or higher and an increase in micropinocytosis (cell drinking) from about 1.5-2 fold or higher. In particular an increase in one or both of the ROS and micropinocytosis with respect to Rac protein of SEQ ID NO; 1 will be considered an enhanced downstream signaling by activated Rac expression.

In some embodiments, an activated Rac protein and/or an activated Rac expression level can provide and/or is configured to provide one, two, three or more enhanced Rac properties in any possible combinations as will be understood by a skilled person upon reading of the present disclosure.

In some embodiments, an activated Rac protein and/or an activated Rac expression level can provide and/or is configured to provide in the PAK-PBD binding assays (for the measurement of the GTP/GDP bound ratios of Rac in vitro), from a 10% to 100 fold (±5% error margin) increase in binding of the GTP with respect to the non-activated Rac protein of SEQ ID NO: 1.

In some embodiments, an activated Rac protein and/or an activated Rac expression level can provide and/or is configured to provide from a 10% to 100 fold (±5% error margin) increase in phosphorylation of AKT levels (a downstream effector of Rae) with respect to the non-activated Rac protein of SEQ ID NO: 1.

In some embodiments, an activated Rac protein and/or an activated Rac expression level can provide and/or is configured to provide from a 10% to 100 fold (±5% error margin) increase in Reactive oxygen species (ROS) production over time and/or from a 10%-100 fold (±5% error margin) increase in micropinocytosis (cell drinking) with respect to the non-activated Rac protein of SEQ ID NO: 1.

In some embodiments, an activated Rac protein and/or an activated Rac expression level can provide and/or is configured to provide enhanced Rac properties tolerated by cells without causing detectable toxicity/phenotypic abnormality.

In some embodiments, the activated Rac proteins are encoded by a mutated Rac gene having mutations enhancing a Rac property and/or activity. In some embodiments, an activated Rac protein expression level is provided and/or achieved by overexpressing or inhibiting one or more upstream regulators, such as guanine nucleotide exchange factors (GEFs, such as TIAM1, Vav, and additional exchange factors identifiable by a skilled person) or guanine nucleotide triphosphatase activating proteins (GAPs), involved in the Rac signaling pathway, therefore resulting in the activation of Rac.

The term "Rac gene" as used herein indicates a gene encoding a Rac protein of Rho-family of GTPases capable of stimulating actin polymerization and protrusion at the leading edges of migrating cells, stimulating micropinocytosis and/or and stimulating phagocytosis, as measured using standard assays such as pyrene-actin incorporation and microscopy. Exemplary features of Rac genes are described for example in Ridley et al. 1992 (Ridley, Paterson et at 1992); Murphy and Montell 1996 (Murphy and Montell 1996); Ridley 2015 (Ridley 2015); Massol et al. 1998 (Massol, Montcourrier et al. 1998).

A Rac protein in the sense of the disclosure refers any protein sequence (natural or synthetic) retrieved by the BLASTp, or other algorithm and program for comparing primary biological sequence information using SEQ ID NO: 1 MQAIKCVVVGDGAVGKTCLLISYTT-NAFPGEYIPTVFDNYSANVMVDSKPVNLGLWD-TAGQEDYDRL RPLSYPQTDVFLICFSLVSPASY-ENVRAKWFPEVRHHCPSTPIILVGTKLDLRDDKDTIE KILKEKKLAPIT YPQGLALAKEDSVKYLECSALTQR-GLKTVJFDEAIRAVLCPQPTRQQKIRACSLL as a reference sequence.

As used herein, "reference sequence" is a defined sequence used as a basis for sequence comparison. A reference sequence may be a subset or the entirety of a specified sequence; for example, as a segment of a full-length protein or protein fragment. A reference sequence can comprise, for example, a sequence identifiable in a database such as GenBank and UniProt and others identifiable to those skilled in the art.

Algorithms and programs for comparing primary biological sequence information between any two sequences are identifiable by a skilled person. Non-limiting examples of such mathematical algorithms are the algorithm of Myers and Miller (Myers and Miller 1988), the local homology algorithm of Smith et al. (Smith and Waterman 1981); the homology alignment algorithm of Needleman and Wunsch (Needleman and Wunsch 1970)); the search-for-similarity-method of Pearson and Lipman (Pearson and Lipman 1988).); the algorithm of Karlin and Altschul (Karlin and Altschul 1990), modified as in Karlin and Altschul (Karlin and Altschul 1993)). Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA (Pearson and Lipman 1988).), and TFASTA in the Wisconsin Genetics Software Package, Version 8 (available from Genetics Computer Group (GCG), 575 Science Drive, Madison, Wis., USA). Alignments using these programs can be performed using the default parameters and allowing a user to identify database sequences that resemble the reference sequence (query sequence) above a certain threshold of confidence.

Algorithms and programs for comparing primary biological sequence information between any two sequences typically provide an output comprising percent identity between the sequence retrieved and the reference sequence.

A person skilled in the art would understand that identity between sequences is typically measured by a process that comprises the steps of aligning the two polypeptide or polynucleotide sequences to form aligned sequences, then detecting the number of matched characters, i.e. characters similar or identical between the two aligned sequences, and calculating the total number of matched characters divided by the total number of aligned characters in each polypeptide or polynucleotide sequence, including gaps. The similarity result is expressed as a percentage of identity.

As used herein, "percentage of sequence identity" means the value determined by comparing two optimally aligned sequences over a comparison window, wherein the portion of the polynucleotide sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Rac proteins in the sense of the disclosure can comprise activated and non-activated naturally occurring or synthetic proteins having a percent identity of 96% or higher with respect to SEQ ID NO: 1, and in particular, encompass sequences with a percent identify of, 96.88%, 97.38%. 97.40%, 97.44%, 97.91%, 97.92%, 98.44%, 98.96%, 99.48%, and 100.00% Additional percent identity with SEQ ID NO: 1 are identifiable by a skilled person.

In particular, activated Rac proteins can also comprise proteins with a lower percent identity to SEQ ID NO: 1 and still maintaining or showing an increase in one or more Rae property. Accordingly, Rac sequence can comprise sequences with a percent identify with respect to SEQ ID NO 1 lower than 96%, e.g. as a consequence of human intervention, as will be understood by a skilled person upon reading of the present disclosure.

In particular, the term Rac protein encompasses three highly related Rac proteins in humans Rae1, Rac2 and Rac3 which are also highly conserved among individuals of different taxonomic ranks (see Example 1, Example 2). In particular Rac1, Rac2 and Rac3 contain nucleotide binding regions that bind to Guanosine Triphosphates (GTP), an effector region located at the N-terminus which binds to the downstream effectors and shares a conserved lipid binding region at their C-terminus. The effector region is also known as switch I region whereas switch II region is the site where RAC proteins bind to the GTP as will be understood by a skilled person (see Example 2) (Kumar, Rajendran et al. 2013).

The term "Rac1 gene" or "RAC1" as used herein indicates a gene encoding the Rae 1 protein of the Rho-family of GTPases small guanosine triphosphate (GTP)-metabolizing proteins. Rac1 is provided in a variety of alternatively spliced versions of the Rae1 protein, Rac1 is a pleiotropic regulator of many cellular processes, including the cell cycle, cell-cell adhesion, motility (through the actin network), and of epithelial differentiation (proposed to be necessary for maintaining epidermal stem cells) (from (Wikipedia 31 Dec. 2020).

The term "Rac-2 gene" or "RAC2" as used herein indicates a gene encoding the Rae-2 protein of the Rho-family of GTPases small guanosine triphosphate (GTP)-metabolizing proteins. The encoded protein localizes to the plasma membrane, where it regulates diverse processes, such as secretion, phagocytosis, and cell polarization. Activity of this protein is also involved in the generation of reactive oxygen species. Mutations in this gene are associated with neutrophil immunodeficiency syndrome. Rac-2 gene which is naturally predominantly expressed in cells of hematopoietic origin and is required for phagocyte chemotaxis and superoxide production as well as for lymphocyte development and/or survival.

The term "Rac-3 gene" or "RAC3" as used herein indicates a gene encoding the Rae-3 protein of the Rho-family of GTPases small guanosine triphosphate (GTP). Rac3 is an active GTPase, regulated by Bcr. When constitutively activated, Rac3 is able to stimulate efficiently the c-Jun amino-terminal kinase signaling pathway. These findings support a role for Rac3 in intracellular signaling. Rac3 protein levels are not affected by organization of the actin cytoskeleton but remarkably, are serum-inducible (source Haataja, Groffen et al. 1997) The term "gene" as used herein indicates a polynucleotide encoding for a protein that in some instances can take the form of a unit of genomic DNA within a bacteria, plant, or other organism. The term gene as used herein incudes naturally occurring polynucleotide encoding for a protein as well as engineered polynucleotide whose sequences have been modified from the original sequence for example to optimize expression, e.g. through codon changes (see Examples section) and/or through introduction of modified N- and/or C-terminal modifications, while still maintaining the ability to encode for the protein encoded by the naturally occurring polynucleotide or a or a functional variant thereof.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Accordingly, the term polynucleotide includes nucleic acids of any length, and in particular DNA RNA analogs and fragments thereof.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full-length proteins and peptides, as well as analogs and fragments thereof. A polypeptide of three or more amino acids is also called a protein oligorner, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immunoprecipitation, and a variety of other methods as understood by a person skilled in the art. Proteins can be provided in vitro or in vivo by several methods identifiable by a skilled person. In some instances where the proteins are synthetic proteins in at least a portion of the polymer two or more amino acid monomers and/or analogs thereof are joined through chemically-mediated condensation of an organic acid (—COOH) and an amine (—$NH_2$) to form an amide bond or a "peptide" bond.

A "portion" or "fragment" of a nucleotide sequence or polypeptide sequence will be understood to mean a nucleotide or polypeptide sequence of reduced length (e.g., reduced by 1, 2, 3, 4, 5, 6, 7, 8, 9, 10, 11, 12, 13, 14, 15, 16, 17, 18, 19, 20 or more residue(s) (e.g., nucleotide(s) or peptide(s)) relative to a reference nucleotide or polypeptide sequence, respectively, and comprising, consisting essentially of and/or consisting of a nucleotide or polypeptide sequence of contiguous residues respectively, which maintains the functionality of the reference nucleotide or polypeptide sequence. A portion, or fragment can comprise nucleotide sequence or polypeptide sequence identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleotide or polypeptide sequence. Such a nucleic acid fragment or portion according to the invention may be, where appropriate, included in a larger polynucleotide of which it is a constituent.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

Exemplary Rac proteins comprise the non-activated Rac proteins summarized in Table 1

TABLE 1

| Rac protein | Sequence information | Sequence | SEQ ID NO |
|---|---|---|---|
| Human Rac2 | >NP_002863.1 ras-related C3 botulinum toxin substrate 2 [*Homo sapiens*] | MQAIKCVVVGDGAVGKTCLLISYTTNA FPGEYIPTVFDNYSANVMVDSKPVNLGL WDTAGQEDYDRLRPLSYPQTDVFLICFS LVSPASYENVRAKWFPEVRHHCPSTPIIL VGTKLDLRDDKDTIEKLKEKKLAPITYP QGLALAKEIDSVKYLECSALTQRGLKTV FDEAIRAVLCPQPTRQQKRACSLL | 1 |
| Human Rac1 | >NP_008839.2 ras-related C3 botulinum toxin substrate 1 isoform Rac1 [*Homo sapiens*] | MQAIKCVVVGDGAVGKTCLLISYTTNA FPGEYIPTVFDNYSANVMVDGKPVNLGL WDTAGQEDYDRLRPLSYPQTDVFLICFS LVSPASFENVRAKWYPEVRHHCPNTPIIL VGTKLDLRDDKDTIEKLKEKKLTPITYP QGLAMAKEIGAVKYLECSALTQRGLKT VEDEAIRAVLCPPPVKKRKRKCLLL | 2 |
| Human Rac3 | >NP_005043.1 ras-related C3 botulinum toxin substrate 3 isoform 1 [*Homo sapiens*] | MQAIKCVVVGDGAVGKTCLLISYTTNA FPGEYIPTVFDNYSANVMVDGKPVNLGL WDTAGQEDYDRLRPLSYPQTDVFLICES LVSPASFENVRAKWYPEVRHHCPHTPIL LVGTKLDLRDDKDTIERLRDKKLAPITY PQGLAMAREIGSVKYLECSALTQRGLKT VFDEAIRAVLCPPPVKKPGKKCTVF | 3 |
| Human Cdc42 | >NP_001782.1 cell division control protein 42 homolog isoform 1 precursor [*Homo sapiens*] | MQTIKCVVVGDGAVGKTCLLISYTTNKF PSEYVPTVFDNYAVTVMIGGEPYTLGLF DTAGQEDYDRLRPLSYPQTDVFLVCFSV VSPSSFENVKEKWVPEITHHCPKTPFLLV GTQIDLRDDPSTIEKLAKNKQKPITPETA EKLARDLKAVKYVECSALTQKGLKNVF DEAILAALEPPEPKKSRRCVLL | 4 |
| *Drosophila* Rac1 | >NP_476950.1 Rac1, isoform A [*Drosophila melanogaster*] | MQAIKCVVVGDGAVGKTCLLISYTTNA FPGEYIPTVFDNYSANVMVDAKPINLGL WDTAGQEDYDRLRPLSYPQTDVFLICES LVNPASFENVRAKWYPEVRHHCPSTPIIL VGTKLDLRDDKNTIEKLRDKKLAPITYP | 5 |

TABLE 1-continued

| Rac protein | Sequence information | Sequence | SEQ ID NO |
|---|---|---|---|
| | | QGLAMAKEIGAVKYLECSALTQKGLKT VFDEAIRSVLCPVLQPKSKRKCALL | |
| Bovine Rac1 | >NP_776588.1 ras-related C3 botulinum toxin substrate 1 [*Bos taurus*] | MQAIKCVVVGDGAVGKTCLLISYTTNA FPGEYIPTVFDNYSANVMVDGKPVNLGL WDTAGQEDYDRLRPLSYPQTDVFLICES LVSPASFENVRAKWYPEVRHHCPNTPIIL VGTKLDLRDDKDTIEKLKEKKLTPITYP QGLAMAKEIGAVKYLECSALTQRGLKT VFDEAIRAVLCPPPVKKRKRKCLLL | 6 |
| Mouse Rac1 | >NP_001334459.1 ras-related C3 botulinum toxin substrate 1 isoform 1 [*Mus musculus*] | MQAIKCVVVGDGAVGKTCLLISYTTNA FPGEYIPTVFDNYSANVMVDGKPVNLGL WDTAGQEDYDRLRPLSYPQTVGDTCGK DRPSRGKDKPIADVFLICFSLVSPASFEN VRAKWYPEVRHHCPNTPIILVGTKLDLR DDKDTIEKLKEKKLTPITYPQGLAMAKE IGAVKYLECSALTQRGLKTVFDEAIRAV LCPPPVKKRKRKCLLL | 7 |
| *C elegans* Rac1 | >NP_500363.1 Ras-related protein ced-10 [*Caenorhabditis elegans*] | MQAIKCVVVGDGAVGKTCLLISYTTNA FPGEYIPTVFDNYSANVMVDGRPINLGL WDTAGQEDYDRLRPLSYPQTDVFLVCF ALNNPASFENVRAKWYPEVSHHCPNTPI ILVGTKADLREDRDTVERLRERRLQPVS QTQGYVMAKEIKAVKYLECSALTQRGL KQVFDEAIRAVLTPPQRAKKSKCTVL | 8 |
| *Drosophila* Rac2 | >NP_648121.1 Rac2, isoform A [*Drosophila melanogaster*] | MQAIKCVVVGDGAVGKTCLLISYTTNA FPGEYIPTVFDNYSANVMVDAKPINLGL WDTAGQEDYDRLRPLSYPQTDVFLICFS LVNPASFENVRAKWFPEVRHHCPSVPIIL VGTKLDLRDDKQTIEKLKDKKLTPITYP QGLAMAKEIAAVKYLECSALTQKGLKT VFDEAIRSVLCPVVRGPKRHKCALL | 9 |
| Bovine Rac2 | >NP_786986.1 ras-related C3 botulinum toxin substrate 2 [*Bos taurus*] | MQAIKCVVVGDGAVGKTCLLISYTTNA FPGEYIPTVFDNYSANVMVDSKPVNLGL WDTAGQEDYDRLRPLSYPQTDVFLICES LVSPASYENVRAKWFPEVRHHCPSTPIIL VGTKLDLRDDKDTIEKLKEKKLAPITYP QGLALAKEIDSVKYLECSALTQRGLKTV FDEAIRAVLCPQPTRPQKRPCSIL | 10 |
| Mouse Rac2 | >NP_033034.1 ras-related C3 botulinum toxin substrate 2 [*Mus musculus*] | MQAIKCVVVGDGAVGKTCLLISYTTNA FPGEYIPTVFDNYSANVMVDSKPVNLGL WDTAGQEDYDRLRPLSYPQTDVFLICES LVSPASYENVRAKWFPEVRHHCPSTPIIL VGTKLDLRDDKDTIEKLKEKKLAPITYP QGLALAKDIDSVKYLECSALTQRGLKTV FDEAIRAVLCPQPTRQQKRPCSLL | 11 |
| *C elegans* Rac2 | >NP_001040961.1 Ras-related protein rac-2 [*Caenorhabditis elegans*] | MQAIKCVVVGDGAVGKTCLLLSYTTNA FPGEYILTVFDTYSTNVMVDGRPINLSL WDTAGQDDYDQFRHLSFPQTDVFLVCF ALNNPASFENVRAKWYPEVSHHCPNTPI ILVGTKADLREDRDTIERLRERRLQPVSH TQGYVMAKEIKAVKYLECSALTQIGLK QVFDEAIRTGLTPPQTPQTRAKKSNCTV L | 12 |
| Rat Rac2 | >NP_001008385.1 ras-related C3 botulinum toxin substrate 2 [*Rattus norvegicus*] | MQAIKCVVVGDGAVGKTCLLISYTTNA FPGEYIPTVFDNYSANVMVDSKPVNLGL WDTAGQEDYDRLRPLSYPQTDVFLICES LVSPASYENVRAKWFPEVRHHCPSTPIIL VGTKLDLRDDKDTIEKLKEKKLAPITYP QGLALAKDIDSVKYLECSALTQRGLKTV FDEAIRAVLCPQPTRQQKRPCSLL | 13 |
| Zebrafish Rac2 | >NP_001002061.1 ras-related C3 botulinum toxin substrate 2 [*Danio rerio*] | MQAIKCVVVGDGAVGKTCLLISYTTNA FPGEYIPTVFDNYSANVMVDSKPVNLGL WDTAGQEDYDRLRPLSYPQTDVFLICFS LVSPASFENVRAKWYPEVRHHCPSTPIIL VGTKLDLRDEKETIEKLKEKKLAPITYPQ GLALAKEIDAVKYLECSALTQRGLKTVF DEAIRAVLCPQPTKVKKKGCVML | 14 |

TABLE 1-continued

| Rac protein | Sequence information | Sequence | SEQ ID NO |
|---|---|---|---|
| Chimpanzee Rac2 | >XP_016794604.1 ras-related C3 botulinum toxin substrate 2 [*Pan troglodytes*] | MQAIKCVVVGDGAVGKTCLLISYTTNA FPGEYIPTVFDNYSANVMVDSKPVNLGL WDTAGQEDYDRLRPLSYPQTDVFLICES LVSPASYENVRAKWFPEVRHHCPSTPIIL VGTKLDLRDDKDTIEKLKEKKLAPITYP QGLALAKEIDSVKYLECSALTQRGLKTV FDEAIRAVLCPQPTRQQKRTCSLL | 15 |

Additional, examples of Rac genes and protein sequences can be found in public gene databases such as NCBI Uniprot and other public genomic and protein sequence databases identifiable to a person skilled in the art.

The sequence of human RAC1 Transcript variant 1 is the canonical sequence, all positional information described with respect to the remaining isoforms are determined from this sequence, and the sequences are available to the public at the GenBank database under NM_006908.4 and NP 008839.2. The sequences of human RAC1 transcript variant 2 can be found under NM_018890.3 and NP 691485.1 and the encoded protein includes the alternatively spliced 57 bp region (exon 3b) that is missing in transcript variant RAC1. Nucleic acid and polypeptide sequences of RAC1 orthologs in organisms other than humans are well known and include, for example, mouse RAC1 (NM_009007.2 and NP 033033.1), rat RAC1 (NM_134366.1 and NP 599193.1), chicken RAC1 (NM_205017.1 and NP_990348.1), zebrafish RAC (NM_199771.1 and NP_956065.1), cow RAC1 (NM_174163.2 and NP 776588.1), and dog RAC1 (NM_001003274.2 and NP 001003274.1). (source US Patent US2015/0185223A1 incorporated by reference in its entirety) (Mano).

An exemplary Rac2 gene is Ras-related C3 botulinum toxin substrate 2, having an UniProt entry B1AH80 (web page https://www.uniprot.org/uniprot/B1AH80) as will be understood by a person skilled in the art. Exemplary Rac2 sequences can also include other sequences in the Ras subfamily PF0071 (web page http://pfam.xfam.org/family/PF00071) as will be understood by a skilled person. Nucleic acid and amino acid sequences of a representative human RAC2 biomarker is available to the public at the GenBank database under NM_002872.3 and NP 002863.1. Nucleic acid and polypeptide sequences of RAC2 orthologs in organisms other than humans are well known and include, for example, mouse RAC2 (NM_009008.3 and NP 033034.1), ratRAC2 (NM 001008384.1 and NP_001008385.1), chimpanzee RAC2 (XM_001145815.3 and XP 001145815.3), monkey RAC2 (XM_001086228.2 and XP_001086228.1), dog RAC2 (XM_538392.4 and XP 538392.4), cow RAC2 (NM 175792.2 and NP 786986.1), chicken RAC2 (NM_0012011452.1 and NP 001188381.1), and zebrafish RAC2 (NM_001002061.1 and NP 001002061.1). (source US Patent US2015/0185223A1 incorporated by reference in its entirety) (Mano).

The nucleic acid and amino acid sequences of a representative human RAC3 biomarker is available to the public at the GenBank database under NM_005052.2 and NP 005043.1. Nucleic acid and polypeptide sequences of RAC3 orthologs in organisms other than humans are well known and include, for example, mouse RAC3 (NM_133223.4 and NP 573486.1), monkey RAC3 (XM_001113336.2 and XP 00111336.2), cow RAC3 (NM_001099179.1 and NP_001092649.1), and chicken RAC3 (NM_205016.1 and NP 990347.1) (source US Patent US2015/0185223A1 incorporated by reference in its entirety). (Mano).

Rac1 Rac2 and Rac3 bind GTP with the nucleotide binding region (see Example 2 and Example 3) and with respect to hydrolysis of GTP, a number of GEFs (such as P-Rex1 and Dock-2) can activate both Rac1 Rac2 and Rac3 by facilitating their dissociation with GDP and association with GTP by interacting similarly with the nucleotide binding regions as will be understood by a skilled person (Pantarelli and Welch 2018) and the related activation detected as indicated in the present disclosure. (see e.g. Example 5 and Example 6) and identifiable by a skilled person.

Rac1, Rac2 and Rac3 are also known to bind various downstream effectors through the effector region (see Example 2 and Example 3) which can be used to determine whether a Rac1 Rac2 or Rac3 protein is an active Rac properties in the sense of the disclosure by detection of a related downstream product. For example, Rac1 and Rac2 can bind in addition to AKT, PAK1 and p67$^{phox}$ and gp91$^{phox}$ downstream effector Arp⅔ complex (actin nucleator) and coffilin (actin-binding proteins associated with the rapid depolymerization of actin microfilaments) to regulate actin dynamics and provide actin polymerization (Arp⅔ complex) and depolymerization (cofflin) as downstream product. Downstream effector of Rae 3 comprise HNF1 homeobox A (hepatocyte nuclear factor 1 homeobox A), also known as HNF1A, a transcription factor involved in the regulation of the expression of several genes such as Glucose Trasporter 1 (GLUT1) and Glucose Transporter 2 (GLLUT2) which can be used as downstream product to identify activated Rac3 in the sense of the disclosure. Additional downstream effectors of Rac1, Rac2 and/or Rac3 can be identified by a skilled person.

In some embodiments herein described, the Rac gene within activated phagocytes is an activated Rac1, Rac-2 and/or Rac3 gene encoding an activated Rac protein comprising mutations enhancing the Rac1 Rac-2 and/or Rac3 properties and activities. Accordingly, the activating mutation of RA C, RAC2 and/or RAC3 described herein generally refers to a mutation in the Rac gene that impairs GAP-mediated GTP hydrolysis thereby resulting in a sustained GTP bound active Rac hence prolonged activation of downstream effectors. In some embodiments, Rac activating mutations can be detected by detection of a downstream product or by detection of the Rac-downstream effector complex. Accordingly, Rac activating mutations can be detected for example by GST pulldown assay using glutathione S-transferase (GST) fused to the PAK1 GTPase-binding domain (GBD) to detect PAK1 binding in western blot with PAK1 antibody. Further, one can also use Anti-RAC2 Rabbit Polyclonal Antibody (ORIGENE) to detect immunofluorescence in RAC2[WT] and RAC2[E62K] expressing HL60 cells. Accordingly, the wording "active Rac genes" as used herein indicates a Rac gene encoding for an active Rac protein in the sense of the disclosure, e.g., a naturally occurring or engineered Rac protein that provide enhanced Rac properties in the sense of the present disclosure.

Exemplary activated Rac proteins in the sense of the disclosure have one or more enhanced Rac properties and may comprise one or more mutations in a Rac protein of any one of SEQ ID NOs 1 to SEQ ID NO: 15. In particular, in some embodiments, an activated Rae protein comprises an amino acid sequence having at least 96%, 97%, 98%, 99, 70%, 99.80%, 99.91% 99.99%, percent identity with any one of SEQ ID NO 1 to SEQ ID NO: 15. More particularly an activated Rac protein can comprise an amino acid sequence having one or more replaced amino acids as well as insertions or deletion as will be understood by a skilled person.

In some embodiments, an activated Rac protein can have one or more mutations (e.g., one or more point mutations) in at least one of the Nucleotide Binding Region Effector Region and/or Lipid Binding Region identifiable by a skilled person upon reading of the present disclosure. In some embodiments, an activated Rac protein can have one or more mutations (e.g., one or more point mutation) in at least one of Switch I, Switch II regions and PM regions also identifiable by a skilled person upon reading of the present disclosure.

In particular, in some embodiments, an active Rac protein in the sense of the disclosure comprise a Rac protein of any one of SEQ ID NO: 1 to SEQ ID NO; 15 including one or more Rac activating mutations of the nucleotide binding region, effector region and/or lipid binding region and exhibiting enhanced Rac properties in the sense of the disclosure (see Example 3. Example 4).

In some embodiments, an active Rac protein in the sense of the disclosure comprise a Rac protein of SEQ ID NO 1 to 15, including one or more Rac activating mutation of at least one of the Switch I region, Switch II region and/or PM regions and exhibiting enhanced Rae properties in the sense of the disclosure. (see Example 3, Example 4). For example, in some embodiments, an activated Rac protein can have SEQ ID NO: 1 or SEQ ID NO: 3, comprising one or more mutations (e.g., one or more point mutation) in at least one of the Nucleotide Binding Region (residues 9-16, 57-61, 115-118), Effector Region (32-40), and/or Lipid Binding Region (190) In addition or in the alternative some embodiments an activated Rac protein can have SEQ ID NO: 1 or SEQ ID NO: 3 comprising one or more mutations (e.g., one or more point nutation in the Switch I region (residues 26-45) and/or Switch II region (residues 59-74) of SEQ ID NO: 1 or SEQ ID NO: 3 (see Examples section). Additional examples are identifiable by a skilled person upon reading of the present disclosure.

In some embodiments, an activated Rac protein has a mutation (e.g., a point mutation) at one or more amino acid residues corresponding to amino acid residue number 11, 12, 28, 29, 30, 34, 62, 63, 92, and/or 157, optionally relative to the amino acid sequence of any one of SEQ ID NO 1 to SEQ ID NO" 15. In some embodiments, a Rac activating mutation can comprise at least one of a D11A, G12V/R, F28L, P29S, P29L, P29Q, PG(29,30)VD, P34H, E62K, D63V N92S, N92T N92I, C157Y mutation relative to any one of SEQ ID NO 1 to SEQ ID NO" 15. (see Example 4). In some of those embodiments, an activated Rac protein has one or more of mutations P29L, P29Q, P34H, N92S and N92T relative to SEQ ID NO: 1. (see Example 4).

In particular in some embodiments, a Rac activating mutation and/or a Rac activated protein in the sense of the disclosure comprises RAC1 (D11A), RAC1 (G12V/R), RAC1 (F28L), RAC1 (P29S), RAC1 (PG(29,30)VD), RAC1 (N92I), and/or RAC1 (C157Y), (see Example 4).

In some embodiments, a Rac activating mutation and/or a Rac activated protein in the sense of the disclosure comprise RAC2 (G12R) RAC2(P29L), RAC2 (P29Q), RAC2 (P34H), RAC2(G12V/R), RAC2 (E62K), RAC2 (D63V), RAC2 (N92S), and/or RAC2(N92T), as will also be understood by a skilled person.

Additional, exemplary Rac activating mutations comprises mutations reported in human patients wherein neutrophils from such patients are hyperactive and exhibit aberrant macropinocytotic vesicles and large vacuoles not seen in cells from healthy controls (Hsu et al. 2019). For example, the Rac2[E62K] mutation impairs both TIAM1-mediated GTP for GDP exchange and p50RhoGAP-mediated GTP hydrolysis. The net effect is prolonged Rac2 activation and interaction with effector proteins such as PAK. The clinically most significant defect due to Rac2 [E62K] is typically immunodeficiency due to reduced numbers of B and T cells. Effects of an activating mutation of the Rac-2 gene can be identified in a mouse model recapitulates the effects found in patients including a >20-fold reduction in CD3+ T cells. The observed B and T cell lymphopenia does not appear to be due to failure of B and T cells to develop in the bone marrow or mature in the thymus and remains unexplained. Neutrophilia was also noted in Rac2 [E62K]. Other activating mutations, such as [G12V] can impair the GTP hydrolysis enzyme activity of Rac2, again resulting in enhanced interaction with effector proteins such as PAK. (see Example 4) In some embodiments, the activating mutation of Rae-2 gene comprises at least one of the following mutations in RAC2:E62K, Q61L, D63V, G12R and G12V. (see Example 4).

In particular, RAC2[E62K] is a heterozygous variant in RAC2 gene that is associated with a dominant phenotype. It is mutation in Glutamate 62 (E62) that lies within the Switch II domain of RAC2 gene. RAC2[E62K] impairs GAP-mediated GTP hydrolysis thereby resulting in a sustained GTP bound active Rac2 hence prolonged activation of downstream effectors (Hsu et al., 2019). Other known activating mutations in Rac2 such as RAC2[Q61L], RAC2 [D63V], RAC2[G12R] and a constitutively active RAC2 [G12V] also impair GDP exchange and GTP hydrolysis in a similar manner (Xu, Wang et al. 1997): (Cave. Strullu et al. 2015; (Lagresle-Peyrou, Olichon et al. 2021).

In embodiments of genetically engineered activated phagocytes herein described, an activated Rac gene can be naturally occurring or engineered in a phagocyte to be placed under the control of a first phagocyte promoter and possibly additional first phagocyte regulatory regions.

The term "phagocyte promoter" refers to a nucleotide sequence that drives or regulates expression in phagocytes.

Promoters specific to mononuclear phagocyte system (MPS) including macrophages, neutrophils, dendritic cells, and osteoclasts will constitute phagocyte promoter. Examples of such promoters include, but are not limited to, CSF-1 promoter, CD68, CD11c, DC-SIGN, DC-STAMP, Langerin, Human Neutrophil Elastase and any synthetic promoter containing elements of phagocyte system designed to achieve high level of expression in phagocytic cells.

In some embodiments, activated phagocytes in accordance of the present disclosure are phagocytes genetically engineered to comprise an activated Rac gene in a configuration allowing constitutive or conditional expression in a genetically engineered phagocyte.

The term "constitutive promoter" refers to an unregulated promoter that allows for continual transcription of its associated genes. Exemplary mammalian constitutive promoters that can be used for expression in mammalian cells include CMV from human cytomegalovirus, EF1a from human elongation factor 1 alpha, SV40 from the simian vacuolating virus 40, PGK1 from phosphoglycerate kinase gene, Ubc from human ubiquitin C gene, human beta actin, CAAG, SynI and others identifiable to those skilled in the art.

The term "conditional promoter" refers to a promoter with activity regulatable or controlled by endogenous transcription factors or exogenous inputs such as chemical or thermal inducers or optical induction. Examples of mammalian conditional promoters include inducible promoters based on exogenous agents such as TET (tetracycline-response elements, TET-ON/TET-OFF), Lac, dCas-transactivator, Zinc-finger-TF, TALENs-ZF Gal4-uas, synNotch and inducible promoters based on endogenous signals TNF-alpha, cFOS and others identifiable to a skilled person.

The term "regulatory sequence" or "regulatory regions" as described herein indicate a segment of a nucleic acid molecule which is capable of increasing or decreasing transcription or translation of a gene within an organism either in vitro or in vivo. In particular, coding regions of the activated Rac genes herein described comprise one or more protein coding regions which when transcribed and translated produce a polypeptide. Regulatory regions of a gene herein described comprise promoters, transcription factor binding sites, binding sites operators, activator binding sites, protein-protein binding domains, RNA binding domains, DNA binding domains, repressors, enhancers, insulators, silencers and additional regulatory regions that can alter gene expression in response to developmental and/or external stimuli as will be recognized by a person skilled in the art.

Regulatory regions controlling expression of a gene in a phagocyte are herein indicated as "phagocyte regulatory regions".

In some embodiments, the configuration of a genetically engineered phagocyte can include constitutive, conditional and/or phagocyte promoters (examples include CSF-1, CD68, p47phox promoter etc.) containing regulatory sequences for cell type specific expression (e.g. macrophage-specific transcription factor PU.1, Ets family transcription factors and STAT1, C/EBP-α, C/EBP-δ, IRF9, KLF6, and NF-κB transcription factors), DNA and RNA-binding proteins (e.g. EWS and FUS/TLS) upstream of naturally occurring, overexpressed or activated Rac genes. The stoichiometric configuration of various genetic elements in the engineered phagocyte can be optimized by introducing a reporter (such as GFP) along with the other genetic elements and assessing the expression of the reporter in different stoichiometric configurations such as by introducing multiple copies of promoters, enhancers, transcription factor binding sites and additional elements identifiable by a skilled person.

"Introducing," "introduce," "introduced" (and grammatical variations thereof) in the context of a polynucleotide and/or polypeptide of interest means presenting a nucleotide sequence of interest (e.g., polynucleotide, a nucleic acid construct, and/or a guide nucleic acid) and/or polypeptide of interest to a host organism or cell of said organism (e.g., a mammalian cell) in such a manner that the nucleotide sequence and/or polypeptide gains access to the interior of a cell.

In some embodiments of a genetically engineered activated phagocyte, a first phagocyte promoter typically contains at least a core promoter (minimal sequence required to properly initiate transcription) upstream of Rac gene. A core promoter can have some or all of the following elements or motifs ordered from 5' to 3': 1) B recognition element (BRE), 2) TATA box motifs, 3) initiator motif (Inr) containing the transcription start site, 4) motif 10 element (MTE) and 5) downstream promoter element (DPE). Although the presence and number of different combinations of elements are allowed in connection with a core promoter, the one containing at least one sequence of each element will be the most preferred for Rae expression.

First additional phagocyte regulatory regions such as promoter proximal elements, upstream activator sequences and enhancers can be required in different number and copies but not necessary for Rac gene expression.

In a genetically engineered activated phagocyte, the first phagocyte promoter controlling the Rac gene can be a constitutive or conditional promoter homologous or heterologous with respect to the phagocyte. However, due to cytotoxic effects that the activated Rac protein could trigger, conditional promoters are preferred. Thus, activated Rac protein can be conditioned by light, heat, or chemical substances such as antibiotics. Promoters conditioned by antibiotics are the most preferred when analyses in vivo and in vitro have to be done.

A "heterologous" or a "recombinant" nucleotide sequence is a nucleotide sequence not naturally associated with a host cell into which it is introduced, including non-naturally occurring multiple copies of a naturally occurring nucleotide sequence. For example, a heterologous polynucleotide encoding a Rac protein or portion thereof can be a nucleic acid sequence that is not naturally present in a phagocytic cell in which it is present and/or can be an additional nucleic acid sequence compared to the presence of a naturally occurring nucleotide sequence in a phagocytic cell in which it is present.

A "homologous" nucleic acid nucleotide sequence, polypeptide or amino acid sequence is a nucleotide sequence naturally associated with a host cell into which it is introduced. A homologous nucleic acid comprises a "native" nucleic acid, nucleotide sequence, polypeptide or amino acid sequence, which refer to a naturally occurring or endogenous nucleic acid, nucleotide sequence, polypeptide or amino acid sequence as will be understood by a skilled person.

In some embodiments, the activated Rac, the phagocyte promoter and the additional phagocyte regulatory regions can be comprised as a part of a gene expression cassette.

The term "gene cassette" as used herein indicated a mobile genetic element that contains at least one gene and a recombination site. Accordingly, a gene cassette can contain a single gene or multiple genes possibly organized in an operon structure. A gene cassette can be transferred from one DNA sequence (usually on a vector) to another by 'cutting' the fragment out using restriction enzymes or transposase, cripr, viral and/or recombinase enzymes and other nucleases and 'pasting' it back into the new context or other molecular biology and cloning techniques (e.g. per, CRISPR, TALENs, ZFN). Gene cassettes can move around within an organism's genome or be transferred to another organism in the environment via horizontal gene transfer.

A "gene expression cassette" is a gene cassette comprising regulatory sequence to be expressed by a transfected cell. Following transformation, the expression cassette directs the cell's machinery to make RNA and proteins. Some expression cassettes are designed for modular cloning of protein-encoding sequences so that the same cassette can be altered to make different proteins. An expression cassette is composed of one or more genes and the sequences controlling their expression. An expression cassette typically comprises at least three components: a promoter sequence, an open reading frame, and a 3' untranslated region that, in eukaryotes, usually contains a polyadenylation site. An expression cassette can be formed by manipulable fragment of DNA carrying and capable of expressing, one or more genes of interest optionally located between one or more sets of restriction sites. Gene expression cassettes as used herein typically comprise further regulatory sequences additional to the prompter to regulate the expression of the gene or genes within the open reading frame herein also indicated as coding region of the cassette.

The terms "transformation" or "transfection" may be used interchangeably and as used herein refer to the introduction of a nucleic acid into a cell. Transformation of a cell may be stable or transient. Thus, in some embodiments, a host cell or host organism may be stably transformed with a polynucleotide/nucleic acid molecule of the invention. In some embodiments, a host cell or host organism may be transiently transformed with a nucleic acid construct of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromosomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a mammal). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genuine of the host organism.

In particular, in embodiments of activated Rac genes herein described, the gene expression cassettes can comprise one or more activated Rac genes and tinder control of regulatory regions capable of operating in the phagocyte and are thus configured to provide an activated phagocyte.

The terms "under control" or "operative connection" as used herein indicate an arrangement of elements in a combination enabling production of an appropriate effect. With respect to genes and regulatory sequences an operative connection indicates a configuration of the genes with respect to the regulatory sequence allowing the regulatory sequences to directly or indirectly increase or decrease transcription or translation of the genes.

Regulatory sequences used in gene expression cassettes herein described, are selected based on the individual providing the phagocyte. In preferred embodiments, wherein the individual is a manual, the regulatory regions are selected to mammalian regulatory regions and are configured to operate in a mammalian cell.

Exemplary regulatory regions capable of operating in mammalian cells comprise promoters, enhancers, silencers, terminators, regulators, operators, ribosome binding/entry sites, and riboswitches, among others known in the art. Regulatory regions capable of operating in a mammalian host can be selected by a skilled person following selection of the mammalian host of interest. Exemplary constitutive and inducible mammalian promoters and operators suitable for regulating expression of activated Rac genes in a mammalian host are identifiable by those skilled in the art and described herein.

In some embodiments, activated phagocytes are engineered to comprise one or more naturally occurring or engineered, activated or non-activated Rac gene under control of regulatory regions configured to allow expression of activating expression levels resulting in enhanced Rac properties in the sense of the disclosure.

In some of those embodiments, a configuration desired to obtain a high level of expression of active Rac in macrophages can be performed to include a macrophage specific promoter (MSP) or a synthetic promoter designed for high expression in macrophages (SP146) with regulatory regions such as enhancers, macrophage-specific transcription factor PU.1 upstream of naturally occurring, overexpressed or activated Rac genes, (e.g. Rac2E62K). The stoichiometric configuration of various genetic elements can be optimized by introducing a reporter (such as GFP fused to the promoter) along with the other genetic elements and assessing the expression of the reporter in different stoichiometric configurations (such as introducing multiple copies of promoters, enhancers, transcription factor binding sites etc.) to obtain a higher or the highest level of expression as will be understood by a skilled person.

In some embodiments, increased expression can be obtained by inserting in a phagocyte a plurality of cassettes expressing a same or different non-activated Rac gene and/or activated Rac gene in the sense of the present disclosure.

In an exemplary embodiment, a Rac expression cassette for proper expression and activation of Rac protein in phagocytic cells can comprise at least one core promoter and Ra-gene. The number and presence of different regulatory regions into that cassette are optional.

In embodiments herein described, activated phagocytic cells expressing an activated Rac gene comprising an activating mutation show increased phagocytosis capability and increased ability to engulf target cells and/or to increase trogocytosis cells. Increased phagocytosis as well as ability to engulf target cells and to perform trogocytosis can be detected with methods known to a skilled person.

For example, in some embodiments, engulfment in a co-culture experiment with macrophages and target cells, can be detected in live and fixed imaging and quantified using flow cytometry. In particular, different fluorescently labelled macrophage (e.g. expressing an active Rac protein—such as Rac2E62K— fused to a first label-such as GFP) and target cells (e.g. Jurkat T cells expressing fusion protein with a second label—such as HA-mCherry) can be sorted and single (e.g. either GFP or mCherry) and dual positive (e.g. GFP and mCherry) fluorescent cells can be sorted. The dual positive cells (e.g. GFP and mCherry-positive cells) will represent the population of macrophages engulfing target cells. The experiment can be set up with control macrophages (only expressing the first label—e.g. GFP), macrophages expressing non-activated Rac protein—e.g. RAC2. WT fused to the first label—e.g. GFP) and macrophages expressing RAC2 E62K fused to GFP each with target cells separately. Percentage of dual positive cells in each case can be assessed and normalized to the controls to measure the engulfment percentage. A higher engulfment percentage in non-activated Rac (e.g. RAC2 WT) or activated Rac (e.g. RAC2E62K) will represent increased engulfment ability/phagocytosis capacity. Similarly, trogocytosis events can be also be quantified in live imaging experiments. Trogocytosis events can be recorded, measured by dedicated algorithms/programs and normalized to controls to measure the trogocytosis percentage.

Additional tests suitable to identify trogocytosis, engulfment and in general increased phagocytosis of a phagocyte comprise Incucyte Live-Cell Analysis System which can be used to perform real-time, automated phagocytosis/trogocytosis analysis, and High Content Analysis (H-CA) which can provide as another high sensitivity/low background analysis technique to measure phagocytosis, as well as additional tests identifiable by a skilled person.

In an exemplary embodiment, differentiated HL60 Rac2 [E62K] macrophages displayed increased engulfment of immortalized Jurkat leukemic T-cells compared to vehicle control and RAC2[WT] within 24 hrs of co-culture. Some Rac2 [E62K] macrophages are able to engulf more than one T-cell suggesting that Rac2 [E62K] increased the engulfment capacity of these macrophages (see Appendices of U.S. provisional application No. 63/126,379 filed on Dec. 16, 2020 incorporated by reference in its entirety). Increased frequency of stable cell-cell contacts between Rac2[E62K] expressing macrophages and T-cells were also observed after washing out unbound cells in co-culture, indicating an increase in 'trogocytosis' like event reported earlier in neutrophils and macrophages (Matlung, Babes et al. 2018) (Morrissey, Williamson et al. 2018).

In some embodiments, a genetically engineered activated phagocyte of the present disclosure comprises a Rac gene encoding a Rac protein, the Rac gene under control of a third phagocyte promoter and third additional phagocyte regulatory regions in a configuration allowing an expression of the activate Rac gene in the activated phagocytic cell at an activating expression level.

In some embodiments a genetically engineered activated phagocyte comprises a Rac genetic circuit, in which molecular components are connected one to another in accordance with a circuit design by activating, inhibiting, binding, or converting reactions to form a fully connected network of interacting components, wherein in the Rac genetic circuit expression of an activated Rac gene or an increased level of expression of a Rac gene occurs when the Rac genetic circuit operates according to the circuit design in response to a trigger molecular component within the activated phagocyte.

The term "molecular component" as used in connection with the Rac genetic circuits described herein indicates a chemical compound or a structure comprised of a plurality of chemical compounds comprised in a cellular environment. Exemplary molecular components thus comprise polynucleotides, such as ribonucleic acids or deoxyribonucleic acids, polypeptides, polysaccharides, lipids, amino acids, peptides, sugars and/or other small or large molecules and/or polymers that can be found in a cellular environment. In some embodiments described herein, a molecular component of a Rac genetic circuit is a Rac protein.

The term "genetic molecular component" as used herein indicates a molecular unit formed by a gene (possibly comprising or formed by a cluster of genes), an RNA transcribed from the gene or a portion thereof and optionally a polypeptide or a protein translated from the transcribed RNA. In genetic circuits herein described, the biochemical reactions connecting the genetic molecular component to another molecular component of the circuit can involve any one of the gene, the transcribed RNA and/or the polypeptide forming the molecular component.

A gene comprised in a genetic molecular component is a polynucleotide that can be transcribed to provide an RNA and typically comprises coding regions as well as one or more regulatory sequence regions, which is a segment of a nucleic acid molecule which is capable of increasing or decreasing transcription or translation of the gene within an organism either in vitro or in vivo. In particular, coding regions of a gene herein described can comprise one or more protein coding regions which when transcribed and translated produce a polypeptide, or if an RNA is the final product only a functional RNA sequence that is not meant to be translated. Regulatory regions of a gene herein described comprise promoters, transcription factor binding sites, operators, activator binding sites, repressor binding sites, enhancers, protein-protein binding domains, RNA binding domains, DNA binding domains, silencers, insulators and additional regulatory regions that can alter gene expression in response to stimuli as will be recognized by a person skilled in the art.

An RNA of a genetic molecular component comprises any RNA that can be transcribed from a gene, such as a messenger ribonucleic acid (mRNA), short interfering ribonucleic acid, or ribonucleic acid capable of acting as a regulating factor in the cell. mRNA comprised in a genetic molecular component comprises regions coding for the protein as well as regulatory regions. mRNA can have additional control elements encoded, such as riboregulator sequences or a protein binding aptamer sequence placed upstream of the gene so the protein blocks ribosomes and conditionally prevents translation. Other RNAs that serve regulatory roles that can comprise the genetic molecular component include riboswitches, aptamers (e.g. malachite green, Spinach), aptazymes, guide CRISPR RNAs, and other RNAs known to those skilled in the art.

A protein comprised in a molecular component can be proteins with activating, inhibiting, binding, converting, or reporting functions. Proteins that have activating or inhibiting functions typically act on operator sites encoded on DNA but can also act on other molecular components. Proteins that have binding functions typically act on other proteins but can also act on other molecular components. Proteins that have converting functions typically act on small molecules and convert small molecules from one small molecule to another by conducting a chemical or enzymatic reaction. Proteins with converting functions can also act on other molecular components. Proteins with reporting functions have the ability to be easily detectable by commonly used detection methods (absorbance, fluorescence, for example), or otherwise cause a reaction on another molecular component that causes easy detection by a secondary assay (e.g. adjusts the level of a metabolite that can then be assayed for. The activating, inhibiting, binding, converting, or reporting functions of a protein typically form the interactions between genetic components of a genetic circuit. Exemplary proteins that can be comprised in a genetic molecular component comprise monomeric proteins and multimeric proteins, proteins with tertiary or quaternary structure, proteins with linkers, proteins with non-natural amino acids, proteins with different binding domains, and other proteins known to those skilled in the art.

The term "cellular molecular component" indicates a molecular component not encoded by a gene, or indicates a molecular component transcribed and/or translated by a gene but comprised in the circuit without the corresponding gene. Exemplary cellular components comprise polynucleotides, polypeptides, polysaccharides, small molecules and additional chemical compounds that are present in a cellular environment and are identifiable by a skilled person. Polysaccharides, small molecules, and additional chemical compounds can include, for example, NAD, FAD, ATP, GTP, CTP, TTP, AMP, GM P, ADP, GDP, Vitamin B1, B12, citric acid, glucose, pyruvate, 3-phosphoglyceric acid, phosphoenolpyruvate, amino acids, PEG-8000, FiColl 400, spermidine, DTT, b-mercaptoethanol maltose, maltodextrin, fructose, HEPES, Tris-Cl, acetic acid, aTc, IPTG, 3OC12HSL, 30C61-HSL, vanillin, malachite green, Spinach, succinate, tryptophan, and others known to those skilled in the art. Polynucleotides can include RNA regulatory factors (small activating RNA, small interfering RNA), or "junk" decoy DNA that either saturates DNA-binding enzymes (such as exonuclease) or contains operator sites to sequester activator or repressor enzymes present in the system. Polypeptides can include those present in the genetic circuit but not produced by genetic components in the circuit, or those added to affect the molecular components of the circuit.

In embodiments of genetic circuits herein described, one or more molecular components is a recombinant molecular component that can be provided by genetic recombination (such as molecular cloning) and/or chemical synthesis to bring together molecules or related portions from multiple sources, thus creating molecular components that would not otherwise be found in a single source.

In some embodiments, the Rac genetic circuits described herein can comprise a plurality of genetic molecular components that function as Boolean logical operators in genetic circuit designs known to those skilled in the art, such as those described in ((Buchler, Gerland et al. 2003). (Silva-Rocha and de Lorenzo 2008) As would be understood by persons skilled in the art, Boolean logic is a branch of algebra in which the values of the variables are the truth values 'true' and "false", usually denoted by the digital logic terms '1' and '0' respectively. In contrast with elementary algebra where the values of the variables are numbers, and the main operations are addition and multiplication, the main operations of Boolean logic are the conjunction 'AND', the disjunction 'OR', and the negation 'NOT'. As understood by those skilled in the art, it is thus a formalism for describing logical relations in the same way that ordinary algebra describes numeric relations.

Accordingly, the term "AND gate" refers to a digital logic gate that behaves according to the truth table shown in Table 2. A 'true' output (1) results only if both the inputs to the AND gate are 'true' (1). If neither or only one input to the AND gate is 'true' (1), a 'false' (0) output results. Therefore, the output is always 0 except when all the inputs are 1.

TABLE 2

'AND gate' truth table:

| Input | | Output |
|---|---|---|
| A | B | A AND B |
| 0 | 0 | 0 |
| 0 | 1 | 0 |
| 1 | 0 | 0 |
| 1 | 1 | 1 |

In particular, the term "AND gate" as used herein refers to the logical relation between two genetic molecular components in a GVR genetic circuit, wherein inputs 'A' and 'B' in Table 1 are two biochemical events, and the output 'A AND B' in Table 2 is the expression of the activated Rac gene and/or the expression of a Rac gene at activating expression levels alone or in combination with one or more additional targeting ligands such as a Chimeric Antigen Receptor (CAR) as will be understood by a skilled person upon reading of the present disclosure.

For example, in some embodiments of an "AND gate" comprised in a Rac genetic circuit described herein, the Rac genetic circuit comprises a plurality of genetic molecular components wherein at least a first genetic molecular component comprises a first cassette expression an activated Rac gene, and at least a second genetic molecular component comprises a CAR, wherein together the activated Rac gene expressed from the first genetic molecular component and the CAR expressed by the second genetic molecular components are configured to operate in combination in the activated phagocyte in the sense of the disclosure.

In these embodiments, activation of both the first AND second genetic molecular component is required for the output of the combined activated Rac and CAR expression in the genetic circuit when the genetic circuit operates according to the design of the genetic circuit. For example, the first and second genetic molecular components can comprise promoters that are activated by two or more biochemical events in the phagocyte cell comprising the Rae genetic circuit.

The term "OR gate" refers to a digital logic gate that behaves according to the truth table shown in Table 3. A 'true' output (1) results if either of the inputs to the OR gate are 'true' (1).

TABLE 3

| 'OR gate' truth table: | | |
|---|---|---|
| Input | | Output |
| A | B | A OR B |
| 0 | 0 | 0 |
| 0 | 1 | 1 |
| 1 | 0 | 1 |
| 1 | 1 | 1 |

In particular, the term "OR gate" as used herein refers to the logical relation between two genetic molecular components in a Rac genetic circuit, wherein inputs 'A' and 'B' in Table 2 are two biochemical events, and the output 'A OR B' in Table 2 is the expression an activated Rac gene and/or Rac gene at activating expression levels in combination with one or more CARs.

For example, in some embodiments of an "OR gate" comprised in a Rac genetic circuit described herein, a promoter operatively connected to an activated Rac gene and a CAR comprised in a genetic molecular component of a Rac genetic circuit that is activated by biochemical events A OR B would result in the output of the combined expression of activated Rac gene and a CAR in the Rac genetic circuit. For example, the promoter is activated by binding of either of two different transcriptional activators which are both expressed for example at the same of tumor treatment.

Additional information concerning genetic circuits, and related molecular components can be found in (Del Vecchio and Murray 2014)) incorporated herein by reference in its entirety as will be understood by a skilled person.

In some embodiments, a phagocyte is a cell from an individual such as, an individual to be administered a genetically engineered phagocyte, vector, and/or composition as described herein and/or an individual to be treated by a method as described herein.

In some embodiments, a genetically engineered activated phagocytic cell herein described, can be engineered or further engineered to comprise a nucleotide sequence encoding a chimeric antigen receptor ("CAR") and a Rac gene comprising an activating mutation.

The term "chimeric antigen receptor" as used herein refers to an artificial cell surface receptor that is designed to bind to certain proteins on cancer cells. The chimeric antigen receptor can help immune cells such as T cells or macrophages find and kill cancer cells that have the specific protein the receptor is designed to bind. For example, phagocytes such as macrophages or monocytes can be removed from a blood, tumor, or ascites fluid of a patient and modified so that they express the chimeric antigen receptors specific to a particular form of antigen on tumor cells. Therefore, a CAR can target cancers by redirecting a phagocyte such as monocyte or macrophage expressing the CAR specific for tumor associated antigens.

In embodiments of activated phagocyte of the present disclosure and related vector compositions, methods and systems herein described, CARs can comprise an intracellular activation domain, a transmembrane domain and an extracellular domain comprising a tumor associated antigen binding region as a person skilled in the art will understand. In some examples, CARs can comprise fusions of single chain variable fragments (scR) derived monoclonal antibodies, fused to CD3-zeta transmembrane and intracellular domain. The specificity of CAR designs can be derived from ligands of receptors.

Examples of CARs suitable to be used in connection activated phagocyte of the present disclosure and related vector compositions methods and systems herein described, include CARs that binds to CD3. CD19, CD22, CD30, CD123, B cell maturation antigen (BCMA), GD2, mesothelin, EGVRvIII, HER2, e-MET, PD-L1, and other tumor associated antigen.

Exemplary of tumor associated antigens that CARs activated phagocyte of the present disclosure and related vector compositions, methods and systems herein described, can bind to include mesothelin, EGFRvIII, TSHR, CD19, CD123, CD22, CD30, CD1 S, CS-1, CLL-1, CD33. GD2. GD3. BCMA. Tn Ag, prostate specific membrane antigen (PSMA), ROR1, FLT3, FAP, TAG72, CD38, CD44v6, CEA, EPCAM, B7H3, KIT, IL-13Ra2, interleukin-11 receptor a (IL-11Ra), PSCA, PRSS21, VEGFR2, LewisY, CD24, platelet-derived growth factor receptor-beta (PDGFR-beta), SSEA-4, CD20, Folate receptor alpha (FRa), ERBB2, (Her2/neu), MUC1, epidermal growth factor receptor (EGFR), NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SAR T3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In some embodiments, activated phagocyte of the present disclosure and related vector compositions methods and systems herein described can comprise CAR configured to bind to molecules expressed on the surface of tumor cells, including CD20, CD22, CD33, CD2. CD3, CD4, CD5, CD7, CD8, CD45, CD52, CD38, CS-1, TIM3, CD123, mesothelin, folate receptor, HER2-neu, epidermal-growth factor receptor, and epidermal growth factor receptor. In some embodiments, the immune activating receptor is a CAR (e.g., anti-CD19-4-1BB-CD3ζ CAR). In certain embodiments, the immune activating receptor comprises an antibody or antigen-binding fragment thereof (e.g., scFv) that binds to molecules expressed on the surface of tumor cells, including but not limited to, CD20, CD22, CD33, CD2, CD3, CD4, CD5, CD7, CD8, CD45, CD52, CD38, CS-1, TIM3, CD123, mesothelin, folate receptor, HER2-neu, epidermal-growth factor receptor, and epidermal growth factor receptor.

In embodiments, wherein the activated phagocyte of the present disclosure and related vector compositions, methods and systems herein described comprise CAR the genetically engineered activated phagocyte further comprises a chimeric antigen receptor (CAR) under control of a second phagocyte promoter and under second additional phagocyte regulatory regions in a configuration allowing expression of the CAR in the activated phagocytic cell. The second phagocyte promoter and second additional phagocyte regulatory regions used in regulating the expression of CAR can be the same as or different from the first and/or third phagocyte promoter and first and/or third additional phagocyte regulatory regions used in regulating the expression and activation of Rac gene.

Suitable second phagocyte promoters, and additional second phagocyte regulatory regions as well as embodiments, of tumor associated antigens CAR can bind to, and methods of engineering a cell to express CAR can be found in US20200239592, US20200055917, U.S. Pat. No. 10,125,193, and published literatures such as "Chimeric antigen receptors that trigger phagocytosis" by Meghan Morrissey at al., which are incorporated by reference in their entirety. (Morrissey, Williamson et al. 2018) (Morrissey and Vale 2019).

Additional targeting ligand can be presented on the phagocyte in addition or in place of CAR-P as will be understood by a skilled person. Additional targeting ligands comprise molecules configured to associate with any molecule presented on a target cell of interest, such as a target associated with an organ, tissues, extracellular matrix, or intracellular region of a target cell of interest. In some embodiments, additional target can be associated with a particular state of a target cell, such as a cancerous condition.

A targeting ligand presented in activated phagocyte herein described can be specific to one target, or be configured to bind multiple target molecules Suitable targets molecule can comprise a protein, (e.g. a receptor a tumor-marker, a transmembrane protein, an enzyme, or an antibody) a nucleic acid, such as a DNA, or RNA, or a carbohydrate, such as a monosaccharide, disaccharide, or polysaccharide that can be for example, present on the surface of a cell. Exemplary targeting ligand comprise an RGD-containing peptide, a small molecule (e.g. a peptide) mimetic ligand), or an antibody or antibody fragment specific for a particular target. For example in some embodiments, a bivalent antibody specific to macrophages and target cell antigen in addition or in place of CARs to target cancerous cells (Feuerstein n.d.).

In embodiments, wherein a genetically engineered activated phagocyte as described herein, further comprises a CAR gene in a configuration allowing the related expression therefore possess the therapeutic effect directed against target cells that specifically bind the antigen binding domain of the CAR such the anti-tumor effect against tumor cells. In some of those embodiments, a CAR-expressing activated phagocytes herein described further comprise an activating mutation in Rac and/or a mutation that turns the Rac gene into a constitutively active gene.

For example in exemplary embodiments, a phagocyte containing an activated Rae gene cassette (phagocyte promoter and regulatory regions along with active Rac gene or mutations with dominant activating effects on Rac gene) can further be transfected with CAR-constructs to allow its therapeutic effect using the CAR-technology. Chimeric Antigen Receptors for Phagocytosis (CAR-Ps) contain the extracellular single-chain antibody variable fragment (scFv) recognizing the B cell antigen CD19 (αCD19) and the CD8 transmembrane domain present in the αCD19 CAR-T along with the cytoplasmic domains of phagocytic receptors Megf10. This construct will be introduced to the active phagocytes using lentiviral or adenoviral transfection method. Additionally, CAR-P expressing phagocytic cells can be transfected with the activated Rac gene cassette to allow simultaneous expression of CAR-P and active Rac in phagocytes. Similarly, CAR-M construct (another CAR-expressing construct) can be co-transfected with the activated Rac gene cassette in phagocytic cells to harness their anti-tumoral therapeutic effects.

In particular, phagocyte transfected with CAR according to any one of the methods and/or using anyone of the compositions described in can be found in US20200239592. US20200055917, U.S. Pat. No. 10,125,193 and in as well as in (Morrissey, Williamson et al. 2018) (Morrissey and Vale 2019) can be a naturally occurring activated phagocyte and/or further be engineered to provide an active Rac gene and/or Rac at activating expression levels, as will be understood by a skilled person upon reading of the present disclosure.

In some embodiments herein described, a method of producing a genetically engineered phagocytic cell comprises introducing into a phagocytic cell an active Rac gene herein described, under the control of a phagocyte promoter, preferably a constitutive promoter and under the control of one or more additional phagocyte regulatory regions in a configuration allowing expression of the Rac gene in a phagocyte.

In addition, or in the alternative when the phagocyte is a naturally occurring active phagocyte herein described, the method can further comprise introducing into a phagocytic cell a chimeric antigen receptor (CAR) under control of a second phagocyte promoter and optionally under control of second additional phagocyte regulatory regions.

In embodiments to provide an activated phagocyte herein described the introducing can be performed by transfecting or transforming the phagocyte with a suitable Rac expression vector. The term "transfected" or "transformed" or "transduced" as used herein refers to a process by which exogenous nucleic acid is transferred or introduced into the phagocytic cell.

An "expression vector" in the sense of the disclosure indicates a construct configured to introduce a specific gene into a target cell and to produce the protein encoded by the gene using the target cell mechanism. An expression vector typically comprises elements necessary for gene expression such as a promoter, a correct translation initiation sequence such as a ribosomal binding site and start codon, a termination codon, and a transcription termination sequence. An expression vector can also comprise additional elements such as an origin of replication, a selectable marker, and a suitable site for the insertion of a gene such as the multiple cloning sites. A vector in the sense of the disclosure can include sequences that direct autonomous replication in a cell or may include sequences sufficient to allow integration into host cell DNA.

Exemplary expression vectors that can be used in methods and systems herein described include plasmids (e.g., DNA plasmids or RNA plasmids), transposons, cosmids, bacterial artificial chromosomes viral vectors. In some embodiments, a vector is a gene delivery vector such as retroviral vectors, lentiviral vectors and adeno-associated vectors. In some embodiments, a vector is used as a gene delivery vehicle to transfer a gene into a cell Expression vectors can also include non-viral gene delivery nanomaterial such as polymeric nanoparticles or liposomes, and others identifiable by a person skilled in the art.

Retroviral vectors are retroviruses genetically engineered to deliver therapeutic genes rather than retroviral genes to target cells. Retroviral vector can be produced by inserting the transgene in place of part of the viral genome, and a preparation of infectious viral particles is produced by introducing the recombinant virus into tissue culture cells.

The term "lentiviral vector" refers to a vector derived from at least a portion of a lentivirus genome, including especially a self-inactivating lentiviral vector as provided in (Milone, Fish et al 2009). Other examples of lentivirus vectors include the LENTIVECTOR® gene delivery technology from Oxford BioMedica, the LENTIMAX™ vector system from Lentigen and the like.

Accordingly, in some embodiments herein described, a Rac expression vector comprises a gene encoding a Rac gene in a constitutively active form and appropriate regulatory elements such as promoters, enhancers, and post-transcriptional and post-translational regulatory sequences that are compatible with the target cell expressing the gene as would be understood by a skilled person.

In some embodiments, Rac expression vector is configured for genomic insertion allowing long-term overexpression or activation of Rac gene into any phagocytic cells (neutrophils, monocytes and monocyte-derived macrophages and monocyte-derived dendritic cells). In those embodiments genomic insertion is performed preferentially by stable transfection. Thus, in some of those embodiments, lentiviral transduction is preferred over physical or chemical transfections or adenoviral transduction. In preferred embodiments, lentiviral transduction is expected to be used effectively in vivo for Rac gene delivery and will permit stable expression in dividing and non-dividing cells as well as will be understood by a skilled person.

In some embodiments, Rac expression vectors containing at least a core promoter followed by Rac gene can be used to engineer a Rac gene to include one or more activating Rac mutations in Rac gene that have been previously described. Mutations in Rac gene can be generated by site-directed mutagenesis leading to the substitution of an amino acid specific in Rac protein.

Transfection methods reported in connection with CAR transfection such as the ones described in US20200239592, US820200055917, U.S. Pat. No. 10,125,193 and in as well as in (Morrissey, Williamson et al 2018) (Morrissey and Vale 2019) are also expected to be usable to engineer phagocytes to provide active Rac gene, activating Rac expression levels and/or expression of one or more CARs.

In some embodiments, a nucleic acids encoding CAR and mutated Rac genes herein described can be introduced into a cell using viral vectors such as retroviral and lentiviral vector constructs as well as adeno-associated vectors or non-viral gene delivery approaches as will be understood by a person skilled in the art.

In one example, RAC2(RAC2) (NM_002872) Human Untagged Clone (ORIGENE) and Rac2 [E62K] (Hsu, Dorkó et al. 2019)) were cloned in pCW57 vector using Nhe and Age sites. Lentiviral transfection of these constructs was carried out in HL60 cells. For macrophage differentiation, HL60 cells were seeded at a density of $5\times10^5$ cells/mL in RPMT 1640 plus L-glutamine and 10% heat-inactivated fetal bovine serum (FBS) media in a coverslip coated 6-well plate and treated with doxycycline and 32 nM 12-O-tetradecanoylphorbol-13-acetate (TPA) for 48 h. Equal density of Jurkat T-cells were labeled with Cell Tracker Red (Invitrogen) and co-cultured with differentiated macrophages for 24 h for phagocytosis assay. These co-culture experiments were also repeated with HA-mCherry tagged Jurkat T-cells and found consistent results (see Example 6).

The term Rac expression vector indicates an expression vector comprising an activated Rac gene possibly with a phagocyte promoter and additional phagocyte regulatory regions within a gene expression cassette. In some embodiments a Rac expression vector further comprises a CAR gene and related phagocyte prompter and additional phagocyte regulatory sequences possibly within a CAR gene expression cassette.

In some embodiments, the activated Rac gene and/or the CAR gene can be introduced with viral vectors that comprise adeno-associated viral vectors ("AAV"). AAVs are nonenveloped, single-stranded DNA viruses of the *Dependoparvovirus* genus of the Paroviridae family. AAVs are innately nonpathogenic, poorly immunogenic, and broadly tropic, making them attractive gene delivery candidates for virus-based gene therapies. AAV vectors have shown to stably transfect mammalian cells without integration into the target genome.

Exemplary suitable AAVs comprise AAVs of various serotypes can be used as vectors for carrying chemogenetic protein genes. AAV serotypes are identified based on their interacting glycan moieties that mediate the initial attachment of AAVs to the cell surface. Examples of AAV serotypes include AAV serotype 1 ("AAV1"), AAV2, AAV3, AAV5, AAV6. AAV9 and other serotypes identifiable to a person skilled in the art such as AAV7, AAV8, AAV11, AAV-DJ.

In other embodiments, the nucleic acids can be directly transfected into a phagocyte.

In some embodiments, the CRISPR/Cas system is used to induce targeted genetic alterations in the Rac gene as will be understood by a person skilled in the art. Method of modifying targeted genes using CRISPR systems and would be identifiable by a skilled person.

In other embodiments, the nucleic acids can be electroporated into a cell. Detailed methods for electroporation are described, e.g., in (Roth, Puig-Saus et al. 2018) (Van Tendeloo, Willems et al. 2000).

In some embodiments, the Rac expression vectors herein described can be transferred into a host cell by physical, chemical, or biological means herein described as well as others known to a person skilled in the art. The production of any of the introduced proteins can be verified by sequencing. Expression of the full-length proteins may be verified using immunoblot, immunohistochemistry, flow cytometry, or other technology well known and available in the art.

In some embodiments, one or more active Rac genes can be cloned in a conditional, doxycycline inducible (Tet ON), lentiviral, mammalian expression vector (e.g. pCW57), and CAR-P module cloned in a lentiviral vector (such as derived from pHRSIN-CSGW), or CAR-M module cloned in a lentiviral or adenoviral vectors (such as containing pTRPE lentiviral backbone or pAd5f35 adenoviral backbone) will be stably expressed in phagocytes. Phagocytes containing either of these CAR modules will be transfected with the activated Rac gene cassette module to allow co-expression of these constructs. Additional, suitable methods for transforming or transfecting host cells can be found in ((Sambrook, Fritsch et al. 1989) and other standard molecular biology laboratory manuals as will be understood by a skilled person.

In some embodiments, the Rac expression vectors and/or the genetically engineered cells can be comprised in a composition together with a compatible vehicle.

The term "vehicle" as used herein indicates any of various media acting usually as solvents, carriers, binders, or diluents for the expression vectors, genes, contrast agent and/or chemical actuators herein described that are comprised in the composition as an active ingredient. In particular, the composition including the expression vectors, genes, contrast agent and/or chemical actuators can be used in one of the methods or systems herein described.

In some embodiments, the vehicle is a pharmaceutically acceptable vehicle and the composition is a pharmaceutically acceptable composition.

As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained.

Suitable vehicles for injectable composition comprise a solvent or dispersion medium containing, for example, water, ethanol, polyol (for example, glycerol, propylene glycol, and liquid polyethylene glycol, and the like), and suitable mixtures thereof.

Suitable vehicles for oral composition comprise inert diluent or an edible carrier and excipients which can be combined with the active ingredients in the form of tablets, pills, troches, or capsules, e.g., gelatin capsules. Pharmaceutically compatible binding agents, and/or adjuvant materials can be included as part of the composition, such as microcrystalline cellulose, gum tragacanth or gelatin and additional binding agents and/or adjuvant identifiable by a skilled person.

Suitable vehicles for aerosol spray used for inhalation from pressured container or dispenser which contains a suitable propellant, e.g., a gas such as carbon dioxide, or a nebulizer and are expected to be formulated and/or administered with methods such as the ones described in U.S. Pat. No. 6,468,798, incorporated herein by reference in its entirety.

Suitable vehicles for transmucosal or transdermnal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Suitable vehicles for composition in the form of suppositories (e.g., with conventional suppository bases such as cocoa butter and other glycerides) or retention enemas for rectal delivery.

Preferably pharmaceutical composition carriers that will protect the phagocyte, polypeptides and nucleic acids molecules against rapid elimination from the body, such as a controlled release formulation, including implants and microencapsulated delivery systems.

In embodiments of the disclosure, the activated phagocyte of the disclosure or the related vectors and compositions can be administered in a method of treating an individual by engulfment and/or trogocytosis of a target cell. In particular, methods of the can be used to treat individuals who have, who are suspected of having, or who may be at high risk for developing one or more health conditions or disorders for which trogocytosis and/or engulfment of a target cell is known or expected to have therapeutic effect.

The term "target cell" as used herein indicates cells to be recognized and eliminated by the activated phagocytes of the disclosure. Examples of target cells include tumor cells, bacteria, virus-infected cells, viral particles, senescent cells and other identifiable to a person skilled in the art. In some embodiments, target cell also includes neurons that are non-functional or dying due to accumulation of abnormal forms of Tau or beta-amyloid.

Exemplary conditions that may be treated with a phagocyte, vector, and/or composition of the disclosure comprise, acute and/or chronic infections, inflammatory diseases, immune diseases, and/or cancers. In some embodiments, the methods disclosed herein are useful in treating one or more health conditions or disorders by enhancing (e.g. increasing) the removal of cells from the individual's body through enhanced phagocytosis including removal of not only infected, transformed, malignant, apoptotic, damaged and/or necrotic cells, but also of living cells (such a tumor cell, cancer cell, or other cells targeted by activated phagocyte in the sense of the disclosure).

The method comprises administering to the individual a therapeutically effective amount of a Rac active pharmaceutical composition herein described. In particular, in method herein described, activated phagocytes with active Rac or activating Rac level are administered to the individual either alone or in combination with a receptor that would impart specificity for target cells identified in connection with the conditions to be treated.

In particular in preferred embodiments, methods of the disclosure comprise administering a therapeutically effective amount of a Rac active phagocyte, vector and/or composition herein described in combination with a CAR (see US2020/0239592 incorporated by reference in its entirety).

In some embodiments, the target cell is a tumor cell and engulfment and/or trogocytosis of the target cell can be performed by a method of treating a tumor in a subject using the expression vectors and/or activated phagocyte of the disclosure preferably in combination with one or more CARs.

The term "tumor" or "cancer" as used herein refers to a disease characterized by the rapid and uncontrolled growth of aberrant cells. The aberrant cells may form solid tumors or constitute a hematological malignancy. Cancer cells can spread locally or through the bloodstream and lymphatic system to other parts of the body. There are no specific limitations with respect to the cancers which can be treated by the compositions and methods of the present disclosure. Non-limiting examples of suitable cancers include ovarian cancer, renal cancer, breast cancer, prostate cancer, liver cancer, brain cancer, lymphoma, leukemia, cervical cancer, skin cancer, pancreatic cancer, colorectal cancer, lung cancer and the like. Other cancers that can be suitable treated with the compositions and methods of the present disclosure include, but are not limited to, AML, ALL, CML, adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectum cancer, endometrial cancer, esophagus cancer, Ewing's family of tumors (e.g. Ewing's sarcoma), eye cancer, transitional cell carcinoma, vaginal cancer, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, gallbladder cancer, gastrointestinal carcinoid tumors, gastrointestinal stromal tumors, gestational trophoblastic disease, Hodgkin's lymphoma, Kaposi's sarcoma, kidney cancer, laryngeal and hypopharyngeal cancer, liver cancer, lung cancer, lung carcinoid tumors, brain cancers, central nervous system (CNS) cancers, peripheral nervous system (PNS) cancers, breast cancer, cervical cancer, childhood Non-Hodgkin's lymphoma, colon and rectum cancer, Non-Hodgkin's lymphoma, malignant mesothelioma, multiple myeloma, myelodysplastic syndrome, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g., uterine sarcoma), transitional cell carcinoma, vaginal cancer, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g., uterine sarcoma), transitional cell carcinoma, vaginal cancer, vulvar cancer, mesothelioma, squamous cell or epidermoid carcinoma, bronchial adenoma, choriocarcinoma, head and neck cancers, teratocarcinoma, or Waldenstrom's macroglobulinemia. Particularly suitable cancers include, but are not limited to, breast cancer, ovarian cancer, lung cancer, pancreatic cancer, mesothelioma, leukemia, lymphoma, brain cancer, prostate cancer, multiple myeloma, melanoma, bladder cancer, bone sarcomas, soft tissue sarcomas, retinoblastoma, renal tumors, neuroblastoma, and carcinomas. (source US2020/0239592 incorporated by reference in its entirety).

In some embodiments of treating Alzheimer's disease, the expression vectors and/or activated phagocyte of the disclosure can trigger the phagocytosis of amyloid-beta by macrophages, thus resulting in a clearance of amyloid-beta In those embodiments, activated phagocyte administered are expected to comprise activated macrophage and in particular activated glial cells as will be understood by a skilled person upon reading of the present disclosure. Enhanced Rac properties in the macrophage and in particular in the glial cells are expected to result in an enhanced ability of the glial cells to engulf and/or perform trogocytosis of amyloid beta as will be understood by a skilled person upon reading of the present disclosure (see Example 20).

In particular, in some embodiments the method comprises administering to the subject a therapeutically effective amount of a pharmaceutical composition comprising the activated phagocytes and/or an activated Rac expression vectors described herein.

The activated phagocytes herein described can be administered in dosages and routes and at times to be determined in appropriate pre-clinical and clinical experimentation and trials. Activated phagocytes compositions can be administered multiple times at dosages within these ranges. In some embodiments, administration of the activated phagocytes can be combined with other methods useful to treat the desired disease or condition as determined by those of skill in the art.

The phagocyte to be administered can be autologous, allogeneic, or xenogeneic with respect to the subject undergoing therapy.

The administration of the cells can be carried out in any suitable manner known to those of skill in the art. For example, the cells can be administered to a subject by aerosol inhalation, injection, ingestion, transfusion, implantation or transplantation. The compositions described herein can be administered to a patient transarterially, subcutaneously, intradermally, intratumorally, intranodally, intramedullary, intramuscularly, by intravenous injection, or intraperitoneally. In other implementations, the cells can be injected directly into a target region in the subject, a local disease site in the subject, a lymph node, an organ, a tumor, and the like. The expression vector can be administered to the target region by routes of administration allowing the vector to be provided in blood of the individual, typically by intravenous injections. In principle, there are no specific limitations with respect to the procedures and techniques that are expected to be suitably employed for delivery of the vectors as described herein into the target cell. Non-limiting delivery procedures suitable for the methods disclosed herein include stable or transient transfection, lipofection, electroporation, microinjection, liposomes, iontophoresis, and infection with recombinant viral vectors. In some embodiments, the administration includes a viral-, particle-, liposome-, or exosome-based delivery procedure. (source US2020/0239592).

In some embodiments, the tumor to be treated is a solid tumor or a hematologic malignancy. Examples of hematologic malignancies include acute myeloid leukemia, chronic myelogenous leukemia, myelodysplasia, acute lymphoblastic leukemia, chronic lymphocytic leukemia, multiple myeloma, Hodgkin and non-Hodgkin lymphoma. Examples of solid tumors include lung cancer, melanoma, breast cancer, prostate cancer, colon cancer, renal cell carcinoma, ovarian cancer, pancreatic cancer, hepatocellular carcinoma, neuroblastoma, rhabdomyosarcoma, and brain tumor. Other disease conditions applicable to the methods disclosed herein include bacterial infection, virus-infected cells, virions, defective neurons, or senescent cells.

In some embodiments, the administration includes delivering into endogenous cells ex vivo one or more gene and/or regulatory regions to enhance Rac properties of one or more Rac protein expressed in the phagocyte. In some embodiments, the administration includes delivering into cells in vivo one or more vector herein described. In some embodiments, the administration of the activated phagocytes, vector and/or compositions herein described is expected to activate trogocytosis and/or phagocytosis of the cancer cell.

In some embodiments, a genetically engineered phagocytic cell herein described comprise a heterologous polynucleotide encoding a Rac protein or portion thereof (e.g., a Rae gene), wherein the genetically engineered phagocytic cell exhibits an increased amount of phagocytosis and/or trogocytosis compared to an amount of phagocytosis and/or trogocytosis for a phagocyte devoid of the heterologous polynucleotide.

In some embodiments, a genetically engineered phagocytic cell herein described exhibits an increased amount of phagocytosis and/or trogocytosis of live cells compared to an amount of phagocytosis and/or trogocytosis of the live cells for the phagocyte devoid of the heterologous polynucleotide, optionally wherein the live cells are diseased live cells (e.g., live cancer cells and/or live virally infected cells).

In some embodiments, a genetically engineered phagocytic cell herein described has a modified cellular function compared to a cellular function of the phagocyte devoid of the heterologous polynucleotide, optionally wherein expression of the heterologous polynucleotide provides the modified cellular function. In some of these embodiments, a genetically engineered phagocytic cell herein described the modified cellular function is one or more of increased binding to GTP by the Rac protein or portion thereof, increased binding rate for GTP and the Rac protein or portion thereof, reduced hydrolysis rate for GTP and the Rac protein or portion thereof, and/or modified (e.g., increased or decreased) downstream product level (e.g., increased pAKT concentration, increased F-actin content, and/or increased reactive oxygen species (ROS) concentration).

As used herein, the terms "decrease" "reduce," "reduced," "reducing," "reduction," "diminish," and (and grammatical variations thereof), a detectable decrease of a reference value unless the context indicates otherwise. According a decrease can comprise a decreased at least about 5%, 10%, 15%, 20%, 25%, 30%, 35%, 40%, 45%, 50%, 55%, 60%, 65%, 70%, 75%, 80%, 85%, 90%, 95%, 97%, 98%, 99%, or 100% such as compared to another measurable property or quantity (e.g., a control value). In some embodiments, the reduction can result in no or essentially no (i.e., an insignificant amount, e.g., less than about 10% or even 5%) detectable activity or amount.

In some embodiments, a genetically engineered phagocytic cell herein described comprises a heterologous polynucleotide encoding a Rac protein or portion thereof, wherein the genetically engineered phagocytic cell has a modified cellular function compared to a cellular function of a phagocyte devoid of the heterologous polynucleotide. In some of those embodiments, a genetically engineered phagocytic cell herein described expresses the heterologous polynucleotide, optionally wherein expression of the heterologous polynucleotide provides the modified cellular function. In some of those embodiments, a genetically engineered phagocytic cell herein described the modified cellular function is one or more of increased binding to GTP by the Rac protein or portion thereof, increased binding rate for GTP and the Rac protein or portion thereof, reduced hydrolysis rate for GTP and the Rac protein or portion thereof, and/or modified (e.g., increased or decreased) downstream product level (e.g., increased pAKT concentration, increased F-actin content, and/or increased reactive oxygen species (ROS) concentration).

In some embodiments, a genetically engineered phagocytic cell herein described comprises a heterologous polynucleotide, and the heterologous polynucleotide encodes a mutated Rac protein or portion thereof or a non-mutated Rac protein or portion thereof (e.g., a wild-type Rac protein or portion thereof), optionally wherein the heterologous polynucleotide comprises a nucleic acid sequence encoding an amino acid sequence having at least 70%, 75%, 80%, 85%, or 90% sequence identity to any one of SEQ ID NO: 1.

In some embodiments, a genetically engineered phagocytic cell herein described comprises a heterologous polynucleotide, and the heterologous polynucleotide encodes a Rac1, Rac2, or Rac3 protein or portion thereof.

In some embodiments, a genetically engineered phagocytic cell herein described comprises a heterologous polynucleotide, and the heterologous polynucleotide encodes a mutated Rac protein or portion thereof comprising one or more substituted amino acid residue(s) located at positions 11, 12, 28, 29, 30, 34, 62, 63, 92, and/or 157, with reference to the amino acid sequence and position numbering of SEQ ID NO:1.

In some embodiments, a genetically engineered phagocytic cell herein described comprises a heterologous polynucleotide, and the heterologous polynucleotide encodes a mutated Rac2 protein or portion thereof, optionally wherein the mutated Rac2 protein or portion thereof has a lysine at position 62, a leucine at position 61, a valine at position 63, an arginine at position 12 and/or a valine at position 12 with reference to amino acid position numbering of SEQ ID NO: 1, further optionally wherein the mutated Rac2 protein or portion thereof comprises a E62K, Q61L, D63V, G12R and/or G12V mutation compared to SEQ ID NO:1.

In some embodiments, a genetically engineered phagocytic cell herein described comprises a heterologous polynucleotide, and further comprises a promoter operably linked to the heterologous polynucleotide. In some of those embodiments, a genetically engineered phagocytic cell the promoter can be a constitutive promoter, optionally wherein the constitutive promoter is selected from CMV from human cytomegalovirus, EF1a from human elongation factor 1 alpha, SV40 from the simian vacuolating virus 40, PGK1 from phosphoglycerate kinase gene, Ubc from human ubiquitin C gene, human beta actin, CAAG, and SynI promoters.

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

In some embodiments, where a genetically engineered phagocytic cell herein described comprises a heterologous polynucleotide, and a promoter operably linked to the heterologous polynucleotide, the promoter is a conditional promoter, optionally wherein the conditional promoter is selected from TET (tetracycline-response elements, TET-ON/TET-OFF), Lac, dCas-transactivator, Zinc-finger-TF, TALENs-ZF Gal4-uas, synNotch and inducible promoters based on endogenous signals TNF-alpha, and cFOS promoter.

In some embodiments, where a genetically engineered phagocytic cell herein described comprises a heterologous polynucleotide, and a promoter operably linked to the heterologous polynucleotide, the cell further comprises one or more regulatory region(s) operably linked to the heterologous polynucleotide.

In some embodiments, where a genetically engineered phagocytic cell herein described comprises a heterologous polynucleotide, and a promoter operably linked to the heterologous polynucleotide, the heterologous polynucleotide and the promoter are comprised within a gene expression cassette.

In some embodiments, a genetically engineered phagocytic cell herein described comprises a heterologous Rac protein or portion thereof, wherein the genetically engineered phagocyte exhibits an increased amount of phagocytosis and/or trogocytosis compared to an amount of phagocytosis and/or trogocytosis for a phagocyte devoid of the heterologous Rac protein or portion thereof.

In some embodiments, where a genetically engineered phagocytic cell herein described comprises a heterologous polynucleotide, the genetically engineered phagocytic cell exhibits an increased amount of phagocytosis and/or trogocytosis of live cells compared to an amount of phagocytosis and/or trogocytosis of the live cells for the phagocyte devoid of the heterologous polynucleotide, optionally wherein the live cells are diseased live cells (e.g., live cancer cells and/or live virally infected cells).

In some embodiments, where a genetically engineered phagocytic cell herein described comprises a heterologous polynucleotide, the genetically engineered phagocytic cell has a modified cellular function compared to a cellular function of the phagocyte devoid of the heterologous Rac protein or portion thereof, optionally wherein production of the heterologous Rac protein or portion thereof provides the modified cellular function.

In some of those embodiments, where a genetically engineered phagocytic cell herein described comprises a heterologous polynucleotide, the modified cellular function is one or more of increased binding to GTP by the Rac protein or portion thereof, increased binding rate for GTP and the Rac protein or portion thereof, reduced hydrolysis rate for GTP and the Rae protein or portion thereof, and/or modified (e.g., increased or decreased) downstream product level (e.g., increased pAKT concentration, increased F-actin content, and/or increased reactive oxygen species (ROS) concentration).

In some embodiments, where a genetically engineered phagocytic cell herein described comprises a heterologous Rac protein or portion thereof, wherein the genetically engineered phagocytic cell has a modified cellular function compared to a cellular function of a phagocyte devoid of the heterologous polynucleotide.

In some embodiments, where a genetically engineered phagocytic cell herein described comprises a heterologous Rac protein or portion thereof, the genetically engineered phagocytic cell produces the heterologous Rac protein or portion thereof, optionally wherein expression of the heterologous protein or portion thereof provides the modified cellular function. In some of those embodiments the modified cellular function is one or more of increased binding to GTP by the Rac protein or portion thereof, increased binding rate for GTP and the Rac protein or portion thereof, reduced hydrolysis rate for GTP and the Rac protein or portion thereof, and/or modified (e.g., increased or decreased) downstream product level (e.g., increased pAKT concentration, increased F-actin content, and/or increased reactive oxygen species (ROS) concentration).

In some embodiments, where a genetically engineered phagocytic cell herein described comprises a heterologous Rac protein or portion thereof, the heterologous Rae protein or portion thereof is a mutated or non-mutated Rac protein or portion thereof, optionally wherein the heterologous Rac protein or portion thereof has an amino acid sequence having at least 70%, 75%, 80%, 85%, or 90% sequence identity to any one of SEQ ID NO:1.

In some embodiments, where a genetically engineered phagocytic cell herein described comprises a heterologous Rac protein or portion thereof, the heterologous Rae protein or portion thereof is a Rac1, Rac2, or Rac3 protein or portion thereof.

In some embodiments, where a genetically engineered phagocytic cell herein described comprises a heterologous Rac protein or portion thereof, the heterologous Rac protein or portion thereof is a mutated Rac protein or portion thereof comprising one or more substituted amino acid residue(s) located at positions 11, 12, 28, 29, 30, 34, 62, 63, 92, and/or 157, with reference to the amino acid sequence and position numbering of SEQ ID NO:1.

In some embodiments, where a genetically engineered phagocytic cell herein described comprises a heterologous Rac protein or portion thereof, the heterologous Rae protein or portion thereof is a mutated Rac2 protein or portion thereof, optionally wherein the mutated Rac2 protein or portion thereof has a lysine at position 62, a leucine at position 61, a valine at position 63, an arginine at position 12 and/or a valine at position 12 with reference to amino acid position numbering of SEQ ID NO: 1, further optionally wherein the mutated Rac2 protein or portion thereof comprises a E62K, Q61L, D63V, G12R and/or G12V mutation compared to SEQ ID NO:1.

In some embodiments, where a genetically engineered phagocytic cell herein described comprises a heterologous Rac protein or portion thereof, the cell further comprises a heterologous polynucleotide that encodes the heterologous Rac protein or portion thereof (e.g., a Rac gene), optionally wherein the genetically engineered phagocytic cell expresses the heterologous polynucleotide, further optionally wherein the heterologous polynucleotide comprises a nucleic acid sequence having at least 70%, 75%, 80%, 85%, or 90% sequence identity to any one of SEQ ID NO:1.

In some embodiments, where a genetically engineered phagocytic cell herein described comprises a heterologous Rac protein or portion thereof, the cell further comprises a heterologous polynucleotide that encodes the heterologous Rac protein or portion thereof, the cell further comprises a promoter operably linked to the heterologous polynucleotide.

In some embodiments, where a genetically engineered phagocytic cell herein described comprises a heterologous Rac protein or portion thereof, a heterologous polynucleotide that encodes the heterologous Rac protein or portion thereof and a promoter, the promoter can be a constitutive promoter, optionally wherein the constitutive promoter is selected from CMV from human cytomegalovirus, EF1a from human elongation factor 1 alpha, SV40 from the simian vacuolating virus 40, PGK1 from phosphoglycerate kinase gene, Ubc from human ubiquitin C gene, human beta actin, CAAG, and SynI promoters.

In some embodiments, where a genetically engineered phagocytic cell herein described comprises a heterologous Rac protein or portion thereof, a heterologous polynucleotide that encodes the heterologous Rac protein or portion thereof and a promoter, the promoter is a conditional promoter, optionally wherein the conditional promoter is selected from TET (tetracycline-response elements, TET-ON/TET-OFF), Lac, dCas-transactivator, Zinc-finger-TF, TALENs-ZF Gal4-uas, synNotch and inducible promoters based on endogenous signals TNF-alpha, and cFOS promoter.

In some embodiments, where a genetically engineered phagocytic cell herein described comprises a heterologous Rac protein or portion thereof, a heterologous polynucleotide that encodes the heterologous Rac protein or portion thereof and a promoter, the cell can further comprise one or more regulatory region(s) operably linked to the heterologous polynucleotide.

In some embodiments, where a genetically engineered phagocytic cell herein described comprises a heterologous Rac protein or portion thereof, a heterologous polynucleotide that encodes the heterologous Rac protein or portion thereof and a promoter, the heterologous polynucleotide and the promoters are comprised within a gene expression cassette.

In some embodiments, a genetically engineered phagocytic cell herein described comprises a polynucleotide encoding a Rac protein or portion thereof, the genetically engineered phagocytic cell produces the Rac protein or portion thereof in an increased amount compared to a non-genetically engineered phagocyte (e.g., a native or wild-type phagocyte, optionally a non-genetically engineered phagocyte that produces the Rac protein or portion), and the genetically engineered phagocytic cell exhibits an increased amount of phagocytosis and/or trogocytosis compared to an amount of phagocytosis and/or trogocytosis for the non-genetically engineered phagocyte.

In some of embodiments, where a genetically engineered phagocytic cell herein described comprises a polynucleotide encoding a Rac protein or portion thereof, the genetically engineered phagocytic cell exhibits an increased amount of phagocytosis and/or trogocytosis of live cells compared to an amount of phagocytosis and/or trogocytosis of the live cells for the non-genetically engineered phagocyte, optionally wherein the live cells are diseased live cells (e.g., live cancer cells and/or live virally infected cells).

In some of those embodiments, where a genetically engineered phagocytic cell herein described comprises a polynucleotide encoding a Rac protein or portion thereof, the genetically engineered phagocytic cell has a modified cellular function compared to a cellular function of the non-genetically engineered phagocyte, optionally wherein expression of the polynucleotide encoding the Rac protein or portion thereof provides the modified cellular function.

In some of those embodiments, where a genetically engineered phagocytic cell herein described comprises a polynucleotide encoding a Rac protein or portion thereof, and the genetically engineered phagocytic cell has a modified cellular function, the modified cellular function is one or more of increased binding to GTP by the Rac protein or portion thereof, increased binding rate for GTP and the Rac protein or portion thereof, reduced hydrolysis rate for GTP and the Rac protein or portion thereof, and/or modified (e.g., increased or decreased) downstream product level (e.g., increased pAKT concentration, increased F-actin content, and/or increased reactive oxygen species (ROS) concentration).

In some embodiments, a genetically engineered phagocytic cell herein described comprises a polynucleotide encoding a Rac protein or portion thereof, the genetically engineered phagocytic cell produces the Rac protein or portion thereof in an increased amount compared to a non-genetically engineered phagocyte (e.g., a non-genetically engineered phagocyte that produces the Rac protein or portion), and the genetically engineered phagocytic cell has a modified cellular function compared to a cellular function of the non-genetically engineered phagocyte.

In some embodiments, where a genetically engineered phagocytic cell herein described comprises a polynucleotide encoding a Rac protein or portion thereof, the genetically engineered phagocytic cell expresses the polynucleotide encoding the Rac protein or portion thereof, optionally wherein expression of the polynucleotide encoding the Rac protein or portion thereof and/or production of the Rae, protein or portion thereof provides the modified cellular function.

In some embodiments, where a genetically engineered phagocytic cell herein described comprises a polynucleotide encoding a Rac protein or portion thereof, and expression of the polynucleotide encoding the Rac protein or portion thereof and/or production of the Rac protein or portion thereof provides the modified cellular function, the modified cellular function is one or more of increased binding to GTP by the Rac protein or portion thereof, increased binding rate for GTP and the Rac protein or portion thereof, reduced hydrolysis rate for GTP and the Rac protein or portion thereof, and/or modified (e.g., increased or decreased) downstream product level (e.g., increased pAKT concentration, increased F-actin content, and/or increased reactive oxygen species (ROS) concentration).

In some embodiments, where a genetically engineered phagocytic cell herein described comprises a polynucleotide encoding a Rac protein or portion thereof, and expression of the polynucleotide encoding the Rac protein or portion thereof and/or production of the Rac protein or portion thereof provides the modified cellular function, the polynucleotide encoding the Rac protein or portion thereof encodes a mutated or non-mutated Rac protein or portion thereof, optionally wherein the polynucleotide encoding the Rac protein or portion thereof encodes an amino acid sequence having at least 70%, 75%, 80%, 85%, or 90% sequence identity to SEQ ID NO: 1.

In some embodiments, where a genetically engineered phagocytic cell herein described comprises a polynucleotide encoding a Rac protein or portion thereof, and expression of the polynucleotide encoding the Rac protein or portion thereof and/or production of the Rac protein or portion thereof provides the modified cellular function, the polynucleotide encoding the Rac protein or portion thereof encodes a Rac1, Rac2, or Rac3 protein or portion thereof.

In some embodiments, where a genetically engineered phagocytic cell herein described comprises a polynucleotide encoding a Rac protein or portion thereof, and expression of the polynucleotide encoding the Rac protein or portion thereof and/or production of the Rac protein or portion thereof provides the modified cellular function, the polynucleotide encoding the Rac protein or portion thereof encodes a mutated Rac protein or portion thereof comprising one or more substituted amino acid residue(s) located at positions 11, 12, 28, 29, 30, 34, 62, 63, 92, and/or 157, with reference to the amino acid sequence and position numbering of SEQ ID NO:1.

In some embodiments, where a genetically engineered phagocytic cell herein described comprises a polynucleotide encoding a Rac protein or portion thereof, and expression of the polynucleotide encoding the Rac protein or portion thereof and/or production of the Rac protein or portion thereof provides the modified cellular function, the polynucleotide encoding the Rac protein or portion thereof encodes a mutated Rac2 protein or portion thereof, optionally wherein the mutated Rac2 protein or portion thereof has a lysine at position 62, a leucine at position 61, a valine at position 63, an arginine at position 12 and/or a valine at position 12 with reference to amino acid position numbering of SEQ ID NO: 1, further optionally wherein the mutated Rac2 protein or portion thereof comprises a E62K, Q61L, D63V, G12R and/or C12V mutation compared to SEQ ID NO:1.

In some embodiments, where a genetically engineered phagocytic cell herein described comprises a polynucleotide encoding a Rac protein or portion thereof, and expression of the polynucleotide encoding the Rac protein or portion thereof and/or production of the Rac protein or portion thereof provides the modified cellular function, the cell further comprises a promoter operably linked to the polynucleotide encoding the Rac protein or portion thereof, optionally wherein the protomer is a heterologous promoter.

In some embodiments, where a genetically engineered phagocytic cell herein described comprises a polynucleotide encoding a Rac protein or portion thereof, where expression of the polynucleotide encoding the Rac protein or portion thereof and/or production of the Rac protein or portion thereof provides the modified cellular function and a promoter, the promoter is a constitutive promoter, optionally wherein the constitutive promoter is selected from CMV from human cytomegalovirus, EF1a from human elongation factor 1 alpha, SV40 from the simian vacuolating virus 40, PGK1 from phosphoglycerate kinase gene, Ube from human ubiquitin C gene, human beta actin. CAAG, and SynI promoters.

In some embodiments, where a genetically engineered phagocytic cell herein described comprises a polynucleotide encoding a Rac protein or portion thereof, where expression of the polynucleotide encoding the Rac protein or portion thereof and/or production of the Rac protein or portion thereof provides the modified cellular function and a promoter, the promoter is a conditional promoter, optionally wherein the conditional promoter is selected from TET (tetracycline-response elements, TET-ON/TET-OFF), Lac, dCas-transactivator, Zinc-finger-TF, TALENs-ZF Gal4-uas, synNotch and inducible promoters based on endogenous signals TNF-alpha, and cFOS promoter.

In some embodiments, where a genetically engineered phagocytic cell herein described comprises a polynucleotide encoding a Rac protein or portion thereof, where expression of the polynucleotide encoding the Rac protein or portion thereof and/or production of the Rac protein or portion thereof provides the modified cellular function and a promoter, the cell further comprises one or more regulatory region(s) operably linked to the polynucleotide encoding the Rac protein or portion thereof, optionally wherein at least one of the one or more regulatory region(s) is a heterologous regulatory region.

In some embodiments, where a genetically engineered phagocytic cell herein described comprises a polynucleotide encoding a Rac protein or portion thereof, where expression of the polynucleotide encoding the Rac protein or portion thereof and/or production of the Rac protein or portion thereof provides the modified cellular function and a promoter, the genetically engineered phagocytic cell overexpresses or inhibits expression of an upstream regulator, optionally wherein the upstream regulator is a guanine nucleotide exchange factor (e.g., TIAM1 and/or Vav) and/or a guanine nucleotide triphosphatase activating protein.

In some embodiments, where a genetically engineered phagocytic cell herein described comprises a polynucleotide encoding a Rac protein or portion thereof, where expression of the polynucleotide encoding the Rac protein or portion thereof and/or production of the Rac protein or portion thereof provides the modified cellular function and a promoter the polynucleotide encoding the Rac protein or portion thereof and the promoter are comprised within a gene expression cassette.

In some embodiments, a genetically engineered phagocytic cell herein described is a genetically engineered monocyte (e.g., a genetically engineered microglial cell), macrophage, dendritic cell, neutrophil, or precursor thereof.

In some embodiments, a genetically engineered phagocytic cell herein described, the cell further comprising a chimeric antigen receptor (CAR) gene (e.g., a polynucleotide encoding a CAR), optionally wherein the genetically engineered phagocytic cell expresses the CAR gene.

In some embodiments, a genetically engineered phagocytic cell herein described, the CAR gene is operably linked to the same promoter as the heterologous polynucleotide encoding the Rac protein or portion or polynucleotide encoding the Rac protein or portion.

In some embodiments, a genetically engineered phagocytic cell herein described, the CAR gene is operably linked to a second promoter and the second promoter is different than the promoter operably linked to the heterologous polynucleotide encoding the Rac protein or portion or polynucleotide encoding the Rac protein or portion, optionally wherein the second promoter is a heterologous promoter.

In some embodiments, a genetically engineered phagocytic cell herein described the second promoter is a constitutive promoter, optionally wherein the constitutive promoter is selected from CMV from human cytomegalovirus, EF1a from human elongation factor 1 alpha, SV40 from the simian vacuolating virus 40, PGK1 from phosphoglycerate kinase gene, Ubc from human ubiquitin C gene, human beta actin, CAAG, and SynI promoters.

In some embodiments, a genetically engineered phagocytic cell herein described, the second promoter is a conditional promoter, optionally wherein the conditional promoter is selected from TET (tetracycline-response elements, TET-ON/TET-OFF), Lac, dCas-transactivator, Zinc-finger-TF, TALENs-ZF Gal4-uas, synNotch and inducible promoters based on endogenous signals TNF-alpha, and cFOS promoter.

In some embodiments, a genetically engineered phagocytic cell herein described, the CAR gene is comprised within a gene expression cassette, optionally the same or a different gene expression cassette than the heterologous polynucleotide encoding the Rac protein or portion or polynucleotide encoding the Rac protein or portion.

In some embodiments, a method of producing a genetically engineered phagocytic cell is described, the method comprising: introducing a heterologous polynucleotide encoding a Rac protein or portion thereof into a phagocytic cell, thereby producing the genetically engineered phagocytic cell, optionally wherein the genetically engineered phagocytic cell is the genetically engineered phagocytic cell according to any one of the embodiments herein described.

In some embodiments of the method of producing a genetically engineered phagocytic cell, the introducing comprises stably introducing the heterologous polynucleotide encoding the Rac protein or portion thereof.

In some embodiments of the method of producing a genetically engineered phagocytic cell, the introducing comprises transiently introducing the heterologous polynucleotide encoding the Rac protein or portion thereof.

In some embodiments, a method of producing a genetically engineered phagocytic cell is described, the method comprises: introducing a heterologous Rac protein or portion thereof into a phagocytic cell, thereby producing the genetically engineered phagocytic cell, optionally wherein the genetically engineered phagocytic cell is the genetically engineered phagocytic cell of any one of the embodiments herein described In some embodiments, of the method of producing a genetically engineered phagocytic cell, the introducing comprises introducing a heterologous polynucleotide encoding the heterologous Rac protein or portion thereof into the phagocytic cell.

In some embodiments, of the method of producing a genetically engineered phagocytic cell, the introducing comprises stably introducing the heterologous polynucleotide encoding the heterologous Rac protein or portion thereof.

In some embodiments, of the method of producing a genetically engineered phagocytic cell, the introducing comprises transiently introducing the heterologous polynucleotide encoding the heterologous Rac protein or portion thereof.

In some embodiments, a method is described of producing the genetically engineered phagocytic cell according to any one of the embodiments herein described. The method comprises: introducing the polynucleotide encoding the Rac protein or portion thereof into a phagocytic cell, thereby producing the genetically engineered phagocytic cell.

In some embodiments, of the method of producing the genetically engineered phagocytic cell, the introducing comprises stably introducing the polynucleotide encoding the Rac protein or portion thereof.

In some embodiments, of the method of producing the genetically engineered phagocytic cell, the introducing comprises transiently introducing the polynucleotide encoding the Rac protein or portion thereof.

In some embodiments, of the method of producing the genetically engineered phagocytic cell, the introducing is performed in vivo or ex vivo.

In some embodiments, of the method of producing the genetically engineered phagocytic cell, the method further comprises obtaining the phagocytic cell.

In some embodiments, of the method of producing the genetically engineered phagocytic cell, the phagocytic cell is obtained from an individual to be administered the genetically engineered phagocytic cell.

In some embodiments, of the method of producing the genetically engineered phagocytic cell, the phagocytic cell is obtained from a source compatible with an individual to be administered the genetically engineered phagocytic cell.

In some embodiments, a method of treating a subject, is described the method comprises: administering the genetically engineered phagocytic cell herein described or the genetically engineered phagocytic cell produced in accordance with any one of the methods herein described to the subject, thereby treating the subject.

In some embodiments, a method of treating a subject, is described the method comprises: administering the genetically engineered phagocytic cell herein described the subject, wherein the genetically engineered phagocytic cell is produced from a phagocytic cell obtained from the subject, thereby treating the subject.

In some embodiments of the method of treating a subject, wherein the genetically engineered phagocytic cell is produced from a phagocytic cell obtained from the subject, thereby treating the subject, the method comprises treating a cancer (e.g., lung cancer, melanoma, breast cancer, prostate cancer, colon cancer, renal cell carcinoma, ovarian cancer, pancreatic cancer, hepatocellular carcinoma, neuroblastoma, rhabdomyosarcoma, and/or brain cancer), a hematologic malignancy (e.g., acute myeloid leukemia, chronic myelogenous leukemia, myelodysplasia, acute lymphoblastic leukemia, chronic lymphocytic leukemia, multiple myeloma, Hodgkin lymphoma, and/or non-Hodgkin lymphoma), an infection (e.g., a viral infection) and/or Alzheimer's disease.

In some embodiments of the method of treating a subject, wherein the genetically engineered phagocytic cell is produced from a phagocytic cell obtained from the subject, thereby treating the subject, the subject has or is believed to have cancer, a hematologic malignancy, an infection, and/or Alzheimer's disease.

In some embodiments of the method of treating a subject, wherein the genetically engineered phagocytic cell is produced from a phagocytic cell obtained from the subject, thereby treating the subject, the administering comprises administering the genetically engineered phagocytic cell to the subject via inhalation (e.g., aerosol inhalation), injection (e.g., intravenous injection), ingestion, transfusion, implantation, and/or transplantation, optionally wherein the genetically engineered phagocytic cell is intravenously injected into the subject.

In some embodiments of the method of treating a subject, wherein the genetically engineered phagocytic cell is produced from a phagocytic cell obtained from the subject, thereby treating the subject, the administering comprises injecting the genetically engineered phagocytic cell into the subject, optionally wherein the genetically engineered phagocytic cell is injected into a lymph node, organ and/or diseased site (e.g., a tumor and/or infected site) of the subject.

In some embodiments herein described, the expression vectors, activated and in particular mutated genes, genetically engineered cells can be provided as part of a system to treat cancer. The system can comprise any combination of genes, expression vectors, genetically engineered cells selected in view of the target disease condition in effective amounts depending on the experimental design.

The systems herein described can be provided in the form of kits of parts. In kit of parts for performing any one of the methods herein described, the expression vectors, Rac genes, genetically engineered cells, and pharmaceutical compositions can be included in the kit alone in the presence of additional labels for the related detection as well as additional components identifiable by a skilled person.

In a kit of parts, the expression vectors, Rac genes genetically engineered cells, pharmaceutical compositions and additional reagents identifiable by a skilled person are comprised in the kit independently possibly included in a composition together with suitable vehicle carrier or auxiliary agents.

Additional components can include labels, reference standards, and additional components identifiable by a skilled person upon reading of the present disclosure.

The terms "label" and "labeled molecule" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemoluminescence, production of a compound in outcome of an enzymatic reaction and the like.

In embodiments herein described, the components of the kit can be provided, with suitable instructions and other necessary reagents, in order to perform the methods here disclosed. The kit will normally contain the compositions in separate containers. Instructions, for example written or audio instructions, on paper or electronic support such as tapes, CD-ROMs, flash drives, or by indication of a Uniform Resource Locator (URL), which contains a pdf copy of the instructions for carrying out the assay, will usually be included in the kit. The kit can also contain, depending on the particular method used, other packaged reagents and materials (i.e. wash buffers and the like).

Activated phagocytes, vectors, compositions and related methods and systems herein described can be used in various applications alone and/or in combination with additional agents in as will be understood by a skilled person in medical and/or research including basic biology research. In some em to provide mechanistic insights into developmental programmed cell death in *Drosophila* ovaries during starvation induced checkpoints at mid-oogenesis and follicle cell mediated engulfment of nurse cells during late stages of oogenesis((Serizier and McCall 2017); (Meehan, Kleinsorge et al. 2015).

Further details concerning the identification of the suitable carrier agent or auxiliary agent of the compositions, and generally manufacturing and packaging of the kit, can be identified by the person skilled in the art upon reading of the present disclosure.

EXAMPLES

The activated phagocyte of the disclosure and related vectors, compositions, methods and systems herein described are further illustrated in the following examples, which are provided by way of illustration and are not intended to be limiting.

In particular, the following examples illustrate exemplary methods and protocols for providing and using activated phagocyte of the disclosure and related vectors, compositions, methods and systems herein described. A person skilled in the art will appreciate the applicability and the necessary modifications to adapt the features described in detail in the present section, to additional activated phagocyte of the disclosure and related vectors, compositions, methods and systems herein described according to embodiments of the present disclosure.

The following Materials and Methods were used unless otherwise indicated.

*Drosophila* strains and genetics_The fly strains used in the study were slbo-4XPHEGFP (III), UMAT-Lyn-tdTomato (III), ubi-HisRFP (obtained from Weimiao Yu, (Cliffe, Doupé et al. 2017)), slbo-Gal4 (Rorth, Szabo et al. 1998), hsFlp; Ay-Gal4, UAS-GFP (Mishra, Mondo et al. 2019), UAS-Lifeact-GFP (Cai, Chen et al. 2014) and PG150-Gal4; UAS-GFP,Gal80$^{ts}$ (Celeste Berg). Following stocks were obtained from Bloomington *Drosophila* Stock Center (BDSC) Bloomington, IN UAS-PLCd1-PH-GFP (39693), UAS-Rac1V12 (6291), UAS-Rac1N17 (6292), UAS-Rho1V14 (7330, 8144), draper (67033). UAS-lacZ was used as inert control. All the experimental crosses were carried out at 25° C. and 1-day old progeny was fed on dry/wet yeast at 25° C. for 16-20 hours prior to dissection for fixed and live imaging. For generating Rac1V12 clones, flies were heat shocked twice a day for 1 h, about 4 h apart, in a 37° C. water bath. Flies were then kept at 25° C. overnight (on dry/wet yeast) prior to dissection.

Immunostaining: Immunostaining was performed as described in Mishra et al., 2019. The antibodies used in the study were Rabbit anti-GFP (G10362, Thermo Fisher, 1:1000), E-cad (DCAD2, Developmental Studies Hybridoma Bank, 1:5), Fas3 (7G10, Developmental Studies Hybridoma Bank, 1:10), Dcp-1 (9578S, Cell Signalling, 1:50) and active Caspase3 (Promega, 1:200). Alexa Fluor 488 and 568 conjugated secondary antibodies (Thermo Fisher) were used at 1:400 dilution and F-actin was labelled using Phalloidin-Atto 647N (Sigma Aldrich). Lysotracker staining of egg chambers were performed as described in Timmons et al., 2016.

Live Imaging of cultured egg chambers Dissection and mounting of live egg chambers were performed as described previously (Prasad and Montell 2007). Time-lapse imaging was performed using a 40×/1.1 numerical aperture (NA) water immersion objective lens on a Zeiss 780 Laser scanning confocal microscope. 1 μm thick z-sections ranging the entire egg chamber were collected at 5 min interval in lambda mode. GFP, tdTomato and RFP signals were unmixed using a linear unmixing approach in the Zeiss Zen software. Animal cell culture RAC2(RAC2) (NM_-002872) Human Untagged Clone (ORIGENE) and Rac2 [E62K](Hsu et al., 2019) were cloned in pCW57 vector using Nhe and Age sites. Lentiviral transfection of these constructs was carried out in HL60 cells. For macrophage differentiation, HL60 cells were seeded at a density of $5\times10^5$ cells/ml in RPMI 1640 plus L-glutamine and 10% heat-inactivated fetal bovine serum (FBS) media in a coverslip coated 6-well plate and treated with 32 nM 12-O-tetradecanoylphorbol-13-acetate (TPA) for 48 h. Equal density of Jurkat T cells were labeled with Cell Tracker Red (Invitrogen) and co-cultured with differentiated macrophages for 24 h for phagocytosis assay.

Statistical analysis and Figure preparation All statistical analyses (unpaired t-test and one-way analysis of variance [ANOVA]) and graph preparation were performed in GraphPad Prism software. Figures and illustrations were created in Adobe Photoshop.

Example 1: Rho Family GTPases: Regulators of Actin Cytoskeleton Network

Rac is a Rho-family GTPase best known for its role in stimulating actin polymerization and protrusion at the leading edges of migrating cells (Ridley, Paterson et al. 1992); (Murphy and Montell 1996): (Ridley 2015)). Rac also stimulates macropinocytosis (Ridley, Paterson et al. 1992)) and phagocytosis (Massol, Montcourrier et al. 1998)). Of the three highly related Rac genes in humans, Rac1 is relatively ubiquitously expressed while Rac2 expression is predominantly expressed in cells of hematopoietic origin. Infants with the dominant negative D57N mutation in Rac2 exhibit severe phagocyte defects that include defective production of superoxide. Patients homozygous for a null allele exhibit lymphopenia and variable immunodeficiency. Neutrophils from Rac2+/− or Rac2−/− mice exhibit impairment in chemotaxis and NADPH oxidase activity. These findings indicate that Rac2 is required for phagocyte chemotaxis and superoxide production as well as for lymphocyte development and/or survival.

A schematic illustration of how Rho family GTPases act as a regulators of Actin cytoskeleton network is depicted in FIG. 1A and images of morphology after abnormal GTPase over-activation are shown in FIGS. 1B to 1D, wherein FIG. 1B shows unstimulated 3T3 fibroblast cell, FIG. 1C shows Actin ruffles observed upon Rac activation, FIG. 1D showing Filopodia observed after Cdc42 activation, FIG. 1E showing Actin stress fibers observed after Rho activation.

Example 2: Rac Proteins are Conserved Among Individuals of Various Taxonomic Ranks Rac proteins are highly conserved in sequence and structure in view of the key functions provided in the cell through binding of GTP and downstream effectors.

FIG. 1F. shows 3D structure of the exemplary RAC1(3TH 5) showing residues D57 of Rac1, which in coordination with $Mg^{2+}$, is critical for the activation cycle of Rac1 (Acuner et al. 2021), RacD57N which is known to act as a dominant negative mutation for both Rac1 and Rac2 (Lougaris et al. 2020) and E 62 residues whose replacement with Lysine (K) results in a dominant activating mutation (Hsu et al. 2019).

The 3D structure is highly conserved among Rac1 Rac2 and Rc3 proteins as shown by the exemplary sequence alignment shown in FIG. 1G and FIG. 1H.

In particular FIG. 1G, shows multiple sequence alignment of Human RAC1, 2, 3 protein displaying sequence conservation and different motifs/regions and in particular, the nucleotide binding region, the effector binding region and the lipid binding region which are regions encompassing residues known or expected to result in a Rac protein having enhanced rac properties (see Example 3 and Example 4 below).

FIG. 1H reporting a multiple sequence alignment of Human RAC1, 2, 3 and CDC42 proteins displaying Switch I and Switch II regions.

The sequence and structure of Rac protein are further conserved among different individuals of different taxonomic levels as exemplified by FIG. 1I and FIG. 1J also showing conserved residues of the nucleotide binding region, effector region and lipid binding region.

FIG. 1I and FIG. 1J shows an exemplary sequence alignment between Rac1 proteins (FIG. 1I) and Rac2 proteins (FIG. 1J) of exemplary individuals (drosophila, human, bovine, mouse and *Caenorhabditis elegans*) further showing the nucleotide binding region (black highlight), Effector region (gray highlight) and Lipid binding region (light gray highlight boxed).

Sequences, splice variants, and structures of RAC1, RAC2, and/or RAC3 gene sequences and gene products have been described in the art. See, for example, the Gene Cards.com website available on the World Wide Web at genecards.org/cgi-bin/carddisp. pl?gene=RAC1, genecards.org/cgi-bin/carddisp. pl?gene=RAC2, and genecards.org/cgi-bin/carddisp. pl?gene=RAC3 (from US Patent US2015/0185223A1 incorporated by reference in its entirety) (Mano))

As can be seen from the exemplary illustration of FIG. 1I and FIG. 1J RAC1 and RAC2 is highly conserved across species at residue level and structural domains and so is RAC3 as will be understood by a skilled person Hence the gain-of-function mutants such as mutations at D11, G12, F28, P29, G30, P34, E62, N92, C157 see Example 3 and Example 4 below) are expected to behave in a similar manner.

Such a similarity is exemplified by the schematic illustration of FIG. 1K which shows a schematic representation of Rac2 showing Switch I, Switch II and C terminal regions and location of a P34H replacement (upper panel) and as well as a sequence alignment in various individuals of the Switch I region showing location of the P34H and the resulting conserved sequences.

Example 3: Effects of Rac Gene Mutations in Rac Protein Regions

Rac proteins have a conserved structure and the correlation between the different Rac structural regions and the functionality of the Rac proteins is known.

One of such region is the Switch I region (typically from residue 26 to residue 45 of the Rac sequence): in view of the detected loss in interaction between the guanine ring of nucleotide and amino acid residue, mutations in residues such as F28, P29, G30, P34 can result in an increased GTP association (~1.5 fold or higher) and decreased GTPase activity (50% or less) compared to endogenous RAC (see discussion in Example 4). Multiple mutations in residues in the Switch I region have been identified that allow to decrease GTPase activity too (50% or less) such as double mutants in P29,G30 (see discussion in Example 4).

Similar considerations apply to the Switch II region (typically, from residue 59 to residue 74 of the Rac sequence): in view of the detected increased GTP association (~1.5 fold or higher), and/or decreased GTPase activity (50% or less) compared to endogenous RAC, as well as increased binding to the downstream effector PAK1 and phosphorylation of AKT (~1.5 fold) resulting from mutations of residues therein (see e.g. E62 known to be involved in binding of Rac to GTP).

An additional region encompassing residues whose mutation is known or expected to result in a Rac protein having enhanced rac properties is the PM (Phosphate Magnesium) binding regions. In particular, Rac protein comprise a first PM region (typically from residues 10 to residue 17), a second PM region (typically from residue 29 to residues 35) and a third PM region, (typically from residue 56 to residues 60) Mutations is the PM regions which overlap with the Switch I region, have been identified that results in a decreased GTPase activity (50% or less) compared to endogenous RAC, e.g. D11.

The third PM region is present between residues (aa 56-60) and is identical in Rac1 and H-ras, but some differences are present in the first two PM regions (Menard and Snyderman n.d.).

In view of the data known about Rac structure and mutations resulting in enhanced Rac properties, regions have been identified encompassing residues whose mutation is known or expected to result in Rac activation are the nucleotide binding region, effector region and lipid binding region (see Example 2, FIG. 1G, FIG. 1I, FIG. 1J).

In particular, mutations in the nucleotide binding regions of Rac2 can result in dominant activating phenotypes where RAC2 is locked in an GTP bound active form. For example, a missense mutation RAC2 G12R at the N-terminus GTP binding region disrupts the GTP hydrolysis in a similar manner as RAC2 E62K. Patients with a heterozygous RAC2 G12R mutation also show a similar phenotype such as RAC2 E62K where they lack T and B lymphocytes and circulating monocytes in the blood resulting in a form of severe combined immunodeficiency [4] (Lagresle-Peyrou, Olichon et al. 2021).

Exemplary of mutations of the nucleotide binding regions, resulting in activating Rae proteins comprise replacement of residues resulting in a distance between the residue and targeted moiety after binding of 3.2 Å or less, in particular 2.5 or 2.7 Å such as the distance of the current mutations that strengthen and prolong the binding between Rac and GTP.

Mutations falling in the nucleotide binding region, effector region and lipid binding region comprise D11 (in PM region), G12, F28, P29, G30, P34 (in Switch I region), E62 (in Switch II region), N92, C157 all reported for activating mutations for Rac proteins (see also Example 4 below).

Example 4: Exemplary Activating Rac Mutations

Various exemplary mutations have been identified in nucleotide binding regions, effector regions, and lipid binding region of a Rac proteins.

For example, in RAC1 the mutation P29S in the Switch I region has been shown to result in an increased GDP dissociation, higher affinity for GTP binding, decreased GTPase activity (see (Kawazu et al. 2013) (Kawazu, Ueno et al. 2013) and US Patent US2015/0185223A1 (Mano) incorporated by reference in its entirety).

In particular with respect to the RAC1 mutation P29S, is worth noting that in the RAC1(P29S) crystal structure, there are direct hydrogen bonds between the ribose hydroxyl groups of GMP-PNP (GTP analog) and the backbone carbonyls of both Ser29 and Gly30. This bonding contrasts with the pattern typically observed for Rho family GTPases, where water-mediated hydrogen bonds form between the ribose hydroxyl groups and switch I residues. Instead, the bonding seen in RAC1(P29S) closely aligns to the hydrogen bonding patterns observed in the crystal structure of activated HRAS, where direct interactions of ribose hydroxyl with the backbone are commonly present. The p.Pro29Ser alteration seems to release the conformational restraint inherent in a proline residue at position 29, therefore allowing a RAS-like altered conformation for GTP binding in the switch I loop and increased effector activation. (Krauthammer et al. 2012) (Krauthammer, Kong et al. 2012).

An additional mutation identified to be Rac activating is RAC1 mutation F28L a fast recycling mutation. In particular, the F28L mutation in RAC1 results in loss of interaction between codon 28 and the nucleoside, suggesting that for RAC1(F28L), fast cycling results from reduced affinity for nucleotide. (Kumar, Rajendran et al. 2013).

Although the overall architectures are very similar, the conformation of the Switch I loops of RAC1(P29S) and RAC1(F28L) are divergent from each other, with RAC1 (P29S) showing a Ras-like Switch 1 conformation and RAC1F28L displaying increased flexibility. For RAC1F28L, this is probably due to the loss of the phenylalanine benzyl group and consequent reduced stabilizing interactions with nucleotide. (Kumar, Rajendran et al. 201.3).

In particular, RAC1(F28L) and RAC1(P29S) are self-activated by different mechanisms, with RAC1(F28)L self-activation driven by a loss in interaction between the guanine ring and F28, and RAC1(P29S) is possibly driven by another mechanism, perhaps destabilization of the GDP-loaded inactive state (Kumar, Rajendran et al. 2013).

Additional Rac I mutations can be provided in position C157 a residue adjacent to the guanine ring of bound GTP. In particular, the mutation RAC1(C157Y) results in a Rac1 protein in which both association and dissociation for GTP are accelerated. Accordingly, the transforming potential of C157Y is more contained compared with that of RAC1 (P29S) or RAC1 (N92I) (see (Kawazu et al. 2013) (Kawazu, Ueno et al. 2013) and US Patent US2015/0185223A1 incorporated by reference in its entirety) (Mano).

Additional RA C1 mutations can be provided in position N92 a residue located distant from the binding pocket for GDP/GTP, and renders RAC1 constitutively active (see (Kawazu et al. 2013) (Kawazu. Ueno et al. 2013) and US Patent US2015/0185223A1 (Mano) incorporated by reference in its entirety).

In particular, amino acid substitution (N92I) of RAC1 in a sarcoma cell line, HT1080, renders RAC Constitutively active and highly oncogenic. While HT1080 also carries an NRAS(Q61K) oncoprotein, RAC1(N92I) is the essential growth driver in this cell line, since siRNA-mediated knockdown of RAC1(N92I), but not of NRAS(Q61K), clearly suppressed cell growth. Further screening of RAC1/RAC2/RAC3 mutations among cancer cell lines as well as public databases identified new, transforming mutations for RAC! and RAC2, such as RAC1(N92I) and RAC2(P29Q). (see US Patent US2015/0185223A1 (Mano) incorporated by reference in its entirety) as will be understood by a skilled person).

Additionally, mutations RAC2(P29L), and RAC2(P29Q), in the Switch I region have been also shown to be activating and transforming and to result in a Rac protein with enhanced Rac protein (see (Kawazu et al. 2013) (Kawazu, Ueno et al. 2013) and US Patent US2015/0185223A1 (Mano) incorporated by reference in its entirety).

Reference is also made to the mutations indicated in table S3 of (Kawazu et al. 2013) (Kawazu, Ueno et al. 2013) incorporated by reference in its entirety).

In view of the above, one or more amino acid substitutions of a Rac protein can be selected from N92I, C157Y, P179LI121M, P29Q, P29S, D47Y, P106H based on the enhanced Rac properties detected in RAC1(N92I), RAC1 (P29S), RAC1(C157Y), RAC1(P179L), RAC2(I121M), RAC2(P29Q), RAC2(D47Y), and RAC2(P106H), (see US Patent US2015/0185223A1 (Mano) incorporated by reference in its entirety) as will be understood by a skilled person).

Additional mutations identified to be Rac activating are located in Rac PM regions. Rac1 has three different amino acids from H-ras in each of the first two PM regions, while the third PM region is identical to that of H-bras (PM-Phosphate Magnesium binding region) (see FIG. 1L from (Menard and Snyderman, 1993). Mutation of the amino acids in the first P M region (aa 10-17) to the corresponding amino acids found in H-ras showed that modification of one of them, Aspl 1, resulted in a 50% decrease of the GTPase in rac1, whereas Glyl3 and Sern7 had no effect. In the second PM region (aa 29-35), modification of the Pro29-ly30 pair also reduced GTPase activity by 50% in rac1. rac1 mutated at positions 11 and 29 as well as 30 (P1-P2 mutant) had a 3-4-fold reduced GTPase activity compared to native rac1 (190 vs 552 pmol of GTP hydrolyzed/nmol of GTP7S-binding protein/min at 37° C.), suggesting a cooperative (but nonadditive) interaction between both domains. (Menard and Snyderman, 1993) (Menard and Snyderman n.d.) (Menard and Snyderman 1993). (see FIG. 1M from (Menard and Snyderman, 1993)).

In particular, three mutants were made in the PM1 region (D11 A, T17S, and loop 1) and one in the PM2 region [PG(29,30)VD], as well as a "double" mutant in both regions (i.e., positions 11 and 29-30, P1-P2 mutant). D11A, PG(29,30)VD and P1-P2 mutant had significant reduction in GTPase hydrolysis hence the strongest activating mutations (Menard and Snydernan n.d.) (see FIG. 1M from (Menard and Snyderman, 1993)).

A further Rac mutation shown to be activating is RAC2 P3411 (FIG. 1K): In switch I region, immunodeficiency like RAC2[E62K] ((Lougaris, Chou et al. 2019) (Lougaris et al. 2019) Modeling of RAC2 (P34) suggested a potential interaction between guanosine triphosphate and P341H, which would stabilize the binding of active RAC2 to effector proteins. RAC2P34H had increased binding to the effector protein PAK compared with WT RAC2, which was reversed by loading with endogenous guanosine diphosphate. RAC2$^{P34H}$ therefore has a gain-of-function effect. (Lougaris et al., 2019 (Lougaris, Chou et al 2019).

In some embodiments, activating mutations in RAC2 such as E62K, Q61L, D63V, G12R and G12V can increase the affinity of RAC2 to remain in GTP bound active form and enhance the RAC2 mediated signal transduction. For example, Glutamate 62 (E62) that lies within the Switch II domain of RAC2 is converted to Lysine (K) in RAC2 [E62K] (FIG. 1F, 1G, (Hsu, Donkó et al. 2019). As an additional example, RAC2E62K displays changes in quantifiable parameters such as increased binding to the downstream effector PAK1 and phosphorylation of AKT (~1.5 fold) and maintain high level of F-actin content compared to wild type expression of RAC2 (RAC2 [WT]. The resulting downstream signaling results in increased Reactive oxygen species (ROS) production over time and increased macropinocytosis in patient neutrophils [1] (Hsu, Donkó et al. 2019).

In view of the above exemplary Rac activating mutations in the sense of the disclosure comprise D11A, G12V/R, F28L, P29S, PG(29,30)VD, N92I, C157Y, P29L, P29Q, P341, G12V/R, E62K, N92S, N92T.

In particular in view of the above Rac activating mutations in the sense of the disclosure comprise RAC1 (D11A), RAC1 (G12V/R), RAC1 (F28L), RAG1 (P29S), RAC1 (PG(29,30)VD), RAC1 (N92I), and RAC1 (C157Y), as well as RAC2(P29L), RAC2 (P29Q), RAC2 (P341), RAC2 (G12V/R), RAC2 (E62K), RAC2 (N92S), and RAC2 (N92T).

Example 5: Detection of Enhanced Properties of Activated Rac Proteins by Detection of Rac Increased Binding to GTP The enhanced properties of activated Rac genes can be manifested and quantified in many ways (or a combination of all in some cases).

Previous studies have shown that activating Rac can result in about 1.5-2-fold increase in binding of the GTP.

The quantification of sustained GTP bound active Rac2 can be determined by GDP exchange assays. Compared to the non-activated RAC2, activating Rac2 will result in significant quantifiable GDP dissociation when a GFP is added in the assay and reduced GTP hydrolysis when a GAP is introduced. Previous studies have shown that activating Rac2 can result in ~1.5-2 fold increase in binding of the GTP and phosphorylation of AKT (a downstream effector) with the activated RAC2 [1]. (Hsu, Donkó et al. 2019).

In particular, an exemplary test is provided by the Guanine nucleotide exchange factor (GFP)-mediated guanine nucleotide exchange as determined by GDP exchange assays.

As will be understood by a skilled person GEFs activate GTPases by facilitating their binding to GTP whereas GTPase-activating Proteins (GAPs) hydrolyze GTP and inactivates GTPases. GTPases such as Rac2 have a slow intrinsic rate of nucleotide exchange, which is significantly increased by GFP binding. For example, in the absence of a GFP, both non-activated RAC2 and RAC2[E62K] demonstrated similar intrinsic rates of GDP exchange, however in the presence of a GFP (TIAM1), GDP dissociation rates from non-activated RAC2 were significantly greater than RAC2[E62K]. Further, unlike non-activated RAC2, the addition of a GAP (p50RhoGAP) failed to drive GTP hydrolysis of RAC2[E62K][1]. These data indicate that the RAC2[E62K] remains in the GTP locked active form compared to the non-activated RAC2 and these parameters can be used to test "activated" Rac2 or "activating" mutations in Rac2.

GDP exchange assays can be used to determine the activating expression levels of Rac genes. GEFs activate GTPases by facilitating their binding to GTP whereas GTPase-activating Proteins (GAPs) hydrolyze GTP and inactivates GTPases. GTPases have a slow intrinsic rate of nucleotide exchange, which is significantly increased by GFP binding. For example, generally in the absence of a GFP, both RAC[WT] and activating RAC demonstrate similar intrinsic rates of GDP exchange, however in the presence of a GFP, GDP dissociation rates from RAG[WT] is significantly greater than activating RAC. Further, unlike non-activated RAC, the addition of a GAP fails to drive GTP hydrolysis of activating RAC.

Hence, increased GTP association (~1.5 fold or higher which is tolerated by cells and don't cause toxicity/phenotypic abnormality), decreased GTPase hydrolysis activity (50% or less) compared to endogenous RAC or a combination of both can be used to determine whether the activating level of RAC expression is achieved.

Example 6: Detection of Activating Expression Levels of the Activated Rac Genes: By Detection of Rac Increased Binding to GTP GDP exchange assays can be used to determine the activating expression levels of Rac genes. GEFs activate GTPases by facilitating their binding to GTP whereas GTPase-activating Proteins (GAPs) hydrolyze GTP and inactivates GTPases. GTPases have a slow intrinsic rate of nucleotide exchange, which is significantly increased by GFP binding. For example, generally in the absence of a GFP, both RAC[WT] and activating RAC demonstrate similar intrinsic rates of GDP exchange, however in the presence of a GFP, GDP dissociation rates from RAC[WT] is significantly greater than activating RAC. Further, unlike RAC [WT], the addition of a GAP fails to drive GTP hydrolysis of activating RAC. Hence, increased GTP association (~1.5 fold or higher which is tolerated by cells and don't cause toxicity/phenotypic abnormality), decreased GTPase hydrolysis activity (50% or less) compared to endogenous RAC or a combination of both can be used to determine whether the activating level of RAC expression is achieved.

Example 7: Border Cells are an In Vivo Model for Rac Function

Border cells in the *Drosophila* ovary have long served as an in vivo model for understanding the function of Rac.

A *Drosophila* ovariole containing developing egg chambers is shown (FIG. 2A). A group of six to ten epithelial follicle cells in *Drosophila* ovary called border cells (b), along with a pair of non-motile polar cells (p), migrate collectively through the egg chamber to the anterior border of oocyte (FIGS. 2B, 2C, 2D).

Border cells are a group of 6-10 migratory somatic cells that undertake collective cell migration during stage 9 of oogenesis (FIG. 2A-D). Egg chambers are composed of ~850 somatic follicle cells surrounding a cyst of 15 nurse cells and one oocyte (FIG. 2A-C). Egg chambers grow and develop into a mature egg through 14 stages.

Together border cells (b) and non-motile polar cells (p) they form the micropyle, a structure required for sperm entry. Lack of proper migration causes sterility. High magnification image of a border cells (b) surrounding a pair of non-motile polar cells (p) are shown in FIG. 2D.

The role of Rac in protrusion and cell migration in vivo was first demonstrated in border cells where expression of dominant-negative Rac (Rac1N17) blocks protrusion and chemotaxis (Murphy and Montell 1996) (FIG. 2E, 2F, 2G).

In addition, spatial and temporal regulation of Rac activity is essential. In normal border cells, Rac activity is enhanced in protrusions, and local illumination of a photoactivatable form of Rac is sufficient to steer the migrating cluster Wang, He et al. 2010)). While acute expression of constitutively active Rac into a serum-starved NIH3T3 fibroblasts generates membrane ruffling and macropinocytosis (Ridley, Paterson et al. 1992)), expression of even low levels (at 18° C. as opposed to normal 25° C.) of constitutively active Rac (Rac1V12) in border cells blocks their chemotaxis (Geisbrecht and Montell 2004))(FIG. 2H-J).

Remarkably, expression of high levels of constitutively active Rac (25° C.)) leads to destruction of the entire egg chamber (FIG. 2K, FIG. 2L), even when expression is restricted to the 4-6 outer b or d e r cells (FIG. 2M). The border cell cluster is composed of two cell types: a non-migratory pair of polar cells, which recruit 4-6 migratory cells to surround them (FIG. 2D) and carry them to the oocyte border where both cell types cooperate to form an eggshell structure called the micropyle (Zarani and Margarifs 1991). The micropyle is the site of sperm entry so failure of border cell migration results in complete female sterility (Montell, Rorth et al. 1992).

Border cell migration is complete by stage 10 and during stage 11 of oogenesis, nurse cells transfer the bulk of their cytoplasmic contents into the oocyte. At stage 12, the follicle cells in contact with the nurse cells engulf the nurse cell remains in a process that depends on the engulfment receptor Draper, the adhesion receptor integrin, and Rac ((Timmons et al. 2016 (Timmons, Mondragon et al. 2016); (Meehan, Kleinsorge et al. 2015). Engulfment of the germline by follicle cells can also occur earlier in development, at stage 8, when flies are deprived of protein food, presumably to repurpose nutrients from egg production to survival (Peterson et al. 2003 (Peterson, Barkett et al. 2003).

A possible connection between Rac gene and engulfment and phagocytosis was therefore tested in border cells as reported in Examples 2 to 4 below.

Example 8: Constitutive Rac Activation in Border Cells Promotes Phagocytosis

To determine whether activated Rac was stimulating abnormal or precocious engulfment of the germ line by the border cells, bypassing the normal regulation by developmental signals or nutrient deprivation. Consistent with this interpretation, in egg chambers in which RacCA was expressed only in a subset of follicle cells, nurse cell nuclei appeared small and pyknotic indicative of dying cells compared to the large nuclei of control egg chambers (compare FIGS. 2N and 2O).

At High magnification, the RacCA-expressing follicle cells were detected not only killing germ cells but also engulfing neighboring somatic cells (FIG. 2P, 2Q, 2R)), which is never observed in control slbo-Gal4 expressed in 6-10 anterior follicle cells (FIG. 2P).

In a separate set of experiments RacV12 was expressed using the FLPout technique (Struhl and Basler 1993) in single and pairs of border cells. The related results show that RacV12 expression in these experiments also resulted in engulfment (FIG. 2S, T), thus supporting the conclusion that if even a single cell expressing RacV12 would be rendered phagocytic.

Polar cells (p) are marked with dashed lines and border cells (b) are marked with solid lines. In control (FIG. 2S) polar cell and border cell boundaries are separated whereas in Rac1V12 expression. Polar cells are surrounded and engulfed by the border cells expressing Rac1V12. Clones in border cells and polar cells are marked with GFP.

Together these results demonstrate that local and transient activation of Rac promotes chemotaxis whereas constitutive activation of Rac impairs movement and high levels of constitutive Rac activation is sufficient to promote phagocytosis of neighboring cells, even of living cells. These observations also suggest that, in vivo, active Rac can alter the behavior of RacV12-expressing cells autonomously but can also result in tissue scale phenotypes that are due to aberrant cell-cell interactions.

Example 9: Rac Activated Cells are Capable of Cell Killing and Engulfment

To determine whether cells attacked by RacV12-expressing cells died as a result, egg chambers were tested with clones of follicle cells expressing RacV12 for active executioner caspase (c-Dep1) expression, a marker of apoptotic cell death.

Compared to control egg chambers expressing GFP in clones, in which caspase staining was rare (FIG. 3A), c-Dcp1-positive cells were frequently found next to GFP+ clonal RacV12-expressing cells (GFP+ clonal cells are marked by dashed lines and c-Dcp1 staining is denoted by white arrows) (FIG. 3B-D).

Stage 10 and 11 egg chambers don't show lysotracker staining in border cells or follicle cells marked by GFP (white). Stage 12 nurse cells die by a lysosome-dependent process that is induced by surrounding follicle cell engulfment, and thus lysosomal staining is observed surrounding the nurse cells by lysotracker dye beginning at stage 12 (FIG. 3E-G).

Nurse cells in stage 9 egg chambers expressing slboGal4; UAS-RacV12 also showed intense lysotracker staining (FIG. 3H) suggesting that they were killed precociously.

In order to investigate how few RacV12-expressing cells could kill the entire germ line composed of 15 giant polyploid nurse cells and one oocyte, live-imaging of control (FIGS. 3I-L) and slboGal4; UAS-RacV12 egg chambers (FIG. 3M-P) were carried out.

In the control, the nurse cells nuclei appeared normal, as large and relatively uniformly stained with Hoechst dye throughout the 15-minute imaging period (FIG. 3I-L). While the RacV12-expressing egg chamber looked relatively normal when slboGal4 initiated expression (FIG. 3M), the nurse cells rapidly and synchronously showed signs of cell death including abnormal distribution of DNA (nuclear condensation) and accumulation of cytoplasmic autofluorescence (FIG. 3N-P).

Example 10: Rac Activated Cells are Capable of Performing a Draper-Dependent Phagocytosis The normal death of nurse cells that is induced by follicle cells is called phagoptosis (death by eating). Molecular recognition of stage 12 nurse cells occurs by activation of the engulfment receptor Draper which is expressed by follicle cells. If the tissue destruction caused by RacV12 expression in border cells is also due to a phagoptosis-like mechanism, it might also be Draper-dependent. To test this hypothesis slboGal4 was used to drive UAS-RacV12 in draper homozygous mutants.

Mutation of draper significantly suppressed egg chamber destruction (FIG. 4A-G). While overall egg chamber morphology and nurse cell nuclear morphology were rescued, other defects became apparent. In the drpr−/− mutants, RacV12 expression still caused border cell migration defects (FIG. 4D, E, F). Border cells are labeled by white arrows in FIGS. 4A-E and centripetal cells (another type of follicle cells) showing normal migration in Rac1V12 expressing egg chambers are highlighted by white arrows in FIG. 4F. In addition, although the germ line remained healthy in many egg chambers, the border cells expressing active Rae engulfed polar cells instead of the nurse cells (FIGS. 4I-K), polar cells (p) marked by dashed lines are engulfed by border cells (b) (white arrows).

Expression of RacV12 using a different Gal4 line, one that expresses in small subset of stretch follicle cells early and in nurse cell associated follicle cells at stage 9, similarly cause germ cell death and tissue destruction (FIGS. 4L-N). Thus, active Rac appeared to render follicle cells hyper-phagocytic towards otherwise healthy germline and somatic cells.

Example 11: Effects of Activated Rac Gene in Border Cells

The results reported in Examples 7 to 10 in *Drosophila* did show that expression of a constitutively active form of Rac causes follicle cells in the ovary to prematurely kill and consume neighboring cells.

In particular, the results reported in Examples 7 to 10 in *Drosophila* show that persistent expression of high levels of active Rac in border cells causes destruction of the entire tissue. This destruction is suppressed by nutation of the engulfment receptor Draper, which mediates phagocytosis of germ cell remnants by follicle cells late in normal oogenesis. In draper mutants, border cells expressing active Rac engulf nearby, living follicle cells instead of germ cells. Thus, active Rac is sufficient to cause border cells to engulf living cells.

Example 12: Activated Rac2 Gene (Rac2[E62K]) Results in Phagocyte Activation and Engulfment of Jurkat T Leukemia Cells Since neutrophils and/or macrophages normally engulf B and T cells at the end of their natural lifespan, a set of experiments was carried out to determine whether active Rac might precociously activate this normal program resulting in premature B and T cell death of human B and T cells.

To test this hypothesis, activated form of Rac2 were expressed that was found in human patients in macrophages in cell culture and mixed in fluorescently labeled Jurkat cells, which are T cells derived from a patient with leukemia.

In particular, wild type Rac2, Rac2[E62K], or a vector control were expressed in HL60-derived cells differentiated to a macrophage-like phenotype together with GFP. These cells were mixed with human Jurkat T cell leukemia cells labeled with a red fluorescent dye.

Whereas control macrophage-like cells rarely engulfed Jurkat cells (FIG. 5A), overexpression of wild type Rac increases the frequency of such events by a factor of 2 (FIG. 5B) and expression of Rac2'[E62K] increased the frequency by nearly four-fold (FIGS. 5C and D) (white arrows in FIG. 5A, 5B, 5C). Rac2[E62K] also increased the frequency of contact between macrophages and T cells (FIG. 5E) (gray arrows in FIG. 5A, 5B, 5C). These results offer an explanation for the perplexing lymphopenia and immunodeficiency in Rac2E[62K] patients.

Example 13: Lymphopenia in Human Patients Having Rac2 Mutations is Caused by Phagocyte Hyperactivity or Activation Human patients homozygous for a null allele exhibit lymphopenia and variable immunodeficiency. Neutrophils from Rac2+/− or Rac2−/− mice exhibit impairment in chemotaxis and NADPH oxidase activity. These findings indicate that Rac2 is required for phagocyte chemotaxis and superoxide production as well as for lymphocyte development and/or survival.

Human patients with an activating mutation [E62K] in the hematopoietic-specific Rac2 gene present with symptoms including lymphopenia (suppressed numbers of B and T cells) and immune deficiency, which remains unexplained. In particular while the published report on immune deficiency in human patients shows that the macrophages from the patients are hyperactive according to a number of criteria, the basis for the immune deficiency is unknown.

The data reported in Example 12 showing that expression of an activating mutation in the human Rac2 gene in macrophages is sufficient to activate them to consume and kill cancerous white blood cells. The activating mutations tested in Example 12 were discovered in human patients who suffer from immune deficiency due to loss of B and T cells (lymphocytopenia).

Activating mutations in Rac2 have been reported in human patients. Unsurprisingly, neutrophils from such patients are hyperactive and exhibit aberrant macropinocytotic vesicles and large vacuoles not seen in cells from healthy controls. The Rac2[E62K] mutation impairs both TIAM1-mediated GDP exchange and p50RhoGAP-mediated GTP hydrolysis. The net effect is prolonged Rac2 activation and interaction with effector proteins such as PAK. The clinically most significant defect is immunodeficiency due to reduced numbers of B and T cells. A mouse model recapitulates the effects found in patients including a >20-fold reduction in CD3+ T cells. The observed B and T cell lymphopenia does not appear to be due to failure of B and T cells to develop in the bone marrow or mature in the thymus and remains unexplained. Neutrophilia was also noted in Rac2[E62K]. Additionally, patients can be cured by bone marrow transplantation, demonstrating that the effect is autonomous to bone marrow derived cells.

The results of Example 12 together with the results reported in Examples 7 to 11, support the conclusion that the lymphopenia observed in Rac[E62K] patients are causes by hyperactivity of phagocytes and premature engulfment of B and T cells, as further elaborated in Example 14.

Example 14: Stimulating Phagocytosis of Cancer Cells by Activating Rac in Macrophages Since a normal function of macrophages is to remove B and T cells when they turn over, the data of Example 12 support the conclusion that hyperactive Rac is causing the macrophages to prematurely consume the B and T cells before they would normally die and support the conclusion that the hyperactive macrophages were "eating" and thereby killing the patients B and T cells.

Since in Example 12, the Rac-activated macrophages (but not control macrophages) avidly consumed and killed the Jurkat cells, this proof-of-principle experiment supports the conclusion that expressing activating mutations in Rac in the macrophages of cancer patients might cause the macrophages to kill and consume the cancer cells, tipping the balance—in the war between cancer and the immune system, in favor of the immune system and patient survival.

Example 15: Rac Activated CAR Combination for Targeted Cell Killing and Phagocytosis CAR-T is a cancer therapy based on the premise of engineering patient T cells to attack cancerous B cells. CAR-P is a therapeutic approach based on the idea that macrophages can be programmed to attack cancer cells.

However existing approaches are based on programming T cells and macrophages to express an extracellular receptor protein that causes them to bind B cells. Only a small fraction of cell-cell contact events lead to engulfment and death of the tumor cell. 80% of events lead to a non-lethal cell "nibbling" behavior.

Based on the experiments in *Drosophila* reported in Examples 7 to 10, and the data with mammalian cells discussed in Example 11 and 12, it is expected that expressing activating mutations in Rac2 in macrophages and/or neutrophils has the potential to vastly improve the efficiency of published CAR-P as outlined in the following prophetic Examples 18 and 19.

Example 16: Rac Active Vector Configurations

In a genetically engineered activated phagocyte, Rac gene has to be co-expressed with a reporter gene (FIG. 7A) in order to detect its presence by quantitative or qualitative methods except if Rac gene contains a tag sequence upstream or downstream of it (FIG. 7B) allowing its own detection by those methods specially for studies in vivo. Bicistronic vectors containing PA or Internal Ribosomal Entry Site (IRES) sequences allowing the simultaneous expression of Rac gene and the reporter gene separately but from the same RNA transcript are mostly preferred (FIG. 7C). Promoter of bicistronic vectors can be the same used to express Rac gene alone. If one different promoter is used, it has to have at least one core promoter followed by Rac gene and the presence of number of the regulatory sequences can be optional. Co-expression of Rac and the reporter gene coming from two different vectors can be accepted. In that case, the second vector has to contain at least a core promoter upstream of the reporter gene and the usage of regulatory regions can be optional. This will be considered as the minimal cassette and at least one copy will be required for proper expression of the reporter gene. The promoter in the second vector can be constitutive or conditional, homologous or heterologous with respect to the phagocyte. If co-expression of Rac and the reporter gene is coming from different vectors, the same kind of genomic insertion in the phagocyte cell will be preferred (stable transfection). In this case, the order of the creation of stable phagocytic cells expressing Rac or the reporter gene in first place will be arbitrary. At the end, phagocytic cells expressing both Rac and the reporter genes can be identified and selected by quantitative or qualitative methods.

Figure 8A:
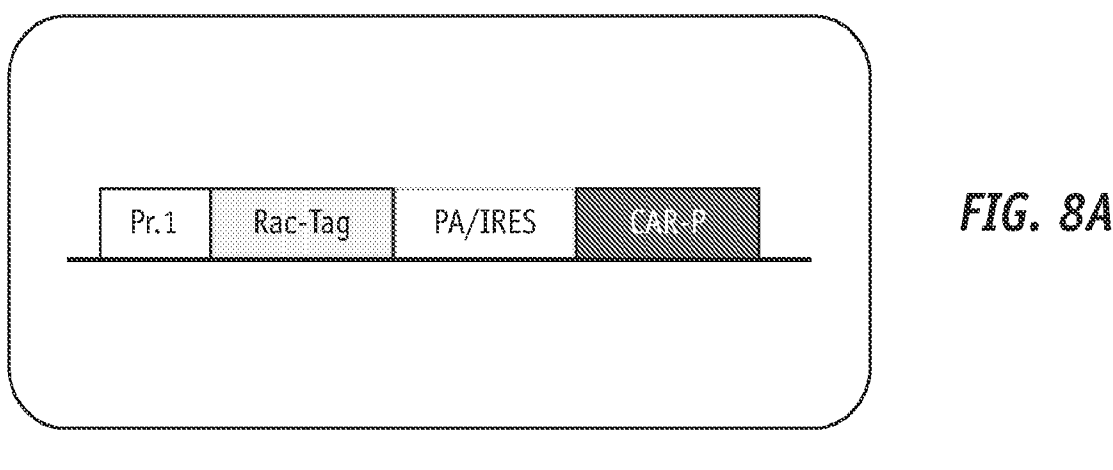
Figure 8B:
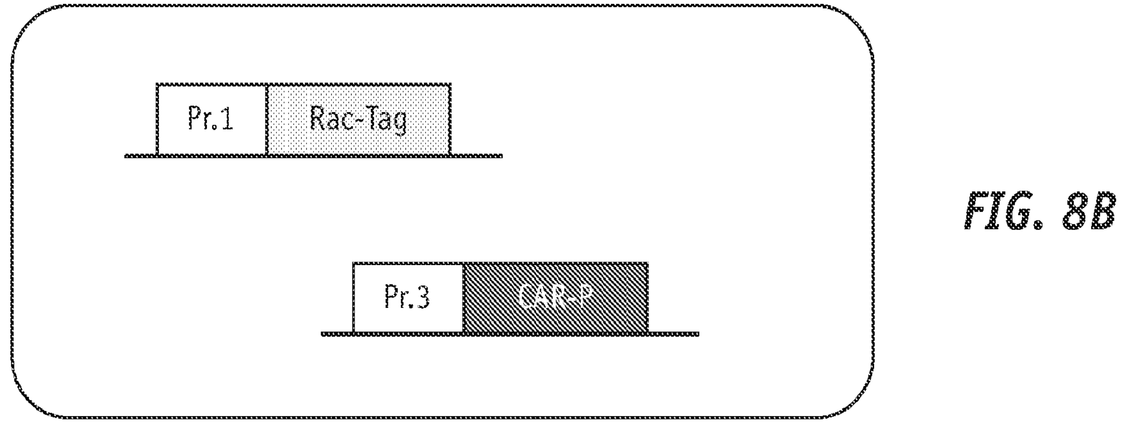
Figure 8C:
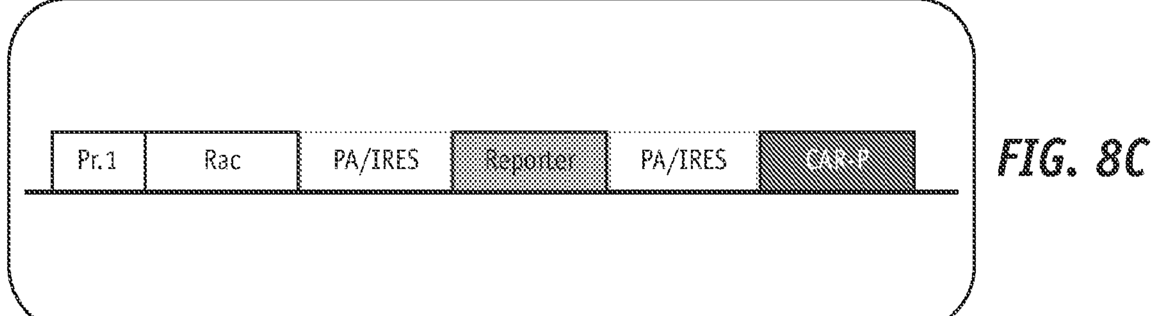

In order to enhance phagocytosis of living cells by the genetically engineered activated phagocyte a Chimeric Antigen Receptor for Phagocytosis (CAR-P) can be co-expressed with Rac gene. CAR-P gene has to contain in its C-terminus a tag or a reporter gene different to the one used to detect Rac expression. As in the case of co-expression of Rac and the reporter gene, expression of Rac and CAR-P genes can be done by using bicistronic vectors (FIG. 8A) or by two different vectors expressing everyone one gene but, in this case, Rac gene has to have a tag sequence upstream or downstream of it (FIG. 8B). Multicistronic vectors expressing Rac gene without any tag, the reporter gene and CAR-P in the same transcript can be used without any preference on the order of the genes upstream or downstream of the PA or IRES sequences (FIG. 8C). The first promoter can be used in this multicistronic vector however if one different promoter is used, it has to have at least one core promoter followed by Rac gene and the presence of number of the regulatory sequences can be optional.

Figure 8D:
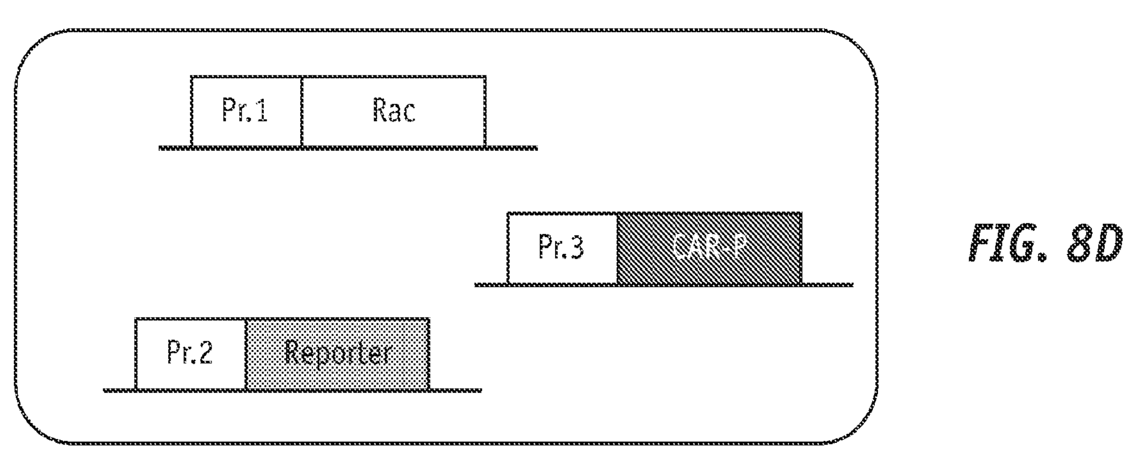

If CAR-P is co-expressed in a different vector than Rac, this third vector has to contain at least a core promoter upstream of CAR-P gene and the usage of regulatory regions can be optional. This will be considered as the minimal cassette and at least one copy will be required for proper expression of CAR-P gene. The promoter in this third vector can be constitutive or conditional, homologous or heterologous with respect to the phagocyte. However, constitutive promoters are the most preferred for CAR-P expression. In addition to the first and third vector expressing Rac and CAR-P genes respectively, the presence of a second vector expressing a reporter gene is required only if the first vector does not contain a tag sequence upstream or downstream of Rac gene (FIG. 8D).

The genetically engineered activated phagocyte can have one of these different combinations (FIG. 9A, 9B) if bicistronic vectors are used at the same time of single vectors. In these combinations, the Rac gene does not have a tag sequence upstream or downstream and the order of the genes in the bicistronic vector can be arbitrary.

If co-expression of Rac and CAR-P genes or Rac, CAR-P and reporter genes is coming from different vectors or different combinations of bicistronic and single vectors, the same kind of genomic insertion in the phagocyte cell will be preferred (stable transfection). In this case, the order of the creation of stable phagocytic cells expressing Rac or CAR-P gene or reporter gene in first place will be arbitrary. At the end, phagocytic cells expressing the different genes can be identified and selected by quantitative or qualitative methods.

Example 17: Rac Active Genetic Circuit Configurations

An exemplary genetic circuit for expressing an activated Rac protein and/or an activated or non-activated Rag gene at activating expression levels includes cloning of a fluorescently labelled wild type Rac2 (RAC2 [WT] or dominant activated Rac2 {Rac2 [E62K]} in a conditional, doxycycline inducible (Tet ON), lentiviral or adenoviral, mammalian expression vector and transfecting them in macrophage or neutrophil cell lines (HL60).

These cells will only express the gene cassette when induced with doxycycline. The expression of the activated Rac gene can be monitored by the expression of GFP when induced by doxycycline. In co-culture with another fluorescently labeled target cells (HA-mCherry expressing Jurkat T cells), the macrophages or neutrophils will completely or partially engulf (trogocytosis) the target cells. This can be monitored in live and fixed imaging and can be quantified by flow cytometry.

Example 18: RAC2[E62K] Differentiated Macrophages can Kill and/or Engulf a Range of Lymphoma and Leukemia Cells.—PROPHETIC The most significant limitation of the current CAR-P approach is that the engineered macrophages display robust cell nibbling but infrequent whole cell engulfment (Morrissey, Williamson et al. 2018) One mechanism limiting the efficiency of CAR-P is that tumorcells frequently up-regulate expression of 'don't-eat-me' signals, such as CD47 (Morrissey and Vale 2019).

Efficient engulfment of CD47+ Jurkat cells by RAC2 [E62K] expressing macrophages reported in Example 12, indicates that hyperactivation of Rac is sufficient to overcome this inhibition. In particular Data of Example 6 show that RAC2[E62K]-expressing, HL60-derived human macrophages efficiently engulf and kill Jurkat leukemic T-cells. RAC2[E62K] cells often engulf more than one target cell. This indicates that engineering macrophages to express hyperactive Rac may improve current CAR-P therapies.

On this basis an effectiveness of RAC2[E62K]-expressing macrophages to kill a variety of human leukemia and lymphoma cell lines is expected.

A RAC2[E62K] plasmid received from Prof. Steven Holland's lab at NIAID has been engineered to generate a stable, doxycycline (DOX) inducible, HL60 neutrophil-like cell line expressing RAC2[E62K] and GFP by lentiviral infection.

These cells will be differentiated into macrophages by adding 16 nm, 12-O-tetradecanoylphorbol13-acetate (TPA) in the culture medium for 48 hrs. mCherry will be stably expressed by lentiviral infection in a panel of nine lymphoma cell lines (ATCC TCP-1015) and L1210 cells (mouse lymphocytic leukemia cell line). Further, these cells will be co-cultured with GFP expressing RAC2[E62K] differentiated HL60 macrophages. Fixed imaging will be carried out to see if the macrophages can engulf the mCherry-expressing tumor cells and quantify the engulfment percentage by fluorescence sorting. HL60 cells expressing GFP alone will be used as negative controls. Further, a RAC2[E62K] mouse is expected to confirm that primary, bone marrow-derived macrophages from RAC2[E62K] mice are as effective as (or possibly more effective than) HL60-derived macrophages at engulfing hematopoietic cancer cells.

The RAC2[E62K] macrophages efficiently engulfing and/or killing all of the lymphoma and leukemia cells will demonstrate a treatment approach for a variety of hematopoietic cancers. If the RAC2[E62K] macrophages engulf the cells before killing them, a conclusion will be made that RAC2[E62K] activates phagoptosis (killing by engulfment). Alternatively, if the RAC2[E62K]-macrophages kill the tumor cells prior to engulfing them, conclusion will be made that the mechanism of tumor cell killing is more likely due to the process of nibbling to death. A quantification will be performed of the nibbling efficiency in RAC2[E62K]- macrophages for all tumor cell lines compared to the only GFP expressing control.

An increased nibbling and not complete engulfment will be possibly observed in some of the tumor cell lines. To increase the engulfment efficiency for these tumors, a cell surface receptor that recognizes target apoptotic cells by macrophages by binding to the phosphatidylserine (PS) residues will be co-expressed. Two such receptors include T cell immunoglobulin (Ig)- and mucin domain-containing molecule (Tim4) and the integrin aVb3 bound to milk fat globule epidermal growth factor (EGF) factor 8 (MFG-E8; also known as lactadherin). (Onuma, Komatsu et al. 2014) Engulfment efficiencies of macrophages co-expressing the cell surface receptors along with RAC2[E62K] will be tested.

If killing of some of the tumor cell lines by RAC2[E62K] expressing macrophages will not be observed, another intriguing possibility that will be tested is whether the hyperactive macrophages can kill cancer cells indirectly. For example, RAC2[E62K] expressing cells exhibit increased macropinocytosis (or cell drinking), a process that involves uptake of extracellular material such as nutrients and growth factors (Hsu, Donkó et al. 2019) This may limit the nutrient availability for tumor cells and promote cell death. Tumor cells will be grown in a conditioned medium from macrophages expressing GFP control, RAC2-WT, and RAC2 [E62K]. If RAC2[E62K] expression leads to increased macropinocytosis, tumor cells growing in conditioned medium from RAC2[E62K] will show increased cell death. This will be assayed by increased Trypan Blue uptake by dead tumor cells. As another negative control, conditioned medium from parental tumor cells will also be used. Another possibility is that hyperactive macrophages produce excess reactive oxygen species (ROS), which may be toxic to tumor cells. To test this possibility, RAC2[E62K] macrophages and tumor cells will be co-coltured with and without ROS inhibitors such as N-acetyl-cysteine (NAC) and quantify living/dead tumor cells.

Example 19: Engulfment Efficiency of Rac2[E62K] Macrophages Against Solid Tumor Cell Lines The observation that differentiated HL60 macrophages expressing RAC2[E62K] can engulf immortalized Jurkat leukemic T-cells suggests that RAC2[E62K] mediated engulfment can further improve the efficiency of CAR-P/M methods that target solid tumors (Klichinsky, Ruella et al. 2020) Work published just a few weeks ago shows that macrophages engineered to express receptors that recognize solid tumor antigens led to tumor clearance in vitro and in two solid tumor xenograft mouse models (Klichinsky, Ruella et al. 2020) in addition to direct killing by engulfment, the CAR-M macrophages also present tumor antigens to T cells leading to enhanced T-cell infiltration and cytotoxicity (Klichinsky, Ruella et al. 2020).

Having established this platform, the most pressing future work will be to enhance the approach by using rational combinations, and highlight "agents" that affect phagocytosis. The data discussed in Examples 7-15 indicates that co-expressing Rac2[E62K] would be an effective and rational agent for combination CAR-M therapy, vastly expanding the range of patients who might be effectively treated by immunotherapy.

RAC2[E62K] macrophages will be co-cultured with mCherry-expressing MDA-MB-453 or BT-474cells (breast cancer cell lines), SW1116 cells (human colon cancer cell line), and SKOV3 (ovarian cancer cells). All these cell lines express tumor antigen HER2 (Heyerdahl, Krogh et al. 2011, Jernström, Hongisto et al. 2017, Conradi, Spitzner et al. 2019) Fixed imaging will be carried out to see if the RAC2[E62K] expression alone is sufficient to cause macrophages to engulf these solid tumors and we will compare expression of anti-HER2 CAR alone, Rac2[E62K1] alone, or both together and quantify the engulfment potential by fluorescence activated sorting. Macrophages with GFP-expression alone will serve as a negative control.

An expected observation is that RAC2[E62K] is sufficient even in the absence of the anti-HER2 CAR to cause engulfment of solid tumor cells. Alternatively, or in addition, another expected observation is enhanced engulfment by co-expressing both. As in Example 18, increased nibbling but not whole cell engulfment or killing is possibly expected to occur.

If neither engulfment nor trogoptosis mediated killing of cancer cells by RAC2[E62K] expressing HL60 cells will be observed, it is expected that hyperactive macrophages may nevertheless have a therapeutic effect. They may limit cancer cell spread by mechanisms such as by increased secretion of proinflammatory factors and/or increased antigen presentation to T cells. The solid tumor microenvironment (TME) actively recruits tumor associated macrophages (TAMs) where they are polarized toward a pro-tumoral (decreased phagocytic potential for tumor cells) and immunosuppressive (M2) phenotype. (Jayasingam, Citartan et al. 2020) Therapeutic approaches to enhance their phagocytic potential are underway. (Morrison 2016, Mantovani, Marchesi et al. 2017) (Weiskopf 2017) It may be possible that RAC2[E62K] macrophages can promote expression of antitumoral M1-associated pathways.

To test this in RAC22[E62K] macrophages, we will check the expression of M1-associated interferon response genes (IFIT1, ISG15 and IFITM1, etc.), Till pathway and iNOS signaling, key components of the antigen presentation machinery such as costimulatory ligands (CD80, TAP1), HILA-A/B/C and MHC Class I/II genes by quantitative PCR and flow cytometry. If the expression levels of these genes are upregulated in RAC2[E62K] macrophages (compared to the GFP control), it will be possible to conclude that these macrophages may carry out killing of cancercells by promoting a proinflammatory response or increased antigen presentation to T cells. Alternatively, metastatic cancer cells thrive by feeding on their siblings and other cells from the immune system. (Caruso, Fedele et al. 2012) Hence, if the RAC2[E62K] macrophages cannot kill cancer cells at all, it will be tested whether the cancer cells can cannibalize the RAC2[E62K] macrophages. If the cancer cells cannot engulf macrophages efficiently, we will conclude that RAC2 [E62K] expressing macrophages may limit the cannibalistic potential of cancer cells by hyperactivating a Rac2 mediated response in macrophages. Such a process may potentially limit the metastatic spread of cancer cells.

Example 20: Rac Activated Cells for Treating Alzheimer's Disease

The impact of this study could possibly be even more significant because recent work suggests that increasing the phagocytic capacity of brain macrophages may be beneficial in mildly cognitively impaired patients with Alzheimer's disease. (Olivera-Perez, Laim et al. 2017).

The accumulation of the amyloid-β peptide (Aβ) in the brain is considered a hallmark of Alzheimer's disease (AD). Aβ aggregates both in soluble and insoluble fibrillar forms. Insoluble fibrillar amyloid-β (Aβ) load in AD patients does not correlate with AD dependent neurodegeneration or loss of cognitive function (Giannakopoulos et al. 2003) (Giannakopoulos, Herrmann et al. 2003), however, soluble small Aβ aggregates have shown memory impairment and other AD symptoms in several animal models and AD patients (Kuo et at 1996: Lesné et al. 2006; Panza et at 2019) (Kuo, Emmerling et at 1996) (Lesné, Koh et al. 2006) (Panza, Lozupone et al. 2019).

The efforts to target the soluble aggregates of Aβ are currently underway for developing an effective treatment. In vitro and in vivo studies have shown that microglia (macrophages in brain) can take up both soluble and fibrillar form of Aβ via phagocytosis (engulfment) and macropinocytosis (cell drinking).

Both these processes are dependent on Rac activation (Mandrekar et al. 2009). (Mandrekar, Jiang et al. 2009) Interestingly, expression of the engulfment receptor Draper in *Drosophila* glia reduces Aβ toxicity in a *Drosophila* model of AD (Ray et al. 2017). (Ray, Speese et at 2017) Our work in *Drosophila* ovary suggests that expression of Rac1 [G12V] in only a few cells can promote tissue scale engulfment.

Hence the expression of active Rac (Rac1[G12V]) in glial cells (e.g., microglial cells) is expected to render them hyper-phagocytic resulting in even more efficient clearance the Aβ.

In summary described herein are activated phagocytes, and in particular Genetically engineered activated phagocytic cells are described and related vectors, compositions, methods and systems which allow efficient cell targeting through enhanced phagocytosis of target cells and treatment of conditions in an individual.

The examples set forth above are provided to give those of ordinary skill in the art a complete disclosure and description of how to make and use the embodiments of the compounds, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including webpages patents, patent applications, journal articles, abstracts, laboratory manuals, books, or other disclosures) in the Background, Summary, Detailed Description, and Examples is hereby incorporated herein by reference. All references cited in this disclosure, including references cited in any one of the documents incorporated by reference, are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P2495-PCT-Seq-List_ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains. Also as used herein, "and/or" refers to and encompasses any and all possible combinations of one or more of the associated listed items, as well as the lack of combinations when interpreted in the alternative ("or").

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, ard materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

Buchler, N. E., et al. (2003). "On schemes of combinatorial transcription logic." *Proceedings of the National Academy of Sciences* 100(9): 5136-5141.

Cai, D., et al. (2014). "Mechanical feedback through E-cadherin promotes direction sensing during collective cell migration." *Cell* 157(5): 1146-1159.

Caruso, R., et al. (20121). "Neutrophil-tumor cell phagocytosis (cannibalism) in human turoms: an update and literature review." *Experimental oncology* 34: 306-311.

Caye, A., et al. (2015). "Juvenile myelomonocytic leukemia displays mutations in components of the RAS pathway and the PRC2 network." *Nature genetics* 47(11): 1334-1340.

Cliffe, A., et al. (2017). "Quantitative 3D analysis of complex single border cell behaviors in coordinated collective cell migration." *Nature communications* 8(1): 1-13 (Article number: 14905).

Conradi, L.-C., et al. (2019). "Combined targeting of HER-2 and HER-3 represents a promising therapeutic strategy in colorectal cancer." *BMC cancer* 19(1): 1-12.

Del Vecchio, D. and R. M. Murray (2014). *Biomolecular feedback systems*, Princeton University Press, 280 pages.

Elliott, M. R. and K. S. Ravichandran (2016). "The dynamics of apoptotic cell clearance." *Developmental cell* 38(2): 147-160.

Geisbrecht, E. R. and D. J. Montell (2004). "A role for *Drosophila* IAPI1-mediated caspase inhibition in Rac-dependent cell migration." *Cell* 118(1): 111-125.

Giannakopoulos, P., et al. (2003). "Tangle and neuron numbers, but not amyloid load, predict cognitive status in Alzheimer's disease." *Neurology* 60(9): 1495-1500.

Haataja, L., et al. (1997). "Characterization of RAC3, a novel member of the Rho family." *Journal of Biological Chemistry* 272(33): 20384-20388.

Hall, A. (1998). "Rho GTPases and the actin cytoskeleton." *Science* 279(5350): 509-514.

Heyerdahl, H., et al. (2011). "Treatment of HER2-expressing breast cancer and ovarian cancer cells with alpha particle-emitting 227Th-trastuzumab." *International Journal of Radiation Oncology*Biology*Physics* 79(2): 563-570.

Hsu, A. P., et al. (2019). "Dominant activating RAC2 mutation with lymphopenia, immunodeficiency, and cytoskeletal defects." *Blood* 133(18): 1977-1988.

Jayasingam, S. D., et al. (2020). "Evaluating the polarization of tumor-associated macrophages into M1 and M2 phenotypes in human cancer tissue: technicalities and challenges in routine clinical practice." *Frontiers in oncology* 9: 1512.

Jernström, S., et al. (2017). "Drug-screening and genomic analyses of HER2-positive breast cancer cell lines reveal predictors for treatment response." *Breast Cancer: Targets and Therapy* 9: 185.

Karlin, S. and S. F. Altschul (1990). "Methods for assessing the statistical significance of molecular sequence features by using general scoring schemes." *Proceedings of the National Academy of Sciences* 87(6): 2264-2268.

Karlin, S. and S. F. Altschul (1993). "Applications and statistics for multiple high-scoring segments in molecular sequences." *Proceedings of the National Academy of Sciences* 90(12): 5873-5877.

Kawazu. M., et al. (2013). "Transforming mutations of RAC guanosine triphosphatases in human cancers." *Proceedings of the National Academy of Sciences* 110(8): 3029-3034.

Klichinsky, M., et al. (2020). "Human chimeric antigen receptor macrophages for cancer immunotherapy." *Nature biotechnology* 38(8): 947-953.

Krauthammer, M., et al. (2012). "Exome sequencing identifies recurrent somatic RAC1 mutations in melanoma." *Nature genetics* 44(9): 1006-1014.

Kumar, A., et al. (2013). "Molecular dynamic simulation reveals damaging impact of RAC1 F28L mutation in the switch I region." *PloS one* 8(10): e77453.

Kuo. Y.-M., et al. (1996). "Water-soluble Aβ (N-40, N-42) oligomers in normal and Alzheimer disease brains." *Journal of Biological Chemistry* 271(8): 4077-4081.

Lagresle-Peyrou, C., et al. (2021). "A gain-of-function RAC2 mutation is associated with bone marrow hypoplasia and an autosomal dominant form of severe combined immunodeficiency." *haematologica* 106(2): 404.

Lesné, S., et al. (2006). "A specific amyloid-β protein assembly in the brain impairs memory." *Nature* 440 (7082): 352-357.

Lougaris, V., et al. (2019). "A monoallelic activating mutation in RAC2 resulting in a combined immunodeficiency." *Journal of Allergy and Clinical Immunology* 143(4): 1649-1653. e1643.

Mandrekar, S., et al. (2009). "Microglia mediate the clearance of soluble Aβ through fluid phase macropinocytosis." *Journal of Neuroscience* 29(13): 4252.-4262.

Mano, H. Compositions Comprising RAC Mutants, and Methods of Use Thereof US2015/0185223A1

Mantovani, A., et al. (2017). "Tumour-associated macrophages as treatment targets in oncology." *Nature reviews Clinical oncology* 14(7): 399.

Massol, P., et al. (1998). "Fe receptor-mediated phagocytosis requires CDC42 and Rac1." *The EMBO journal* 17(21): 6219-6229.

Matlung, H. L., et al. (2018). "Neutrophils kill antibody-opsonized cancer cells by trogoptosis." *Cell Reports* 23(13): 3946-3959. e3946.

Meehan, T. L., et al. (2015). "Polarization of the epithelial layer and apical localization of integrins are required for engulfment of apoptotic cells in the *Drosophila* ovary." *Disease models & mechanisms* 8(12): 1603-1614.

Menard, L. and R. Snyderman (1993). "Role of phosphate-magnesium-binding regions in the high GTPase activity of rac1 protein." *Biochemistry* 32(48): 13357-13361.

Milone, M. C., et al. (2009). "Chimeric receptors containing CD137 signal transduction domains mediate enhanced survival of T cells and increased antileukemic efficacy in vivo." *Molecular therapy* 17(8): 1453-1464.

Mishra. A. K., et al. (2019). "Coordination of protrusion dynamics within and between collectively migrating border cells by myosin II." *Molecular biology of the cell* 30(19): 2490-2502.

Montell, D. J., et al. (1992). "slow border cells, a locus required for a developmentally regulated cell migration during oogenesis, encodes *Drosophila* CEBP." Cell 71(1): 51-62.

Montell, D. J., et al. (2012). "Group choreography: mechanisms orchestrating the collective movement of border cells." *Nature reviews Molecular cell biology* 13(10): 631-645.

Morrison, C. (2016). "Immuno-oncologists eye macrophage targets." *Nature reviews Drug discovery* 15(6): 373-374.

Morrissey, M. A. and R. D. Vale (2019). "CD47 suppresses phagocytosis by repositioning SIRPA and preventing integrin activation." *bioRxiv:* 752311.

Morrissey, M. A., et al. (2018). "Chimeric antigen receptors that trigger phagocytosis." *Elife* 7: e36688.

Murphy, A. M. and D. J. Montell (1996). "Cell type-specific roles for Cdc42, Rac, and RhoL in *Drosophila* oogenesis." *The Journal of cell biology* 133(3): 617-630.

Myers, E. W. and W. Miller (1988). "Optimal alignments in linear space." *Bioinformatics* 4(1): 11-17.

Needleman, S. B. and C. D. Wunsch (1970). "A general method applicable to the search for similarities in the amino acid sequence of two proteins." *Journal of molecular biology* 48(3): 443-453.

Olivera-Perez, 11. M., et al. (2017). "Omega-3 fatty acids increase the unfolded protein response and improve amyloid-β phagocytosis by macrophages of patients with mild cognitive impairment." *The FASEB Journal* 31(10): 4359-4369.

Onuma, H., et al. (2014). "Rapidly rendering cells phagocytic through a cell surface display technique and concurrent Rac activation." *Science signaling* 7(334): rs4-rs4.

Pantarelli, C. and H. C. Welch (2018). "Rac-GTP ases and Rac-GFP s in neutrophil adhesion, migration and recruitment." *European journal of clinical investigation* 48: e12939.

Panza, F., et al. (2019). "Arnyloid-β immunotherapy for alzheimer disease: Is it now a long shot?" *Annals of neurology* 85(3): 303-315.

Pearson, W. R. and D. J. Lipman (1988). "Improved tools for biological sequence comparison." *Proceedings of the National Academy of Sciences* 85(8): 2444-2448.

Peterson, J., et al. (2003). "Stage-specific regulation of caspase activity in *Drosophila* oogenesis." *Developmental biology* 260(1): 113-123.

Prasad, M. and D. J. Montell (2007). "Cellular and molecular mechanisms of border cell migration analyzed using time-lapse live-cell imaging." *Developmental cell* 12(6): 997-1005.

Ray, A., et al. (2017). "Glial draper rescues Aβ toxicity in a *Drosophila* model of Alzheimer's disease." *Journal of Neuroscience* 37(49): 11881-11893.

Ridley, A. J. (2015). "Rho GTPase signalling in cell migration." *Current opinion in cell biology* 36: 103-112.

Ridley, A. J., et al. (1992). "The small GTP-binding protein rac regulates growth factor-induced membrane ruffling." *Cell* 70(3): 401-410.

Rorth, P., et al. (1998). "Systematic gain-of-function genetics in *Drosophila." Development* 125(6): 1049-1057.

Roth, T. L., et al. (2018). "Reprogramming human T cell function and specificity with non-viral genome targeting." *Nature* 559(7714): 405-409.

Sambrook, J., et al. (1989). *Molecular cloning: a laboratory manual* 2nd ed., Cold spring harbor laboratory press.

Serizier, S. B. and K. McCall (2017). "Scrambled eggs: Apoptotic cell clearance by non-professional phagocytes in the *Drosophila* ovary." *Frontiers in immunology* 8: 1642.

Silva-Rocha, R. and V. de Lorenzo (2008). "Mining logic gates in prokaryotic transcriptional regulation networks." *FEBS letters* 582(8): 1237-1244.

Smith, T. F. and M. S. Waterman (1981). "Comparison of biosequences." *Advances in applied mathematics* 2(4): 482-489.

Sompayrac, L. M. (2019). *How the immune system works* 6th edition, Malden, M A: Blackwell Publishing ISBN: 978-1-119-54212-4.

Struhl, G. and K. Basler (1993). "Organizing activity of wingless protein in *Drosophila." Cell* 72(4): 527-540.

Timmons, A. K., et al. (2016). "Phagocytosis genes nonautonomously promote developmental cell death in the *Drosophila* ovary." *Proceedings of the National Academy of Sciences* 113(9): E1246-E1255.

Van Tendeloo, V., et al. (2000). "High-level transgene expression in primary human T lymphocytes and adult bone marrow CD34+ cells via electroporation-mediated gene delivery." *Gene therapy* 7(16): 1431-1437.

Wang, X., et al. (2010). "Light-mediated activation reveals a key role for Rac in collective guidance of cell movement in vivo." *Nature cell biology* 12(6): 591-597.

Weiskopf, K. (2017). "Cancer immunotherapy targeting the CD47/SIRPα axis." *European journal of cancer* 76: 100-109.

Wikipedia, F. c. (20 Apr. 2021). "Fold change, https://en.wikipedia.org/wiki/Fold_change." Wikipedia, R. (31 Dec. 2020). "RAC1 https://en.wikipedia.org/wiki/RAC1".

Xu. X., et al. (1997). "Guanine nucleotide binding properties of Rac2 mutant proteins and analysis of the responsiveness to guanine nucleotide dissociation stimulator." *Biochemistry* 36(3): 626-632.

Zarani, F. E. and L. H. Margarifs (1991). "The eggshell of Drosophlla melanogaster." *Roux's archives of developmental biology* 200(2): 95-103.

Montell, D. J., Yoon, W. H. and Starz-Gaiano, M. 2012. Group choreography: mechanisms orchestrating the collective movement of border cells. *Nature Reviews. Molecular Cell Biology* 13(10), pp. 631-645. (Montell, Yoon et al. 2012)

Serizier. S. B. and McCall, K. 2017. Scrambled Eggs: Apoptotic Cell Clearance by Non-Professional Phagocytes in the *Drosophila* Ovary. *Frontiers in immunology* 8, p. 1642. (Serizier and McCall 2017)

The invention claimed is:

1. A genetically engineered activated phagocytic cell comprising an activated Rac-2 gene encoding an activated Rac-2 protein comprising an activating mutation, the activated Rac-2 gene under control of a first phagocyte promoter and a first additional phagocyte regulatory region in a configuration allowing expression of the activated Rac-2 gene in the genetically engineered activated phagocytic cell, wherein the activating mutation comprises at least one of E62K, Q61L, D63V, G12R, and G12V.

2. The genetically engineered phagocytic cell of claim 1, wherein the first phagocyte promoter is a constitutive promoter or a conditional promoter.

3. The genetically engineered phagocytic cell of claim 1, wherein the activated Rac-2 gene, the first phagocyte promoter and the first regulatory region is configured within a gene expression cassette.

4. The genetically engineered phagocytic cell of claim 1, wherein the genetically engineered activated phagocyte further comprises a chimeric antigen receptor (CAR) gene under control of the first phagocyte promoter or of a second phagocyte promoter, and optionally under a second additional phagocyte regulatory regions in a configuration allowing expression of the CAR in the activated phagocytic cell.

5. The genetically engineered phagocytic cell of claim 4, wherein the second phagocyte promoter is a constitutive promoter, wherein the constitutive promoter is selected from CMV from human cytomegalovirus, EF1a from human elongation factor 1 alpha, SV40 from the simian vacuolating virus 40, PGK1 from phosphoglycerate kinase gene, Ubc from human ubiquitin C gene, human beta actin, CAAG, and SynI promoters.

6. The genetically engineered phagocytic cell of claim 4, wherein the second phagocyte promoter is a conditional promoter, wherein the conditional promoter is selected from TET (tetracycline-response elements, TET-ON/TET-OFF), Lac, dCas-transactivator, Zinc-finger-TF, TALENs-ZF Gal4-uas, synNotch and inducible promoters based on endogenous signals TNF-alpha, and cFOS promoter.

7. The genetically engineered phagocytic cell of claim 4, wherein the CAR gene, the second phagocyte promoter and the second regulatory regions are configured within a gene expression cassette.

8. The genetically engineered phagocytic cell of claim 4, wherein the first phagocyte promoter is different from the second phagocyte promoter and/or the first additional regulatory regions are different from the second additional regulatory regions.

9. The genetically engineered phagocytic cell of claim 4, wherein the activated Rac-2 gene and the CAR gene are configured within a single gene expression cassette.

* * * * *